United States Patent
Chiang et al.

(10) Patent No.: US 7,514,596 B2
(45) Date of Patent: Apr. 7, 2009

(54) METHODS FOR SIMULTANEOUS CONTROL OF LIGNIN CONTENT AND COMPOSITION, AND CELLULOSE CONTENT IN PLANTS

(75) Inventors: Vincent Lee C. Chiang, Hancock, MI (US); Laigeng Li, Houghton, MI (US)

(73) Assignee: Board of Control of Michigan Technological University, Houghton, MI (US)

( * ) Notice: Subject to any disclaimer, the term of this patent is extended or adjusted under 35 U.S.C. 154(b) by 319 days.

(21) Appl. No.: 11/057,518

(22) Filed: Feb. 14, 2005

(65) Prior Publication Data

US 2005/0166283 A1 Jul. 28, 2005

Related U.S. Application Data

(63) Continuation of application No. 09/947,027, filed on Sep. 5, 2001, now Pat. No. 6,855,864.

(60) Provisional application No. 60/230,086, filed on Sep. 5, 2000.

(51) Int. Cl.
C12N 15/82 (2006.01)

(52) U.S. Cl. .................................................. 800/278

(58) Field of Classification Search ................. 800/278, 800/290
See application file for complete search history.

(56) References Cited

U.S. PATENT DOCUMENTS

| 5,451,514 A | 9/1995 | Boudet et al. |
| 5,633,439 A | 5/1997 | Walter |
| 6,015,943 A | 1/2000 | Boudet et al. |
| 6,066,780 A | 5/2000 | Boudet et al. |

FOREIGN PATENT DOCUMENTS

WO     WO 01/27241     4/2001

OTHER PUBLICATIONS

Anterola et al (2002, Phytochemistry 61:221-294).*
Hu et al (1999, Nature Biotechnology 17:808-812).*
Franke et al (2000, Plant Journal 22(3):223-234).*
Bowie et al, Science 247:1306-1310, 1990.*
McConnell et al, Nature 411 (6838):709-713, 2001.*
Brill et al., "Molecular Characterisation and Expression of a Wound-Inducible cDNA Encoding a Novel Cinnamyl-Alcohol Dehydrogenase Enzyme in Lucerne (*Medicago sativa* L.)," *Plant Molecular Biol.*, 41:279-291 (1999).
Hibino et al., "Cinnamyl Alcohol Dehydrogenase from *Aralia cordata*: Cloning of the cDNA and Expression of the Gene in Lignified Tissues," *Plant Cell Physiol.*, 34:5:659-665 (1993).
Leyva et al., "*cis*-Element Combinations Determine Phenylalanine Ammonia-Lyase Gene Tissue-Specific Expression Patterns," *The Plant Cell*, 4:263-271 (1992).

O'Malley et al., "Purification, Characterization, and Cloning of Cinnamyl Alcohol Dehydrogenase in Loblolly Pine (*Pinus taeda* L.)," *Plant Physiol.*, 98:1364-1371 (1992).
Bugos et al., 1991, *Plant Mol. Biol.* 17:203.
Chang, H.M., and Sarkanen, K.V., 1973, *Tappi* 56:132.
Hu et al., 1999, *Nature Biotech.* 17:808.
Marton, J., Sarkanen, K.V., and Ludwig, C.H., eds (Wiley-Interscience, New York), 639, In "Lignins" (1971) ed Sarkanen, K.V. and Ludwig, CH.
Tsai et al., 1994, *Plant Cell Report* 14:94.
Boudet et al., 1995, *New Phytol.* 129:203.
Ibrahim, 1997, *Trends Plant Sci.* 2:249.
Joshi and Chiang, 1998, *Plant Mol. Biol.* 37:663.
Brasileiro et al., 1991, *Plant Mol. Bio.* 17:441.
Brasileiro et al., 1992, *Transgenic Res.* 1:133.
Chen et al., 1998, *Nature Biotechnology* 16, 11:1060.
Chen et al., 1999, *Planta* 207:597.
Vasil et al., 1996, *Bio/Technology* 10:667.
Danekar et al., 1987, *Bio/Technology* 5:587.
De Block, 1990, *Plant Physiol.* 93:1110.
Ebinuma et al., 1997, *Proceedings of the National Academic of Sciences* 94:2117.
Fillatti et al., 1987, *Mol. Gen. Genet.* 206:192.
Freudenberg, K., 1965, *Science* 148:595.
Horsch et al., 1985, *Science* 227:1229.
Howe et al., 1991, *Woody Plant Biotech.* Plenum Press, New York, 283.
Hu et al., 1998, *Proc. Natl. Acad. Sci. USA* 95:5407.
Humphreys et al., 1999, *Proc. Nat. Acad. Sci. USA* 96:10045.
Jornvall et al., 1987, *Eur. J. Biochem.* 167:195.
Jefferson et al., 1987, *Plant Molecular Biology Reporter*, 5:387.
Lawton et al., 1987, *Plant Mol. Biol.* 9:315.
Buxton and Roussel, 1988, *Crop. Sci.* 28,:553.
Jung and Vogel, 1986, *J. Anim., Sci.* 62:1703.
Leple et al., 1992, *Plant Cell Reports* 11:137.
Li et al, 1997, *Proc. Natl. Acad. Sci. USA* 94:5461.
Li et al., 1999, *Plant Mol. Biol.* 40:555.
Li et al., 2000, *J. Biol. Chem.* 275:6537.
McGranahan et al., 1988, *Bio/Technology* 6:800.
McGranahan et al., 1990, *Plant Cell Reports* 8:512.

(Continued)

*Primary Examiner*—Stuart F. Baum
(74) *Attorney, Agent, or Firm*—Michael Best & Friedrich LLP

(57) ABSTRACT

The present invention relates to a method of concurrently introducing multiple genes into plants and trees is provided. The method includes simultaneous transformation of plants with multiple genes from the phenylpropanoid pathways including 4CL, CAld5H, AldOMT, SAD and CAD genes and combinations thereof to produce various lines of transgenic plants displaying altered agronomic traits. The agronomic traits of the plants are regulated by the orientation of the specific genes and the selected gene combinations, which are incorporated into the plant genome.

1 Claim, 29 Drawing Sheets

OTHER PUBLICATIONS

Nelson et al. 1996, *Pharmacogenetics* 6:1.
Odell et al., 1985, *Nature* 313:810.
Parsons et al., 1986, *Bio/Technology* 4:533.
Pythoud et al., 1987, *Bio/Technology* 5:1323.
Sullivan et al., 1993, *Plant Cell Reports* 12:303.
Sarkanen, K.V., and Hergert, H.L., 1971, *Lignins: Occurrence, Formation, Structure and Reaction*, K.V. Sarkanen and C.H. Ludwig, eds (New York: Wiley-Interscience), 43.
Trotter, P.C., 1990, *Tech. Assoc. Pulp Paper Ind. J.* 73:198.
Tsai et al., 1998, *Plant Physiol.* 117:101.
Walker et al., 1987, *PNAS USA* 84:6624.
Wang et al., 1992, *Mol. Cell. Biol.* 12:3399.
Wu et al., 2000, *Plant J.* 22:495.
Yang et al., 1990, *PNAS USA* 87:4144.
Yamazaki et al., 1993, *J. Biochem.* 114:652.
Zhang, X.-H., and Chiang, V.L., 1997, *Plant Physiol.* 113:65.
Needleman and Wunsch, 1970 J. Mol. Biol. 48: 443-453.
Alt-Mörbe et al., 1989, *Mol. Plant-Microbe. Interac.*, 2:301-308.
Chandler et al., 1989, *The Plant Cell*, 1:1175-1183.
Chen, Ph.D. Thesis, 1991, North Carolina State University, Raleigh, North Carolina.
Chiang, V.L., and Funaoka, M., 1990, *Holzforschung* 44:309.
Ebert et al. 1987, *PNAS USA*, 84:5745-5749.
Fullner and Nester, 1996, *J. Bacteriol.*, 178:1498-1504.
Fullner et al., 1996, *Science*, 273:11071109.
Huang et al., 1991, In Vitro Cell Dev. Bio., 4:201.
Hudspeth et al., 1989, *Plant Mol. Biol.*, 12:579-589.
Klopfenstein et al., 1991, *Can. J. For. Res.* 21:1321.
Laursen et al., 1994, *Plant Mol. Biol.*, 24:51-61.
Li et al., 2001, *Plant Cell*, 13:1567-1585.
MacKay et al., 1995, *Mol. Gen. Genet.* 247:537.
Minocha et al., 1986, *Proc. TAPPI Research and Development Conference*, TAPPI Press, Atlanta, 89.
Nilsson, et al., 1992, *Transgenic Res.*, 1:209-220.
Osakabe et al., 1999, *Proc. Nati. Acad. Sci. USA* 96:8955-8960.
Sambrook et al., 2$^{nd}$ ed. 1982.
Spencer et al., 1992, *Plant Mol. Biol.*, 18:201-210.
Tricoli et al., 1995, *Bio/Technology*, 13:1458-1465.
Wilde et al., 1992, *Plant Physiol.*, 98:114-120.
Kajita, et al., 1996, *Plant Cell Physiol.*, 37(7): pp. 957-965.
Napoli et al., 1990, *The Plant Cell*, 2: 279-289.
van der Krol, 1988, *Nature* 333: 866-869.
Bugos et al., 1992, *Phytochemistry*, vol. 31, No. 5, pp. 1495-1498.
EMBL Acc#X62096 Bugos et al., 1991; Alignment with SEQ ID No. 6.
Bevan et al., 1983, *Nature*, 304:184.
Hu, et al., 1998, *PNAS USA*, 95:5407.
Gou, et al., *The Plant Cell*, Jan. 2001, v13, 73-88.
MacKay, et al., *PNAS USA*, Jul. 22, 1997; 94(15): 8255-8260.
Parvathi, et al., *The Plant Journal*, 2001, 25(2): 193-202.
Kajita et al., *Plant Science*, 1997, 128:109-118.
Piquemal et al., *Plant Journal*, 1998, 13(1):71-83.
Anterola et al., *Phytochemistry*, 2002, 61:221-294.
Moonan et al, *Journal of Virology*, 2002, 76(3):1339-1348.
Levee, et al., *Molecular Breeding*, 1999, 5:429-440.

\* cited by examiner

FIG. 2A SAD cDNA sequence (SEQ ID NO: 1).

```
   1  TTTTTTTTTT TTTCCTAGCC TTCCTTCTCG ACGATATTTC TCTATCTGAA
  51  GCAAGCACCA TGTCCAAGTC ACCAGAAGAA GAACACCCTG TGAAGGCCTT
 101  CGGGTGGGCT GCTAGGGATC AATCTGGTCA TCTTTCTCCC TTCAACTTCT
 151  CCAGGAGGGC AACTGGTGAA GAGGATGTGA GGTTCAAGGT GCTGTACTGC
 201  GGGATATGCC ATTCTGACCT TCACAGTATC AAGAATGACT GGGGCTTCTC
 251  CATGTACCCT TTGGTTCCTG GCATGAAAT TGTGGGGGAA GTGACAGAAG
 301  TTGGGAGCAA GGTGAAAAAG GTTAATGTGG GAGACAAAGT GGGCGTGGGA
 351  TGCTTGGTTG GTGCATGTCA CTCCTGTGAG AGTTGTGCCA ATGATCTTGA
 401  AAATTACTGT CCAAAAATGA TCCTGACATA CGCCTCCATC TACCATGACG
 451  GAACCATCAC TTACGGTGGC TACTCAGATC ACATGGTCGC TAACGAACGC
 501  TACATCATTC GATTCCCCGA TAACATGCCG CTTGACGGTG GCGCTCCTCT
 551  CCTTTGTGCC GGGATTACAG TGTATAGTCC CTTGAAATAT TTTGGACTAG
 601  ATGAACCCGG TAAGCATATC GGTATCGTTG GCTTAGGTGG ACTTGGTCAC
 651  GTGGCTGTCA AATTTGCCAA GGCCTTTGGA TCTAAAGTGA CAGTAATTAG
 701  TACCTCCCCT TCCAAGAAGG AGGAGGCTTT GAAGAACTTC GGTGCAGACT
 751  CATTTTTGGT TAGTCGTGAC CAAGAGCAAA TGCAGGCTGC CGCAGGAACA
 801  TTAGATGGCA TCATCGATAC AGTTTCTGCA GTTCACCCCC TTTTGCCATT
 851  GTTTGGACTG TTGAAGTCTC ACGGGAAGCT TATCTTGGTG GGTGCACCGG
 901  AAAAGCCTCT TGAGCTACCT GCCTTTTCTT TGATTGCTGG AAGGAAGATA
 951  GTTGCCGGGA GTGGTATTGG AGGCATGAAG GAGACACAAG AGATGATTGA
1001  TTTTGCAGCA AAACACAACA TCACAGCAGA TATCGAAGTT ATTTCAACGG
1051  ACTATCTTAA TACGGCGATA GAACGTTTGG CTAAAAACGA TGTCAGATAC
1101  CGATTCGTCA TTGACGTTGG CAATACTTTG GCAGCTACGA AGCCCTAAGG
1151  AGAAGATCCC ATGTTCTCGA ACCCTTTATA AAATCTGATA ACATGTGTTG
1201  ATTTCATGAA TAAATAGATT ATCTTTGGGA TTTTTCTTTA ATAAACGAAG
1251  TGTTCTCGAA AACTTAACAT CGGCAATACC CTGGCAGCTA CGAGAAACGC
1301  TTTAGAATTG TTTGTAAGTT TGTTTCATTA GGGTGATACC ATGCTCTCGA
1351  GTCCTTTGTA AGATCCATTT ATAGTTGCGT GAATGCTATG AACAAATAAT
1401  ATGTTTGCGG CTTCTCTTCA AAAAAAAAA AAAAAAAAA AAAAAA
```

FIG. 2B SAD protein sequence (SEQ ID NO: 2).

| | | | | |
|---|---|---|---|---|
| 1 | MSKSPEEEHP | VKAFGWAARD | QSGHLSPFNF | SRRATGEEDV | RFKVLYCGIC |
| 51 | HSDLHSIKND | WGFSMYPLVP | GHEIVGEVTE | VGSKVKKVNV | GDKVGVGCLV |
| 101 | GACHSCESCA | NDLENYCPKM | ILTYASIYHD | GTITYGGYSD | HMVANERYII |
| 151 | RFPDNMPLDG | GAPLLCAGIT | VYSPLKYFGL | DEPGKHIGIV | GLGGLGHVAV |
| 201 | KFAKAFGSKV | TVISTSPSKK | EEALKNFGAD | SFLVSRDQEQ | MQAAAGTLDG |
| 251 | IIDTVSAVHP | LLPLFGLLKS | HGKLILVGAP | EKPLELPAFS | LIAGRKIVAG |
| 301 | SGIGGMKETQ | EMIDFAAKHN | ITADIEVIST | DYLNTAIERL | AKNDVRYRFV |
| 351 | I DVGNTLAAT | KP* | | | |

FIG. 3A  Aspen (*P. tremuloides*) PtCAld5H cDNA sequence (SEQ ID NO: 3).

```
   1  TAAAGTCTTG TGGATTACAC AAAATACAGA CTGAAAACAT CCATAGGCAC
  51  CAACACATAA ACCATCCATG GATTCTCTTG TCCAATCTTT GCAAGCTTCA
 101  CCCATGTCTC TCTTCTTGAT CGTTATCTCT TCACTCTTCT TCTTCGGTCT
 151  CCTCTCTCGC CTTCGCCGAA GATTGCCATA TCCACCAGGG CCTAAAGGGT
 201  TGCCACTTGT AGGTAGCATG CACATGATGG ACCAAATAAC TCACCGTGGG
 251  TTAGCTAAAC TAGCTAAGCA ATATGGTGGG CTCTTTCATA TGCGCATGGG
 301  GTACTTGCAT ATGGTCACTG TTTCATCTCC TGAAATAGCT CGCCAAGTTC
 351  TGCAGGTCCA GGACAACATT TTCTCCAACA GACCAGCCAA CATAGCCATA
 401  AGTTACTTAA CCTATGATCG TGCAGATATG GCCTTTGCCC ACTACGGTCC
 451  TTTCTGGCGA CAGATGCGTA AGCTCTGCGT CATGAAGCTT TTTAGCCGGA
 501  AAAGGGCTGA ATCATGGAG TCTGTGAGAG ATGAGGTGGA CTCAATGCTT
 551  AAGACAGTTG AAGCCAATAT AGGCAAGCCT GTGAATCTTG GGAATTGAT
 601  TTTTACGTTG ACCATGAACA TCACTTACAG AGCAGCTTTC GGGGCTAAAA
 651  ATGAAGGACA GGATGAGTTC ATCAAGATTT TGCAGGAGTT CTCTAAGCTT
 701  TTTGGAGCAT TCAACATGTC TGATTTCATT CCCTGGCTGG GCTGGATTGA
 751  CCCCCAAGGG CTCAGCGCTA GACTTGTCAA GGCTCGCAAG GCTCTTGATA
 801  GATTCATCGA CTCTATCATC GATGATCATA TCCAGAAAAG AAAACAGAAT
 851  AAGTTCTCTG AAGATGCTGA AACCGATATG GTCGATGACA TGCTAGCCTT
 901  TTATGGTGAA GAAGCAAGGA AAGTAGATGA ATCAGATGAT TTACAAAAG
 951  CCATCAGCCT TACTAAAGAC AACATCAAAG CCATAATCAT GGATGTGATG
1001  TTTGGTGGGA CAGAGACGGT GGCGTCGGCA ATAGAGTGGG TCATGGCGGA
1051  GCTAATGAAG AGTCCAGAGG ATCAAAAAAG AGTCCAGCAA GAGCTCGCAG
1101  AGGTGGTGGG TTTAGAGCGG CGCGTGGAGG AAAGTGATAT TGACAAACTT
1151  ACGTTCTTGA AATGCGCCCT CAAAGAAACC TTAAGGATGC ACCCACCAAT
1201  CCCACTTCTC TTACATGAAA CTTCTGAGGA TGCTGAGGTT GCTGGTTATT
```

FIG. 3A (Continued)

```
1251   TCATTCCAAA GCAAACAAGG GTGATGATCA ATGCTTATGC TATTGGGAGA
1301   GACAAGAATT CATGGAAGA TCCTGATGCT TTTAAGCCTT CAAGGTTTTT
1351   GAAACCAGGG GTGCCTGATT TTAAAGGGAA TCACTTTGAG TTTATTCCTT
1401   TCGGGTCTGG TCGGAGGTCT TGCCCCGGTA TGCAGCTTGG GTTATACACA
1451   CTTGATTTGG CTGTTGCTCA CTTGCTTCAT TGTTTTACAT GGGAATTGCC
1501   TGATGGCATG AAACCGAGTG AACTTGACAT GACTGATATG TTTGGACTCA
1551   CCGCGCCAAG AGCAACTCGA CTCGTTGCCG TTCCGAGCAA GCGTGTGCTC
1601   TGTCCTCTCT AAGGAAGGGA AAAAGGTAAG GGATGGAAAT GAATGGGATT
1651   CCCTTCTTTC GTGGATTCTA TACAGAATTG AGGCCATGGT GACAAAGGGT
1701   CAATTTGCAG GTTTTTTTTT TTATATATAT ATATATATAA TTGGGTTAAA
1751   AAAAAAAAAA AAAA
```

FIG. 3B Aspen (*P. tremuloides*) PtCald5H protein sequence (SEQ ID NO: 4).

```
  1  MDSLVQSLQA  SPMSLFLIVI  SSLFFFGLLS  RLRRRLPYPP  GPKGLPLVGS
 51  MHMMDQITHR  GLAKLAKQYG  GLFHMRMGYL  HMVTVSSPEI  ARQVLQVQDN
101  IFSNRPANIA  ISYLTYDRAD  MAFAHYGPFW  RQMRKLCVMK  LFSRKRAESW
151  ESVRDEVDSM  LKTVEANIGK  PVNLGELIFT  LTMNITYRAA  FGAKNEGQDE
201  FIKILQEFSK  LFGAFNMSDF  IPWLGWIDPQ  GLSARLVKAR  KALDRFIDSI
251  IDDHIQKRKQ  NKFSEDAETD  MVDDMLAFYG  EEARKVDESD  DLQKAISLTK
301  DNIKAIIMDV  MFGGTETVAS  AIEWVMAELM  KSPEDQKRVQ  QELAEVVGLE
351  RRVEESDIDK  LTFLKCALKE  TLRMHPPIPL  LLHETSEDAE  VAGYFIPKQT
401  RVMINAYAIG  RDKNSWEDPD  AFKPSRFLKP  GVPDFKGNHF  EFIPFGSGRR
451  SCPGMQLGLY  TLDLAVAHLL  HCFTWELPDG  MKPSELDMTD  MFGLTAPRAT
501  RLVAVPSKRV  LCPL*
```

FIG. 4A Aspen (*P. tremuloides*) PtAldOMT cDNA sequence

GenBank accession number: X62096 (SEQ ID NO: 5).

```
   1  tcacttcctt tccttacacc ttcttcaacc ttttgtttcc ttgtagaatt
  51  caatctcgat caagatgggt tcaacaggtg aaactcagat gactccaact
 101  caggtatcag atgaagaggc acacctcttt gccatgcaac tagccagtgc
 151  ttcagttcta ccaatgatcc tcaaaacagc cattgaactc gaccttcttg
 201  aaatcatggc taaagctggc cctggtgctt cttgtccac atctgagata
 251  gcttctcacc tccctaccaa aaaccctgat gcgcctgtca tgttagaccg
 301  tatcctgcgc ctcctggcta gctactccat tcttacctgc tctctgaaag
 351  atcttcctga tgggaaggtt gagagactgt atggcctcgc tcctgtttgt
 401  aaattcttga ccaagaacga ggacggtgtc tctgtcagcc ctctctgtct
 451  catgaaccag gacaaggtcc tcatggaaag ctggtattat ttgaaagatg
 501  caattcttga tggaggaatt ccatttaaca aggcctatgg gatgactgca
 551  tttgaatatc atggcacgga tccaagattc aacaaggtct caacaaggg
 601  aatgtctgac cactctacca ttaccatgaa gaagattctt gagacctaca
 651  aaggctttga aggcctcacg tccttggtgg atgttggtgg tgggactgga
 701  gccgtcgtta acaccatcgt ctctaaatac ccttcaatca gggcattaa
 751  cttcgatctg ccccacgtca ttgaggatgc cccatcttat cccggagtgg
 801  agcatgttgg tggcgacatg tttgttagtg tgcccaaagc agatgccgtt
 851  ttcatgaagt ggatatgcca tgattggagc gacgcccact gcttaaaatt
 901  cttgaagaat tgctatgacg cgttgccgga aaacggcaag gtgatacttg
 951  ttgagtgcat tcttcccgtg gctcctgaca caagccttgc caccaaggga
1001  gtcgtgcacg ttgatgtcat catgctggcg cacaacccccg gtgggaaaga
1051  gaggaccgag aaggaatttg agggcttagc taagggagct ggcttccaag
1101  gttttgaagt aatgtgctgt gcattcaaca cacatgtcat tgaattccgc
```

FIG. 4A (Continued)

```
1151  aagaaggcct aaggcccatg tccaagctcc aagttacttg gggttttgca
1201  gacaacgttg ctgctgtctc tgcgtttgat gtttctgatt gctttttttt
1251  atacgaggag tagctatctc ttatgaaaca tgtaaggata agattgcgtt
1301  ttgtatgcct gattttctca ataacttca  ctgcctccct caaaattctt
1351  aatacatgtg aaaagatttc ctattggcct tctgcttcaa acagtaaaga
1401  cttctgtaac ggaaaagaaa gcaattcatg atgtatgtat cttgcaagat
1451  tatgagtatt gttctaagca ttaagtgatt gttcaaaaaa aaaaaaaaaa
1501  aaa
```

FIG. 4B Aspen (*P. tremuloides*) PtAldOMT protein sequence

GenBank accession number: X62096 (SEQ ID NO: 6).

```
  1  MGSTGETQMT PTQVSDEEAH LFAMQLASAS VLPMILKTAI ELDLLEIMAK
 51  AGPGAFLSTS EIASHLPTKN PDAPVMLDRI LRLLASYSIL TCSLKDLPDG
101  KVERLYGLAP VCKFLTKNED GVSVSPLCLM NQDKVLMESW YYLKDAILDG
151  GIPFNKAYGM TAFEYHGTDP RFNKVFNKGM SDHSTITMKK ILETYKGFEG
201  LTSLVDVGGG TGAVVNTIVS KYPSIKGINF DLPHVIEDAP SYPGVEHVGG
251  DMFVSVPKAD AVFMKWICHD WSDAHCLKFL KNCYDALPEN GKVILVECIL
301  PVAPDTSLAT KGVVHVDVIM LAHNPGGKER TEKEFEGLAK GAGFQGFEVM
351  CCAFNTHVIE FRKKA
```

FIG. 5A 4 CL polynucleotide DNA sequence (SEQ ID NO: 7).

```
ccctcgcgaa actccgaaaa cagagagcac ctaaaactca ccatctctcc ctctgcatct    60
ttagcccgca atggacgcca ca atg aat cca caa gaa ttc atc ttt cgc tca   112
aaa tta cca gac atc tac atc ccg aaa aac ctt ccc ctg cat tca tac    160 gtt ctt gag aac ttg tct aaa cat tca tca aaa cct tgc ctg ata aat    208
ggc gcg aat gga gat gtc tac acc tat gct gat gtt gag ctc aca gca    256
aga aga gtt gct tct ggt ctg aac aag att ggt att caa caa ggt gac    304 gtg atc atg ctc ttc cta cca agt tca cct gaa ttc gtg ctt gct ttc    352
cta ggc gct tca cac aga ggt gcc atg atc act gct gcc aat cct ttc    400
tcc acc cct gca gag cta gca aaa cat gcc aag gcc tcg aga gca aag    448 ctt ctg ata aca cag gct tgt tac tac gag aag gtt aaa gat ttt gcc    496
cga gaa agt gat gtt aag gtc atg tgc gtg gac tct gcc ccg gac ggt    544
gct tca ctt ttc aga gct cac aca cag gca gac gaa aat gaa gtg cct    592 cag gtc gac att agt cct gat gat gtc gta gca ttg cct tat tca tca    640
ggg act aca ggg ttg cca aaa ggg gtc atg tta acg cac aaa ggg cta    688
ata acc agt gtg gct caa cag gta gat gga caa tcc taa ctg tat       736 ttt cac agt gaa gat gtg att ctg tgt gtg ctt cct atg ttc cat atc    784
tat gct ctg aat tca atg atg ctc tgt ggt ctg aga gtt ggt gcc tcg    832
att ttg ata atg cca aag ttt gag att ggt tct ttg ctg gga ttg att    880 gag aag tac aag gta tct ata gca cca gtt gtt cca cct gtg atg atg    928
gca att gct aag tca cct gat ctt gac aag cat gac ctg tct tct ttg    976
agg atg ata aaa tct gga ggg gct cca ttg ggc aag gaa ctt gaa gat   1024 act gtc aga gct aag ttt cct cag gct aga ctt ggt cag gga tat gga   1072
atg acc gag gca gga cct gtt cta gca atg tgc ttg gca ttt gcc aag   1120
gaa cca ttc gac ata aaa cca ggt gca tgt gga act gta gtc agg aat   1168 gca gag atg aag att gtt gac cca gaa aca ggg gtc tct cta ccg agg   1216
aac cag cct ggt gag atc tgc atc cgg ggt gat cag atc atg aaa gga   1264
tat ctt aat gac ccc gag gca acc tca aga aca ata gac aaa gaa gga   1312 tgg ctg cac aca ggc gat atc ggc tac att gat gat gat gat gag ctt   1360
ttc atc gtt gac aga ttg aag gaa ttg atc aag tat aaa ggg ttt cag   1408
gtt gct cct act gaa ctc gaa gct ttg tta ata gcc cat cca gag ata   1456 tcc gat gct gct gta gta gga ttg aaa gat gag gat gcg gga gaa gtt   1504
cct gtt gca ttt gta gtg aaa tca gaa aag tct cag gcc acc gaa gat   1552
gaa att aag cag tat att tca aaa cag gtg atc ttc tac aag aga ata   1600 aaa cga gtt ttc ttc att gaa gca att ccc aag gca cca tca ggc aag   1648
atc ctg agg aag aat ctg aaa gag aag ttg cca ggc ata taactgaaga    1697
tgttactgaa catttaaccc tctgtcttat ttctttaata cttgcgaatc attgtagtgt  1757
tgaaccaagc atgcttggaa aagacacgta cccaacgtaa gacagttact gttcctagta  1817
tacaagctct ttaatgttcg ttttgaactt gggaaaacat aagttctcct gtcgccatat  1877
ggagtaattc aattgaatat tttggtttct ttaatgat                          1915
```

FIG. 5B 4CL Aspen (*P. tremuloides*) amino acid sequence (SEQ ID NO: 10).

```
                        Met Asn Pro Gln Glu Phe Ile Phe Arg Ser
                         1               5                   10
Lys Leu Pro Asp Ile Tyr Ile Pro Lys Asn Leu Pro Leu His Ser Tyr
                15                  20                  25
Val Leu Glu Asn Leu Ser Lys His Ser Ser Lys Pro Cys Leu Ile Asn
            30                  35                  40
Gly Ala Asn Gly Asp Val Tyr Thr Tyr Ala Asp Val Glu Leu Thr Ala
        45                  50                  55
Arg Arg Val Ala Ser Gly Leu Asn Lys Ile Gly Ile Gln Gln Gly Asp
    60                  65                  70
Val Ile Met Leu Phe Leu Pro Ser Ser Pro Glu Phe Val Leu Ala Phe
75                  80                  85                  90
Leu Gly Ala Ser His Arg Gly Ala Met Ile Thr Ala Ala Asn Pro Phe
                95                  100                 105
Ser Thr Pro Ala Glu Leu Ala Lys His Ala Lys Ala Ser Arg Ala Lys
            110                 115                 120
Leu Leu Ile Thr Gln Ala Cys Tyr Tyr Glu Lys Val Lys Asp Phe Ala
        125                 130                 135
Arg Glu Ser Asp Val Lys Val Met Cys Val Asp Ser Ala Pro Asp Gly
    140                 145                 150
Ala Ser Leu Phe Arg Ala His Thr Gln Ala Asp Glu Asn Glu Val Pro
155                 160                 165                 170
Gln Val Asp Ile Ser Pro Asp Asp Val Val Ala Leu Pro Tyr Ser Ser
                175                 180                 185
Gly Thr Thr Gly Leu Pro Lys Gly Val Met Leu Thr His Lys Gly Leu
            190                 195                 200
Ile Thr Ser Val Ala Gln Gln Val Asp Gly Asp Asn Pro Asn Leu Tyr
        205                 210                 215
Phe His Ser Glu Asp Val Ile Leu Cys Val Leu Pro Met Phe His Ile
    220                 225                 230
Tyr Ala Leu Asn Ser Met Met Leu Cys Gly Leu Arg Val Gly Ala Ser
235                 240                 245                 250
Ile Leu Ile Met Pro Lys Phe Glu Ile Gly Ser Leu Leu Gly Leu Ile
                255                 260                 265
Glu Lys Tyr Lys Val Ser Ile Ala Pro Val Val Pro Pro Val Met Met
            270                 275                 280
Ala Ile Ala Lys Ser Pro Asp Leu Asp Lys His Asp Leu Ser Ser Leu
        285                 290                 295
Arg Met Ile Lys Ser Gly Gly Ala Pro Leu Gly Lys Glu Leu Glu Asp
    300                 305                 310
Thr Val Arg Ala Lys Phe Pro Gln Ala Arg Leu Gly Gln Gly Tyr Gly
315                 320                 325                 330
Met Thr Glu Ala Gly Pro Val Leu Ala Met Cys Leu Ala Phe Ala Lys
                335                 340                 345
Glu Pro Phe Asp Ile Lys Pro Gly Ala Cys Gly Thr Val Val Arg Asn
            350                 355                 360
Ala Glu Met Lys Ile Val Asp Pro Glu Thr Gly Val Ser Leu Pro Arg
        365                 370                 375
Asn Gln Pro Gly Glu Ile Cys Ile Arg Gly Asp Gln Ile Met Lys Gly
    380                 385                 390
Tyr Leu Asn Asp Pro Glu Ala Thr Ser Arg Thr Ile Asp Lys Glu Gly
395                 400                 405                 410
Trp Leu His Thr Gly Asp Ile Gly Tyr Ile Asp Asp Asp Asp Glu Leu
                415                 420                 425
Phe Ile Val Asp Arg Leu Lys Glu Leu Ile Lys Tyr Lys Gly Phe Gln
            430                 435                 440
Val Ala Pro Thr Glu Leu Glu Ala Leu Leu Ile Ala His Pro Glu Ile
        445                 450                 455
Ser Asp Ala Ala Val Val Gly Leu Lys Asp Glu Asp Ala Gly Glu Val
    460                 465                 470
Pro Val Ala Phe Val Val Lys Ser Glu Lys Ser Gln Ala Thr Glu Asp
475                 480                 485                 490
```

FIG. 5B (Continued)

```
Glu Ile Lys Gln Tyr Ile Ser Lys Gln Val Ile Phe Tyr Lys Arg Ile
            495                 500                 505
Lys Arg Val Phe Phe Ile Glu Ala Ile Pro Lys Ala Pro Ser Gly Lys
            510                 515                 520
Ile Leu Arg Lys Asn Leu Lys Glu Lys Leu Pro Gly Ile
            525                 530                 535
```

FIG. 6A Aspen (*P. tremuloides*) PtCAD protein sequence

GenBank accession number: AF217957 (SEQ ID NO: 9).

```
  1  MGSLETERKI VGWAATDSTG HLAPYTYSLR DTGPEDVLIK VISCGICHTD
 51  IHQIKNDLGM SHYPMVPGHE VVGEVVEVGS DVTKFKAGDV VGVGVIVGSC
101  KNCHPCKSEL EQYCNKKIWS YNDVYTDGKP TQGGFAESMV VDQKFVVRIP
151  DGMSPEQAAP LLCAGLTVYS PLKHFGLKQS GLRGGILGLG GVGHMGVKIA
201  KAMGHHVTVI SSSDKKREEA MEHLGADEYL VSSDVESMQK AADQLDYIID
251  TVPVVHPLEP YLSLLKLDGK LILMGVINTP LQFVSPMVML GRKSITGSFI
301  GSMKETEEML EFCKEKGLAS MIEVIKMDYI NTAFERLEKN DVRYRFVVDV
351  AGSKLIP*
```

FIG. 6B Aspen (*P. tremuloides*) PtCAD cDNA sequence

GenBank accession number: AF217957 (SEQ ID NO: 8).

```
   1  AAACTCCATC CCTCTCTCTT AGCCTCGTTG TTTCAAGAAA ATGGGTAGCC
  51  TTGAAACAGA GAGAAAAATT GTAGGATGGG CAGCAACAGA CTCAACTGGG
 101  CATCTCGCTC CTTACACCTA TAGTCTCAGA GATACGGGGC CAGAAGATGT
 151  TCTTATCAAG GTTATCAGCT GTGGAATTTG CCATACCGAT ATCCACCAAA
 201  TCAAAAATGA TCTTGGCATG TCACACTATC CTATGGTCCC TGGCCATGAA
 251  GTGGTTGGTG AGGTTGTTGA GGTGGGATCA GATGTGACAA AGTTCAAAGC
 301  TGGAGATGTT GTTGGTGTTG GAGTCATCGT TGGAAGCTGC AAGAATTGTC
 351  ATCCATGCAA ATCAGAGCTT GAGCAATACT GCAACAAGAA AATCTGGTCT
 401  TACAATGATG TCTACACTGA TGGCAAACCC ACCCAAGGAG GCTTTGCTGA
 451  ATCCATGGTT GTCGATCAAA AGTTTGTGGT GAGAATTCCT GATGGGATGT
 501  CACCAGAACA AGCAGCGCCG CTGTTGTGCG CTGGATTGAC AGTTTACAGC
 551  CCACTCAAAC ACTTTGGACT GAAACAGAGT GGGCTAAGAG GAGGGATTTT
 601  AGGACTTGGA GGAGTAGGGC ACATGGGGGT GAAGATAGCA AAGGCAATGG
 651  GACACCATGT AACTGTGATT AGTTCTTCTG ACAAGAAGCG GGAGGAGGCT
 701  ATGGAACATC TTGGTGCTGA TGAATACCTG GTCAGCTCGG ATGTGGAAAG
 751  CATGCAAAAA GCTGCTGATC AACTTGACTA TATCATCGAT ACTGTGCCTG
 801  TGGTTCACCC TCTCGAGCCT TACCTTTCTC TATTGAAACT TGATGGCAAG
 851  CTGATCTTGA TGGGTGTTAT TAATACCCCA TTGCAGTTTG TTTCGCCAAT
 901  GGTTATGCTT GGGAGAAAGT CGATCACCGG GAGCTTCATA GGGAGCATGA
 951  AGGAGACAGA GGAGATGCTT GAGTTCTGCA AGGAAAGGG ATTGGCCTCC
1001  ATGATTGAAG TGATCAAAAT GGATTATATC AACACAGCAT TCGAGAGGCT
1051  TGAGAAAAAT GATGTGAGAT ATAGATTCGT TGTCGATGTT GCTGGTAGCA
1101  AGCTTATTCC CTGAACGACA ATACCATTCA TATTCGAAAA AACGCGATAT
1151  ACATTGATAC CTGTTTCAGA CTTGACTTTA TTTTCGAGTG ATGTGTTTTG
```

FIG. 6B (Continued)

```
1201  TGGTTCAAAT GTGACAGTTT GTCTTTGCTT TTAAAATAAA GAAAAAGTTG

1251  AGTTGTTTTT TTATTTTCAT TAATGGGCAT GCGTTACCTT GTAATTGAAT

1301  GCGCTGCATC TGGTGATCTG TCCCATAAAC TAATCTCTTG TGGCAATGAA

1351  AGATGACGAA CTTTCTGAAA AAAAAAAAAA AAAAAAAAA AAAAA
```

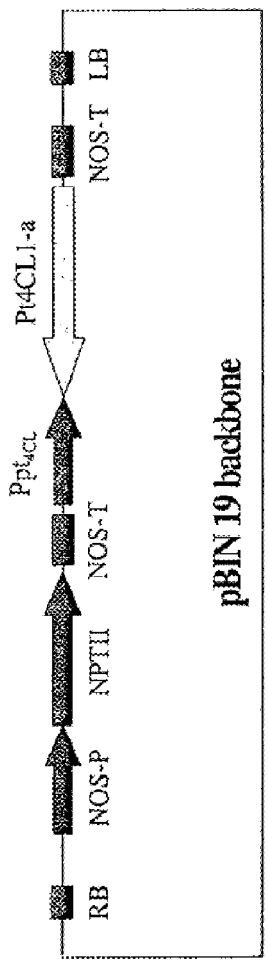
Fig. 7. pBKPpt_{4CL} Pt4CL1-a construct
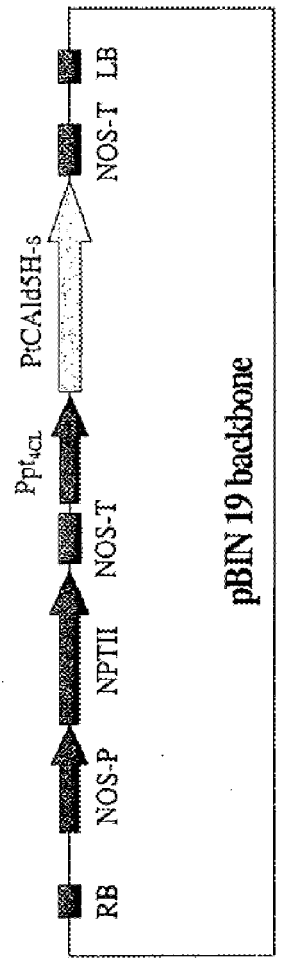
Fig. 8. pBKPpt_{4CL} PtCAld5H-s construct FIG. 9-1 The alignment of plant AldOMT protein sequences

```
     1                                                            50
1    ~~~~~~~~~~ ~~~~~~~~MG STG..ETQMT PTQVSDEEAH LFAMQLASAS
2    ~~~~~~~~~~ ~~~~~~~~MG STG..ETQMT PTQVSDEEAH LFAMQLASAS
3    ~~~~~~~~~~ ~~~~~~~~MG STG..ETQMT PTQVSDEEAN LFAMQLASAS
4    ~~~~~~~~~~ ~~~~~~~~MG STG..ETQMT PTHVSDEEAN LFAMQLASAS
5    ~~~~~~~~~~ ~~~~~~~~MG STG..ETQIT PTHISDEEAN LFAMQLASAS
6    ~~~~~~~~~~ ~~~~~~~~MG STG.SETQMT PTQVSDEEAN LFAMQLASAS
7    ~~~~~~~~~~ ~~~~~~~~MG STGNAETQLT PTHVSDEEAN LFAMQLASAS
8    ~~~~~~~~~~ ~~~~~~~~MG STSETKMSPS EAAAAEEEAF VFAMQLTSAS
9    ~~~~~~~~~~ ~~~~~~~~MG ST..AETQLT PVQVTDDEAA LFAMQLASAS
10   ~~~~~~~~~~ ~~~~~~~~MG ST..SESQSN SLTHTEDEAF LFAMQLCSAS
11   MESTLAFNSG SNSMNQSFSS SAEFNSPVPE TIPKSEEDTF VFATLLTSAS 51                                                           100
1    VLPMILKTAI ELDLLEIMAK A...GPGAFL STSEIASHLP TKNPDAPVML
2    VLPMILKTAI ELDLLEIMAK A...GPGAFL STSEIASHLP TKNPDAPVML
3    VLPMVLKAAI ELDLLEIMAK A...GPGVFL SPTDIASQLP TKNPDAPVML
4    VLPMVLKAAI ELDLLEIMAK A...GPGSFL SPSDLASQLP TKNPEAPVML
5    VLPMILKSAL ELDLLEIIAK A...GPGAQI SPIEIASQLP TTNPDAPVML
6    VLPMVLKAAI ELDLLEIMAK A...GPGAFL SPGEVAAQLP TQNPEAPVML
7    VLPMVLKAAI ELDVLEIMAK SIPHGSGAYI SPAEIAAQLP TTNPDAPVML
8    VLPMVLKSAI ELDVLEIMAK A...GPGAHI STSDIASKLP TKNPDAAVML
9    VLPMALKSAL ELDLLEIMAK .....NGSPM SPTEIASKLP TKNPEAPVML
10   VLPMVLKSAV ELDLLELMAK A...GPGAAI SPSELAAQLS TQNPEAPVML
11   VLPMALKSAL ELDLLEIIAK A...GPGAFV STSEIAAKIT KRNPKAPVML 101                                                          150
1    DRILRLLASY SILTCSLKDL PDGKVERLYG LAPVCKFLTK NEDGVSVSPL
2    DRILRLLASY SILTCSLKDH PDGKVERLYG LAPVCKFLTK NEDGVSVSPL
3    DRMLRLLASY SILTYSLRTL ADGKVERLYG LGPVCKFLTK NEEGVSIAPL
4    DRMLRLLASY SILTCSLRTL PDGKVERLYC LGPVCKFLTK NEDGVSIAAL
5    DRMLRLLACY IILTCSVRTQ QDGKVQRLYG LATVAKYLVK NEDGVSISAL
6    DRIFRLLASY SVLTCTLRNL PDGKVERLYG LAPVCKFLVK NEDGVSIAAL
7    DRVLRLLASY SVVTCSLREL PDGKVERLYG LAPVCKFLTK NEDGVSLAPL
8    DRMLRLLASY SVLTCSLRTL PDGKIERLYG LAPVCKFLTR NDDGVSIAAL
9    DRILRLLTSY SVLTCSNRKL SGDGVERIYG LGPVCKYLTK NEDGVSIAAL
10   DRMLRLLASY SVLNCTLRTL PDSSVERLYS LAPVCKYLTK NADGVSVAPL
11   DRILRLLATY DVVKCSLRDS PDGGVERLYG LGPVCKYFTT NEDGVSVAPL 151                                                          200
1    CLMNQDKVLM ES.WYYLKDA ILDGGIPFNK AYGMTAFEYH GTDPRFNKVF
2    CLMNQDKVLM ES.WYYLKDA ILDGGIPFNK AYGMTAFEYH GTDPRFNKVF
3    CLMNQDKVLL ES.WYHLKDA VLEGGIPFNK AYGMTAFEYH GTDPRFNKVF
4    CLMNQDKVLV ES.WYHLKDA VLDGGIPFNK AYGMTAFDYH GTDPRFNKVF
5    NLMNQDKVLM ES.WYHLKDA VLDGGIPFNK AYGMTAFEYH GTDPRFNKVF
6    NLMNQDKILM ES.WYYLKDA VLEGGIPFNK AYGMTAFEYH GTDPRFNKIF
```

FIG. 9-2

```
7  CLMNQDKVLM ES.WYYLKDA ILDGGIPFNK AYGMTAFEYH GTDPRFNKVF
8  SLMNQDKVLM ES.WYHLTEA VLEGGIPFNK AYGMTAFEYH GTDPRFNTVF
9  CLMNQDKVLM ES.WYHLKDA ILDGGIPFNK AYGMSAFEYH GTDPRFNKVF
10 LLMNQDKVLM ES.WYHLKDA VLDGGIPFNK AYGMTAFEYH GTDPRFNKVF
11 LLMNQDKVPM QSKRYHLKDA VLDGGIPFNK AYGMTDFEYH GTEPRFNKVF 201                                                250
1  NKGMSDHSTI TMKKILETYK GFEGLTSLVD VGGGTGAVVN TIVSKYPSIK
2  NKGMSDHSTI TMKKILETYK GFEGLTSLVD VGGGTGAVVN TIVSKYPSIK
3  NRGMADHSTI TMKKILETYK GFEGLTSVVD VGGGTGAVLN MIVSKYPSIK
4  NKGMADHSTI TMKKILETYK GFEGLKSIVD VGGGTGAVVN MIVSKYPSIK
5  NKGMSDHSTI TMKKILETYT GFEGLKSLVD VGGGTGAVIN TIVSKYPTIK
6  NRGMSDHSTI TMKKILETYK GFEGLETVVD VGGGTGAVLS MIVAKYPSMK
7  NRGMSDHSTI TMKKIFEMYT GFEALNTIVD VGGGTGAVLS MIVAKYPSIK
8  NNGMSNHSTI TMKKILETYK GFEGLGSVVD VGGGTGAHLN MIIAKYPMIK
9  NNGMSNHSTI TMKKILETYK GFEGLTSLVD VGGGIGATLK MIVSKYPNLK
10 NRGMSDHSTM SMKKILEDYK GFEGLNSIVD VGGGTGATVN MIVSKYPSIK
11 NNGVSGHPTI TMKKILEAYK GFEGLTSIVD VGGGTGATLN MIISKYPTIK
                                    motif I 251                                                300
1  GINFDLPHVI EDAPSYPGVE HVGGDMFVSV PKADAVFMKW ICHDWSDAHC
2  GINFDLPHVI EDAPSYPGVE HVGGDMFVSV PKADAVFMKW ICHDWSDAHC
3  GINFDLPHVI EDAPQYPGVE HVGGDMFVSV PKGDAIFMKW ICHDWSDEHC
4  GINFDLPHVI EDAPQYPGVQ HVGGDMFVSV PKGNAIFMKW ICHDWSDEHC
5  GINFDLPHVI EDAPSYPGVE HVGGDMFVSI PKADAVFMKW ICHDWSDEHC
6  GINFDLPHVI EDAPPLPGVK HVGGDMFVSV PKGDAIFMKW ICHDWSDDHC
7  GINFDLPHVI EDAPIYPGVE HVGGDMFVSV PKGDAIFMKW ICHDWSDEHC
8  GINFDLPHVI EEAPSYPGVE HVGGDMFVSV PKGDAIFMKW ICHDWSDEHC
9  GINFNLPHVI EDAPSHPGIE HVGGDMFVSV PKGDAIFMKW ICHDWSDEHC
10 GINFDLPHVI GDAPTYPGVE HVGGDMFASV PKADAIFMKW ICHDWSDEHC
11 GINFDLPHVI DDAPSYPGVE HVGGDMFVSV PKGDAIFMKW MCYEWDDAHC
                                    motifII 301                                                350
1  LKFLKNCYDA LPENGKVILV ECILPVAPDT SLATKGVVHV DVIMLAHNPG
2  LKFLKNCYDA LPENGKVILV ECILPVAPDT SLATKGVVHI DVIMLAHNPG
3  LKFLKNCYAA LPDNGKVILG ECILPVAPDS SLATKGVVHI DVIMLAHNPG
4  IKFLKNCYAA LPDDGKVILA ECILPVAPDT SLATKGVVHM DVIMLAHNPG
5  LKFLKNCYEA LPDNGKVIVA ECILPVAPDS SLATKGVVHI DVIMLAHNPG
6  AKFLKNCYDA LPNIGKVIVA ECVLPVYPDT SLATKNVIHI DCIMLAHNPG
7  LKFLKNCYAA LPEHGKVIVA ECILPLSPDP SLATKGVIHI DAIMLAHNPG
8  LKFLKKCYEA LPTNGKVILA ECILPVAPDA SLPTKAVVHI DVIMLAHNPG
9  VKFLKNCYES LPEDGKVILA ECILPETPDS SLSTKQVVHV DCIMLAHNPG
```

FIG. 9-3

```
10  LKFLKNCYEA  LPANGKVIIA  ECILPEAPDT  SLATKNTVHV  DIVMLAHNPG
11  LKFLENCYQA  LPDNGKVIVA  ECILPVVPDT  SLATKSAVHI  DVIMLAYNTG
                motif III 351                                             389
1   GKERTEKEFE  GLAKGAGFQG  FEVMCCAFNT  HVIEFRKKA
2   GKERTEKEFE  GLAKGAGFQG  FEVMCCAFNT  HVIELRKN~
3   GKERTEQEFQ  ALAKGAGFQG  FNVACSAFNT  YVIEFLKKN
4   GKERTEQEFE  ALAKGSGFQG  IRVCCDAFNT  YVIEFLKKI
5   GKERTQKEFE  DLAKGAGFQG  FKVHCNAFNT  YIMEFLKKV
6   GKERTQKEFE  TLAKGAGFQG  FQVMCCAFGT  HVMEFLKTA
7   GKERTEKEFE  ALAIGAGFKG  FKVACCAFNT  YVMEFLKTA
8   GKERTEKEFE  ALAKGAGFEG  FRVALCAYNT  WIIEFLKKI
9   GKERTEKEFE  ALAKASGFKG  IKVVCDAFGV  NLIELLKKL
10  GKERTEKEFE  ALAKGAGFTG  FARLVALTTL  GSWNSTSN~
11  GKARTEKEFE  ALAKGAGFQG  FKVVCCAFNS  WIMEFCKTA
```

Plant AldOMTs from

1) Aspen, X62096 (SEQ ID NO: 6)
2) Poplar, M73431 (SEQ ID NO: 15)
3) Almond, X83217 (SEQ ID NO: 16)
4) Strawberry, AF220491 (SEQ ID NO: 17)
5) Alfalfa, M63853 (SEQ ID NO: 18)
6) Eucalyptus, X74814 (SEQ ID NO: 19)
7) Clarkia breweri, AF006009 (SEQ ID NO: 20)
8) Sweetgum, AF139533 (SEQ ID NO: 21)
9) Arabidopsis, U70424 (SEQ ID NO: 22)
10) Tobacco, X74452 (SEQ ID NO: 23)
11) Vitis vinifera, AF239740 (SEQ ID NO: 24)

FIG. 10-1 The alignment of full length plant CAD protein sequences available in the GenBank database

```
        1                                                    50
 1  MGSLE.TEKT VTGYAARDSS GHLSPYTYNL RKKGPEDVIV KVIYCGICHS
 2  MGSLE.SEKT VTGYAARDSS GHLSPYTYNL RKKGPEDVIV KVIYCGICHS
 3  MGSLE.SEKT VTGYAARDSS GHLSPYTYNL RKKGPEDVIV KVIYCGICHS
 4  MGSLE.SERT VTGYAARDSS GHLSPYTYTL RNKGPEDVIV RVIYCGICHS
 5  MGSL.ASERK VVGWAARDAT GHLSPYSYTL RNTGPEDVVV KVLYCGICHT
 6  MGSL.ASERK VVGWAARDAT GHLSPYSYTL RNTGPEDVVV KVLYCGICHT
 7  MGSL.ASERK VVGWAARDAT GHLAPYTYTL RSTGPEDVVV KVLYCGICHT
 8  MGSIEAAERT TVGLAAKDPS GILTPYTYTL RNTGPDDVYI KIHYCGVCHS
 9  MGSIEAAERT TVGLAAKDPS GILTPYTYTL RNTGPDDVYI KIHYCGVCHS
10  MGSLEK.ERT TTGWAARDPS GVLSPYTYSL RNTGPEDLYI KVLSCGICHS
11  MGSLEK.ERT TTGWAARDPS GVLSPYTYSL RNTGPEDLYI KVLSCGVCHS
12  MGGLEV.EKT TIGWAARDPS GVLSPYTYTL RNTGPEDVEV KVLYCGLCHT
13  MGSLDV.EKS AIGWAARDPS GLLSPYTYTL RNTGPEDVQV KVLYCGLCHS
14  MGSLET.ERK IVGWAATDST GHLAPYTYSL RDTGPEDVLI KVISCGICHT
15  MGSLET.ERK IVGWAATDST GHLAPYTYSL RDTGPEDVFI KVISCGVCHT
16  MGSLEA.ERK TTGWAARDPS GVLSPYTYTL RETGPEDVFI KIIYCGICHT 51                                                  100
 1  DLVQMRNEMG MSHYPMVPGH EVVGIVTEIG SEVKKFKVGE HVGVGCIVGS
 2  DLVQMRNEMG MSHYPMVPGH EVVGIVTEIG SEVKKFKVGE HVGVGCIVGS
 3  DLVQMRNEMG MSHYPMVPGH EVVGIVTEIG SEVKKFKVGE HVGVGCIVGS
 4  DLVQMHNEMG MSNYPMVPGH EVVGVVTEIG SEVKKFKVGE HVGVGCIVGS
 5  DIHQAKNHLG ASKYPMVPGH EVVGEVVEVG PEVAKYGVGD VVGVGVIVGC
 6  DIHQAKNHLG ASKYPMVPGH EVVGEVVEVG PEVAKYGVGD VVGVGVIVGC
 7  DIHQAKNHLG ASKYPMVPGH EVVGEVVEVG PEVTKYGVGD VVGVGVIVGC
 8  DLHQIKNDLG MSNYPMVPGH EVVGEVLEVG SNVTRFKVGE IVGVGLLVGC
 9  DLHQIKNDLG MSNYPMVPGH EVVGEVLEVG SNVTRFKVGE IVGVGLLVGC
10  DIHQIKNDLG MSHYPMVPGH EVVGEVLEVG SEVTKYRVGD RVGTGIVVGC
11  DIHQIKNDLG MSHYPMVPGH EVVGEVLEVG SEVTKYRVGD RVGTGIVVGC
12  DLHQVKNDLG MSNYPLVPGH EVVGEVVEVG PDVSKFKVGD TVGVGLLVGS
13  DLHQVKNDLG MSNYPLVPGH EVVGKVVEVG ADVSKFKVGD TVGVGLLVGS
14  DIHQIKNDLG MSHYPMVPGH EVVGEVVEVG SDVTKFKAGD VVGVGVIVGS
15  DIHQIKNDLG MSHYPMVPGH EVVGEVVEVG SDVTRFKVGD VVGVGVIVGS
16  DIHQIKNDLG ASNYPMVPGH EVVGEVVEVG SDVTKFKVGD CVGDGTIVGC
                             Zn1                Zn2

101                                                 150
 1  CRSCGNCNQS MEQYCSKRIW TYNDVNHDGT PTQGGFASSM VVDQMFVVRI
 2  CRSCGNCNQS MEQYCSKRIW TYNDVNHDGT PTQGGFASSM VVDQMFVVRI
 3  CRSCGNCNQS MEQYCSKRIW TYNDVNHDGT PTQGGFASSM VVDQMFVVRI
 4  CRSCSNCNGS MEQYCSKRIW TYNDVNHDGT PTQGGFASSM VVDQMFVVRI
 5  CRECSPCKAN VEQYCNKKIW SYNDVYTDGR PTQGGFASTM VVDQKFVVKI
 6  CRECSPCKAN VEQYCNKKIW SYNDVYTDGR PTQGGFASTM VVDQKFVVKI
 7  CRECKPCKAN VEQYCNKKIW SYNDVYTDGR PTQGGFASTM VVDQKFVMKI
 8  CKSCRACDSE IEQYCNKKIW SYNDVYTDGK ITQGGFAEST VVEQKFVVKI
 9  CKSCRACDSE IEQYCNKKIW SYNDVYTDGK ITQGGFAEST VVEQKFVVKI
```

FIG. 10-2

```
        10  CRSCSPCNSD  QEQYCNKKIW  NYNDVYTDGK  PTQGGFAGEI  VVGERFVVKI
        11  CRSCSPCNSD  QEQYCNKKIW  NYNDVYTDGK  PTQGGFAGEI  VVGERFVVKI
        12  CRNCGPCKRD  IEQYCNKKIW  NCNDVYTDGK  PTQGGFAKSM  VVDQKFVVKI
        13  CRNCGPCKRE  IEQYCNKKIW  NCNDVYTDGK  PTQGGFANSM  VVDQNFVVKI
        14  CKNCHPCKSE  LEQYCNKKIW  SYNDVYTDGK  PTQGGFAESM  VVDQKFVVRI
        15  CKNCHPCKSE  IEQYCNKKIW  SYNDVYTDGK  PTQGGFAESM  VVHQKFVVRI
        16  CKTCRPCKAD  VEQYCNKKIW  SYNDVYTDGK  PTQGGFSGHM  VVDQKFVVKI
            ‾‾‾‾‾‾‾‾‾‾  ‾‾‾‾
            Zn2

151                                                    200
        1   PENLPLEQAA  PLLCAGVTVF  SPMKHFAMTE  .PGKKCGILG  LGGVGHMGVK
        2   PENLPLEQAA  PLLCAGVTVF  SPMKHFAMTE  .PGKKCGILG  LGGVGHMGVK
        3   PENLPLEQAA  PLLCAGVTVF  SPMKHFAMTE  .PGKKCGILG  LGGVGHLGVK
        4   PENLPLEQAA  PLLCAGVTVY  SPMKHFGMTE  .PGKKCGILG  LGGVGHMGVK
        5   PAGLAPEQAA  PLLCAGVTVY  SPLKHFGL.T  TPGLRGGILG  LGGVGHMGVK
        6   PAGLAPEQAA  PLLCAGVTVY  SPLKHFGL.T  NPGLRGGILG  LGGVGHMGVK
        7   PAGLAPEQAA  PLLCAGVTVY  SPLKAFGL.T  TPGLRGAILG  LGGVGHMGVK
        8   PEGLAPEQVA  PLLCAGVTVY  SPLSHFGLK.  TPGLRGGILG  LGGVGHMGVK
        9   PEGLAPEQVA  PLLCAGVTVY  SPLSHFGLK.  TPGLRGGILG  LGGVGHMGVK
        10  PDGLESEQAA  PLMCAGVTVY  SPLVRFGLKQ  .SGLRGGILG  LGGVGHMGVK
        11  PDGLESEQAA  PLMCAGVTVY  SPLVRFGLKQ  .SGLRGGILG  LGGVGHMGVK
        12  PEGMAPEQAA  PLLCAGITVY  SPLNHFGFKQ  .SGLRGGILG  LGGVGHMGVK
        13  PEGMAPEQAA  PLLCAGITVY  SPFNHFGFNQ  .SGFRGGILG  LGGVGHMGVK
        14  PDGMSPEQAA  PLLCAGLTVY  SPLKHFGLKQ  .SGLRGGILG  LGGVGHMGVK
        15  PDGMSPEQAA  PLLCAGLTVY  SPLKHFGLKQ  .SGLRGGILG  LGGVGHMGVK
        16  PDGMAPEQAA  PLLCAGVTVY  SPLTHFGLKE  ISGLRGGILG  LGGVGHMGVK
                                                ‾‾‾‾
                                                NADP 201                                                    250
        1   IAKAFGLHVT  VISSSDKKKE  EAMEVLGADA  YLVSKDTEKM  MEAAESLDYI
        2   IAKAFGLHVT  VISSSDKKKE  EAMEVLGADA  YLVSKDTEKM  MEAAESLDYI
        3   IAKAFGLHVT  VISSSDKKKE  EAMEVLGADA  YLVSKDTEKM  MEAAESLDYI
        4   IAKAFGLHVT  VISSSDKKKE  EALEVLGADA  YLVSKDAEKM  QEAAESLDYI
        5   VAKAMGHHVT  VISSSSKKRA  EAMDHLGADA  YLVSSDAAAM  GPAADSLDYI
        6   VAKAMGHHVT  VISSSSKKRA  EAMDHLGADA  YLVSSDAAAM  AAAADSLDYI
        7   VAKAMGHHVT  VISSSSKKRA  EAMDHLGADA  YLVSSDAAAM  AAAADSLDYI
        8   VAKALGHHVT  VISSSDKKKK  EALEDLGADN  YLVSSDTVGM  QEAADSLDYI
        9   VAKALGHHVT  VISSSDKKKK  EALEDLGADN  YLVSSDTVGM  QEAADSLDYI
        10  IAKAMGHHVT  VISSSDKKRT  EALEHLGADA  YLVSSDENGM  KEATDSLDYI
        11  IAKAMGHHVT  VISSSDKKRT  EALEHLGADA  YLVSSDENGM  KEATDSLDYI
        12  IAKAMGHHVT  VISSSNKKRQ  EALEHLGADD  YLVSSDTDKM  QEASDSLDYI
        13  IAKAMGHHVT  VISSSNKKRQ  EALEHLGADD  YLVSSDTDKM  QEAADSLDYI
        14  IAKAMGHHVT  VISSSDKKRE  EAMEHLGADE  YLVSSDVESM  QKAADQLDYI
        15  IAKAMGHHVT  VISSSDKKRE  EAMEHLGADE  YLVSSDVESM  QKAADQLDYI
        16  LAKAMGHHVT  VISSSDKKKE  EAIDHLGADA  YLVSSDATQM  QEAADSLDYI
```

FIG. 10-3

```
      251                                                       300
   1  MDTIPVAHPL EPYLALLKTN GKLVMLGVVP EPLHFVTPLL ILGRRSIAGS
   2  MDTIPVAHPL EPYLALLKTN GKLVMLGVVP EPLHFVTPLL ILGRRSIAGS
   3  MDTIPVAHPL EPYLALLKTN GKLVMLGVVP EPLHFVTPPL ILGRRSIAGS
   4  MDTIPVAHPL EPYLALLKTN GKLVMLGVVP EPLHFVTPLL ILGRRSIAGS
   5  IDTVPVHHPL EPYLALLKLD GKLVLLGVIG EPLSFVSPMV MLGRKAITGS
   6  IDTVPVHHPL EPYLALLKLD GKLVLLGVIG EPLSFVSPMV MLGRKAITGS
   7  IDTVPVHHPL EPYLALLKLD GKHVLLGVIG EPLSFVSPMV MLGRKAITGS
   8  IDTVPVGHPL EPYLSLLKID GKLILMGVIN TPLQFVTPMV MLGRKSITGS
   9  IDTVPVGHPL EPYLSLLKID GKLILMGVIN TPLQFVTPMV MLGRKSITGS
  10  FDTIPVVHPL EPYLALLKLD GKLILTGVIN APLQFISPMV MLGRKSITGS
  11  FDTIPVVHPL EPYLALLKLD GKLILTGVIN APLQFISPMV MLGRKSITGS
  12  IDTVPVGHPL EPYLSLLKID GKLILMGVIN TPLQFISPMV MLGRKSITGS
  13  IDTVPVGHPL ELYLSLLKID GKLILIGVIN TPLQFISPMV MLGRKSITGS
  14  IDTVPVVHPL EPYLSLLKLD GKLILMGVIN TPLQFVSPMV MLGRKSITGS
  15  IDTVPVVHPL EPYLSLLKLD GKLILMGVIN APLQFVTPMV MLGRKSITGS
  16  IDTVPVFHPL EPYLSLLKLD GKLILMGVIN TPLQFISPMV MLGRKAITGS 301                                                       350
   1  FIGSMEETQE TLDFCAEKKV SSMIEVVGLD YINTAMERLE KNDVRYRFVV
   2  FIGSMEETQE TLDFCAEKKV SSMIEVVGLD YINTAMKRLE KNDVRYRFVV
   3  FIGGMEETQE TLDFCAEKKV SSMIEVVGLD YINTAMERLE KNDVRYRFVV
   4  FIGSMEETQE TLDFCAEKKV SSMIEVVGLD YINTAMERLV KNDVRYRFVV
   5  FIGSIDETAE VLQFCVDKGL TSQIEVVKMG YVNEALERLE RNDVRYRFVV
   6  FIGSIDETAE VLQFCVDKGL TSQIEVVKMG YVNEALERLE RNDVRYRFVV
   7  FIGSIDETAE VLQFCVDKGL TSQIEVVKMG YVNEALDRLE RNDVRYRFVV
   8  FVGSVKETEE MLEFWKEKGL TSMIEIVTMD YINKAFERLE KNDVRYRFVV
   9  FVGSVKETEE MLEFWKEKGL TSMIEIVTMD YINKAFERLE KNDVRYRFVV
  10  FIGSMKETEE MLEFCKEKGL TSQIEVIKMD YVNTALERLE KNDVRYRFVV
  11  FIGSMKETEE MLEFCKEKGL TSQIEVIKMD YVNTALERLE KNDVRYRFVV
  12  FIGSMKETEE MLDFCKEKGV TSQIEIVKMD YINTAMERLE KNDVRYRFVV
  13  FIGSMKETEE MLDFCKEKGV TSQIEIVKMD YINTAMERLE KNDVSYRFVV
  14  FIGSMKETEE MLEFCKEKGL ASMIEVIKMD YINTAFERLE KNDVRYRFVV
  15  FIGSMKETEE MLEFCKEKGV ASMIEVIKMD YINTAFERLE KNDVRYRFVV
  16  FIGSMKETEE MLDFCNEKGI TSTIEVVKMD YINTAFERLE KNDVRYRFVV 351        370
   1  DVAGSKLDN* ~~~~~~~~~~
   2  DVAASKLDN* ~~~~~~~~~~
   3  DVAGSELDN* ~~~~~~~~~~
   4  DVAASNLDK* ~~~~~~~~~~
   5  DVAGSNVEAE AAAADAASN*
   6  DVAGSNVEAE AAAADAASN*
   7  DVAGSNV..E EVAADAPSN*
   8  DVKGSKFEE* ~~~~~~~~~~
   9  DVKGSKFEE* ~~~~~~~~~~
  10  DVVGSKLD*~ ~~~~~~~~~~
```

FIG. 10-4

```
11 DVVGSKLD*~ ~~~~~~~~~~
12 DVIGSKLDQ* ~~~~~~~~~~
13 DVAGSKLDQ* ~~~~~~~~~~
14 DVAGSKLIP* ~~~~~~~~~~
15 DVAGSKLIH* ~~~~~~~~~~
16 DVAGSKLDQE T*~~~~~~~~
```

Full length plant CADs from

1) Radiata pine, U62394 (SEQ ID NO: 25)
2) Loblolly pine, Z37992 (SEQ ID NO: 26)
3) Loblolly pine, Z37991 (SEQ ID NO: 27)
4) Norway spruce, X72675 (SEQ ID NO: 28)
5) Maize, aj005702 (SEQ ID NO: 29)
6) Maize, Y13733 (SEQ ID NO: 30)
7) Sugarcane, AJ231135 (SEQ ID NO: 31)
8) Lucerne, AF083332 (SEQ ID NO: 32)
9) Lucerne, Z19573 (SEQ ID NO: 33)
10) Eucalyptus, AF038561 (SEQ ID NO: 34)
11) Eucalyptus, X65631 (SEQ ID NO: 35)
12) Tobacco, X62343 (SEQ ID NO: 36)
13) Tobacco, X62344 (SEQ ID NO: 37)
14) Aspen, AF217957 (SEQ ID NO: 9)
15) Cottonwood, Z19568 (SEQ ID NO: 38)
16) Udo, D13991 (SEQ ID NO: 39)

FIG. 11-1 The alignment of full length plant CAld5H protein sequences

1) Aspen (SEQ ID NO: 4); 2) Poplar, AJ010324 (SEQ ID NO: 40); 3) Sweetgum, AF139532 (SEQ ID NO: 41; 4) Arabidopsis, U38416 (SEQ ID NO: 42). *, Heme-binding signature

```
            1                                                    50
    1   ~MDSLVQSLQ  AS..PMSLFL  IVISSLFFFG  LLSRLRRRLP  YPPGPKGLPL
    2   ~MDSLLQSLQ  TL..PMSFFL  IIISSIFFLG  LISRLRRRSP  YPPGPKGFPL
    3   MDSSLHEALQ  PL..PMTLFF  I.IPLLLLLG  LVSRLRQRLP  YPPGPKGLPV
    4   MESSISQTLS  KLSDPTTSLV  IVVSLFIFIS  FITR.RRRPP  YPPGPRGWPI 51                                                   100
    1   VGSMHMMDQI  THRGLAKLAK  QYGGLFHMRM  GYLHMVTVSS  PEIARQVLQV
    2   IGSMHLMDQL  TDRGLAKLAK  QYGGLFHMRM  GYLHMVAGSS  PEVARQVLQV
    3   IGNMLMMDQL  THRGLAKLAK  QYGGLFHLKM  GFLHMVAVST  PDMARQVLQV
    4   IGNMLMMDQL  THRGLANLAK  KYGGLCHLRM  GFLHMYAVSS  PEVARQVLQV 101                                                   150
    1   QDNIFSNRPA  NIAISYLTYD  RADMAFAHYG  PFWRQMRKLC  VMKLFSRKRA
    2   QDNMFSNRPA  NIAISYLTYD  RADMAFAHYG  PFWRQMRKLC  VMKLFSRKRA
    3   QDNIFSNRPA  TIAISYLTYD  RADMAFAHYG  PFWRQMRKLC  VMKLFSRKRA
    4   QDSVFSNRPA  TIAISYLTYD  RADMAFAHYG  PFWRQMRKVC  VMKVFSRKRA 151                                                   200
    1   ESWESVRDEV  DSMLKTVEAN  IGKPVNLGEL  IFTLTMNITY  RAAFGA.KNE
    2   ESWESVRDEV  DSMVKTVESN  IGKPVNVGEL  IFTLTMNITY  RAAFGA.KNE
    3   ESWESVRDEV  DSAVRVVASN  IGSTVNIGEL  VFALTKNITY  RAAFGTISHE
    4   ESWASVRDEV  DKMVRSVSCN  VGKPINVGEQ  IFALTRNITY  RAAFGSACEK 201                                                   250
    1   GQDEFIKILQ  EFSKLFGAFN  MSDFIPWLGW  IDPQGLSARL  VKARKALDRF
    2   GQDEFIKILQ  EFSKLFGAFN  ISDFIPWLGW  IDPQGLTARL  VKARKALDKF
    3   DQDEFVAILQ  EFSQLFGAFN  IADFIPWLKW  V.PQGINVRL  NKARGALDGF
    4   GQDEFIRILQ  EFSKLFGAFN  VADFIPYFGW  IDPQGINKRL  VKARNDLDGF 251                                                   300
    1   IDSIIDDHIQ  KRKQNKFSED  ...AETDMVD  DMLAFYGEEA  RKVDESDDLQ
    2   IDHIIDDHIQ  KRKQNNYSEE  ...AETDMVD  DMLTFYSEET  .KVNESDDLQ
    3   IDKIIDDHIQ  KGSKN..SEE  ...VDTDMVD  DLLAFYGEEA  .KVSESDDLQ
    4   IDDIIDEHMK  KKENQNAVDD  GDVVDTDMVD  DLLAFYSEEA  KLVSETADLQ 301                                                   350
    1   KAISLTKDNI  KAIIMDVMFG  GTETVASAIE  WVMAELMKSP  EDQKRVQQEL
    2   NAIKLTRDNI  KAIIMDVMFG  GTETVASAIE  WAMAELLKSP  EDIKRVQQEL
    3   NSIKLTKDNI  KA.IMDVMFG  GTETVASAIE  WAMTELMKSP  EDLKKVQQEL
    4   NSIKLTRDNI  KAIIMDVMFG  GTETVASAIE  WALTELLRSP  EDLKRVQQEL
```

FIG. 11-2 (Continued)

```
       351                                                           400
  1  AEVVGLERRV EESDIDKLTF LKCALKETLR MHPPIPLLLH ETSEDAEVAG
  2  ADVVGLERRV EESDFDKLTF FKCTLKETLR LHPPIPLLLH ETSEDAEVAG
  3  AVVVGLDRRV EEKDFEKLTY LKCVLKEVLR LHPPIPLLLH ETAEDAEVGG
  4  AEVVGLDRRV EESDIEKLTY LKCTLKETLR MHPPIPLLLH ETAEDTSIDG 401                                                           450
  1  YFIPKQTRVM INAYAIGRDK NSWEDPDAFK PSRFLKPGVP DFKGNHFEFI
  2  YVVPKKTRVM INAYAIGRDK NSWEDPDSFK PSRFLEPGVP DFKGNHFEFI
  3  YYIPAKSRVM INACAIGRDK NSWADPDTFR PSRFLKDGVP DFKGNNFEFI
  4  FFIPKKSRVM INAFAIGRDP TSWTDPDTFR PSRFLEPGVP DFKGSNFEFI 451                                                           500
  1  PFGSGRRSCP GMQLGLYTLD LAVAHLLHCF TWELPDGMKP SELDMTDMFG
  2  PFGSGRRSCP GMQLGLYALD LAVAHLLHCF TWELPDGMKP SELDMTDMFG
  3  PFGSGRRSCP GMQLGLYALE TTVAHLLHCF TWELPDGMKP SELEMNDVFG
  4  PFGSGRRSCP GMQLGLYALD LAVAHILHCF TWKLPDGMKP SELDMNDVFG
     ********** *

501           523
  1  LTAPRATRLV AVPSKRVLCP L*
  2  LTAPRATRLV AVPRKRVVCP L~~
  3  LTAPRAIRLT AVPSPRLLCP LY*
  4  LTAPKATRLF AVPTTRLICA L~~
```

FIG. 12-1 PLANT 4CL AMINO ACID SEQUENCE ALIGNMENTS

```
(1)   1:-----------------MNPQ-EFIFRSKLPDIYIPKNLPLHSYVLENLSKHSSKPCLI 41
(2)   1:--------------MDAIMNSQEEFIFRSKLPDIYIPKNLPLHSYVLENLSKYSSKPCLI 46
(3)   1:--------------MGDCVAPKEDLIFRSKLPDIYIPKHLPLHTYCFENISKVGDKSCLI 46
(4)   1:------------MPMDTETKQSGDLIFRSKLPDIYIPKHLPLHSYCFENLSEFNSRPCLI 48
(5)   1:---------------M-AVQTPQHNIVYRSKLPDIHIPNHLPLHSYIFQNKSHLTSKPCII 45
(6)   1:------------MPMDTETKQSGDLIFRSKLPDIYIPKHLPLHSYCFENLSEFNSRPCLI 48
(7)   1:--------------MEKDTKH-GDIIFRSKLPDIYIPNHLPLHSYCFENISEFSSRPCLI 45
(8)   1:MGSME-Q-QQPES-AAPATEASPEIIFRSKLQDIAITNTLPLHRYCFERLPEVAARPCLI 57
(9)   1:MITLAPSLDTPKTDQNQVSDPQTSHVFKSKLPDIPISNHLPLHSYCFQNLSQFAHRPCLI 60
(10)  1:MAPQE-Q-AVSQVMEKQSNNNNSDVIFRSKLPDIYIPNHLSHDYIFQNISEFATKPCLI 58
(11)  1:----A-N-GI-K----KV-E----HLYRSKLPDIEISDHLPLHSYCFERVAEFADRPCLI 44
(12)  1:M---A-N-GI-K----KV-E----HLYRSKLPDIEISDHLPLHSYCFERVAEFADRPCLI 45
(13)  1:------------------------------------------------------------
(14)  1:------------------------------------------------------------
(15)  1:----------------------------------------------------------LI 2
(16)  1:--------------------------------------------------------PCLI 4

(1)   42:NG-ANGDVYTYADVELTARRVA-SGLNKIGIQQGDVIMLFLPSSPEFVLAFLGASHRGAM 99
(2)   47:NG-ANGDVYTYADVELTARRVA-SGLNKIGIQQGDVIMLFLPSSPEFVLAFLGASHRGAI 104
(3)   47:NG-ATGETFTYSQVELLSRKVA-SGLNKLGIQQGDTIMLLLPNSPEYFFAFLGASYRGAI 104
(4)   49:DG-ANDRIYTYAEVELTSRKVA-VGLNKLGIQQKDTIMILLPNCPEFVFAFIGASYLGAI 106
(5)   46:NG-TTGDIHTYAKFKLTARKVA-SGLNKLGIEKGDVFMLLLPNTSEFVFAFLGASFCGAM 103
(6)   49:DG-ANDRIYTYAEVELTSRKVA-VGLNKLGIQQKDTIMILLPNCPEFVFAFIGASYLGAI 106
(7)   46:NG-ANKQIYTYADVELSSRKVA-AGLHKQGIQQKDTIMILLPNSPEFVFAFIGASYLGAI 103
(8)   58:DGATGGVLTYADVDRLSRRLAAALRRAPLGLRRGGVVMSLLRNSPEFVLSFFAASRVGAA 117
(9)   61:VG-PASKTFTYADTHLISSKIA-AGLSNLGILKGDVVMILLQNSADFVFSFLAISMIGAV 118
(10)  59:NGPTGHVYTYSDVHVISRQIAANFHK--LGVNQNDVVMLLLPNCPEFVLSFLAASFRGAT 116
(11)  45:DG-ATDRTYCFSEVELISRKVA-AGLAKLGLQQGQVVMLLLPNCIEFAFVFMGASVRGAI 102
(12)  46:DG-ATDRTYCFSEVELISRKVA-AGLAKLGLQQGQVVMLLLPNCIEFAFVFMGASVRGAI 103
(13)  1:-----------------------A-----K-------------------------A- 3
(14)  1:------------------------------------------------------------
(15)  3:DG-STNKTYNFAEVELISRKVA-AGLAKLGLKKGQVVMLLLQNCIEFAFVFMGASVLGAV 60
(16)  5:DG-ATGKTHCFAEVELISRKVA-AGLVNLGLQQGQVVMLLLQNCVEFAFVFMGAALRGAI 62

(1)   100:ITAANPFSTPAELAKHAKASRAKLLITQACYYEKVK--DFARESDVKVMCVDS-APD-GA 155
(2)   105:VTAANPFSTPAELAKHAKPPRTKLLITQACYYDKVK--DFARESDVKVMCVDS-APD-GC 160
(3)   105:STMANPFFTSAEVIKQLKASQAKLIITQACYVDKVK--DYAAEKNIQIICID-DAP-QDC 160
(4)   107:STMANPLFTPAEVVKQAKASSAKIVITQACFAGKVK--DYAIENDLKVICVD-SVP-EGC 162
(5)   104:MTAANPFFTPAEIAKQAKASKAKLIITFACYYDKVK--DLSCD-EVKLMCIDSPPPDSSC 160
(6)   107:STMANPLFTPAEVVKQAKASSAKIIITQACFAGKVK--DYAIENDLKVICVD-SAP-EGC 162
(7)   104:STMANPLFTAAEVVKQVKASGAKIIVTQACHVNKVK--DYALENNVKIICID-SAP-EGC 159
(8)   118:VTTANPMSTPHEIESQLAAAGATVVITESMAADKL-PSHSHGALTVV-LID-E--R-RDG 171
(9)   119:ATTANPFYTAPEIFKQFTVSKAKLIITQAMYVDKLRNHDGAKLGEDFKVVTVDDPP-ENC 177
(10)  117:ATAANPFFTPAEIAKQAKASNTKLIITEARYVDKIKPLQNDDGVVIVCIDDNESVPIPEG 176
(11)  103:VTTANPFYKPGEIAKQAKAAGARIIVTLAAYVEKL-A-D-LQ-SHDVLVITIDDAPKEGC 158
(12)  104:VTTANPFYKPGEIAKQAKAAGARIIVTLAAYVEKL-A-D-LQ-SHDVLVITIDDAPKEGC 159
(13)  4:---A------G----------ARIIVTQAAYVDKL-A-D-LQ-SDDMIVIAIDGAPKEGC 40
(14)  1:--------KPGEIAKQAKAAGARIIVTQAAYVEKL-A-D-LQ-NDDVIVITIDAAPKEGC 48
(15)  61:VTTANPFYKPGEIAKQAKAADARIIVTQAAYVDKL-A-D-LQ-SEDVISIDGAPKEGC 116
(16)  63:VTTANPFYKPGEIAKQAKAAGARIIVTQAAYVEKL-A-D-LQ-SDDVIVITIDGAPKDGC 118
                                                *       *
(1)   156:SLFRAHTQADENEVPQV--------DISPDDVVALPYSSGTTGLPKGVMLTHKGLITSVA 207
(2)   161:LHFSELTQADENEVPQV--------DFSPDDVVALPYSSGTTGLPKGVMLTHKGLITSVA 212
(3)   161:LHFSKLMEADESEMPEV--------VINSDDVVALPYSSGTTGLPKGVMLTHKGLVTSVA 212
(4)   163:VHFSELIQSDEHEIPDV--------KIQPDDVVALPYSSGTTGLPKGVMLTHKGLVTSVA 214
(5)   161:LHFSELTQSDENDVPDV--------DISPDDVVALPYSSGTTGLPKGVMLTHKGLVTSVS 212
```

FIG. 12-2

```
(6)    163:VHFSELIQSDEHEIPDV--------KIQPDDVVALPYSSGTTGLPKGVMLTHKGLVTSVA 214
(7)    160:LHFSVLTQADEHDIPEV--------EIQPDDVVALPYSSGTTGLPKGVMLTHKGLVTSVA 211
(8)    172:CLHFWDDLMSEDEASPLAGDEDDEKVFDPDDVVALPYSSGTTGLPKGVMLTHRSLSTSVA 231
(9)    178:LHFSVLSEANESDVPEV--------EIHPDDAVAMPFSSGTTGLPKGVILTHKSLTTSVA 229
(10)   177:CLRF-TEL-TQSTTEA-SEVIDSVEI-SPDDVVALPYSSGTTGLPKGVMLTHKGLVTSVA 232
(11)   159:QHISVLTEADETQCPAV--------KIHPDDVVALPYSSGTTGLPKGVMLTHKGLVSSVA 210
(12)   160:QHISVLTEADETQCPAV--------KIHPDDVVALPYSSGTTGLPKGVMLTHKGLVSSVA 211
(13)    41:QHISILTEADETQCPSV--------EIHPDDVVALPYSSGTTGLPKGVMLTHKSQVSSVA  92
(14)    49:QHISVLTEADETQCPSV--------EIQPDDVVALPYSSGTTGLPKGVMLTHKGLVSSVA 100
(15)   117:QHISVLTEADETQCPSV--------EIHPDDVVALPYSSGTTGLPKGVMLTHKSLVSSVA 168
(16)   119:KDISVLTEADGTQCPSV--------EIQPDDVVALPYSSGTTGLPKGVMLTHKGLVSSVA 170
                                          ** ** * *********** ***      **

(1)    208:QQVDGDNPNLYFHSEDVILCVLPMFHIYALNSMMLCGLRVGASILIMPKFEIGSLLGLIE 267
(2)    213:QQVDGDNPNLYFHSEDVILCVLPMFHIYALNSIMLCGLRVGASILIMPKFDIGTLLGLIE 272
(3)    213:QQVDGDNPNLYMHSEDVMICILPLFHIYSLNAVLCCGLRAGVTILIMQKFDIVPFLELIQ 272
(4)    215:QQVDGENANLYMHSDDVLMCVLPLFHIYSLNSVLLCALRVGAAILIMQKFDIAQFLELIP 274
(5)    213:QQVDGENPNLYYSSDDVVLCVLPLFHIYSLNSVLLCGLRAGAAILLMQKFEIVSLLELMQ 272
(6)    215:QQVDGENANLYMHSDDVLMCVLPLFHIYSLNSVLLCALRVGAAILIMQKFDIAQFLELIP 274
(7)    212:QQVDGENRNLYIHSEDVLLCVLPLFHIYSLNSVLLCGLRVGAAILIMQKFDIVPFLELIQ 271
(8)    232:QQVDGENPNIGLHAGDVILCALPMFHIYSLNTIMMCGLRVGAAIVVMRRFDLAAMMDLVE 291
(9)    230:QQVDGENPNLYLTTEDVLLCVLPLFHIFSLNSVLLCALRAGSAVLLMQKFEIGTLLELIQ 289
(10)   233:QQVDGENPNLYFHSDDVILCVLPMFHIYALNSIMLCGLRVGAAILIMPKFEINLLLELIQ 292
(11)   211:QQVDGENPNLYFHSDDVILCVLPLFHIYSLNSVLLCALRAGAATLIMQKFNLTTCLELIQ 270
(12)   212:QQVDGENPNLYFHSDDVILCVLPLFHIYSLNSVLLCALRAGAATLIMQKFNLTTCLELIQ 271
(13)    93:QQVDGENPNLYFHSEDVILCVLPLFHIYSLNSVLLCALRAGAATLIMQKFNLTALLELIQ 152
(14)   101:QQVDGENPNLYFHSDDVIICVLPLFHIYSLNSVLLCALRAGAATLIMQKFNMASFLELIQ 160
(15)   169:QQVDGENPNLYFHSEDVILCVLPLFHIYSLNSVLLCALRAGAATLIMQKFNLTTLLELIQ 228
(16)   171:QQVDGENPNLYFHSEDVVMCVLPLFHIYSLNSVLLCALRAGAATLIMQKFNMTSFLELIQ 230
            ***** * *        **  * ** ***   **      *  ** *     *    *

(1)    268:KYKVSIAPVVPPVMMAIAKSPDLDKHDLSSLRMIKSGGAPLGKELEDTVRAKFPQARLGQ 327
(2)    273:KYKVSIAPVVPPVMLAIAKSPDFDKHDLSSLRMIKSGGAPLGKELEDTVRAKFPQARLGQ 332
(3)    273:KYKVTIGPFVPPIVLAIAKSPVVDKYDLSSVRTVMSGAAPLGKELEDAVRAKFPNAKLGQ 332
(4)    275:KHKVTIGPFVPPIVLAIAKSPLVDNYDLSSVRTVMSGAAPLGKELEDAVRAKFPNAKLGQ 334
(5)    273:KHRVSVAPIVPPTVLAIAKFPDLDKYDLGSIRVLKSGGAPLGKELEDTVRAKFPNVTLGQ 332
(6)    275:KHKVTIGPFVPPIVLAIAKSPLVHNYDLSSVRTVMSGAAPLGKELEDAVRAKFPNAKLGQ 334
(7)    272:NYKVTIGPFVPPIVLAIAKSPMVDDYDLSSVRTVMSGAAPLGKELEDTVRAKFPNAKLGQ 331
(8)    292:RHRVTIAPLVPPIVVAVAKSEAAAARDLSSVRMVLSGAAPMGKDIEDAFMAKLPGAVLGQ 351
(9)    290:RHRVSVAMVVPPLVLALAKNPMVADFDLSSIRLVLSGAAPLGKELEEALRNRMPQAVLGQ 349
(10)   293:RCKVTVAPMVPPIVLAIAKSSETEKYDLSSIRVVKSGAAPLGKELEDAVNAKFPNAKLGQ 352
(11)   271:KYKVTVAPIVPPIVLDITKSPIVSQYDVSSVRIIMSGAAPLGKELEDALRERFPKAIFGQ 330
(12)   272:KYKVTVAPIVPPIVLDITKSPIVSQYDVSSVRIIMSGAAPLGKELEDALRERFPKAIFGQ 331
(13)   153:RYKVTVAPIVPPIVLEISKNPIVSQYDVPSSVRIIMSGAAPLGKELEDALRERFPKAIFGQ 212
(14)   161:RYKVTVAPIVPPIVLDITKSPIISQYDVSSVRIIMSGAAPLGKELEDALRDRFPQAIFGQ 220
(15)   229:RYKVTVAPIVPPIVLDITKNPIVSQYDVSSVRIIMSGAAPLGKELEDALRERFPKAIFGQ 288
(16)   231:RYKVTVAPIVPPVVLEITKSPIVSQYDISSVRIIVSGGAPLGKELEDAIRDRLPHAIFGQ 290
             *    ***       *        *   *   ** ** **  *      *      **

(1)    328:GYGMTEAGPVLAMCLAFAKEPFDIKPGACGTVVRNAEMKIVDPETGVSLPRNQPGEICIR 387
(2)    333:GYGMTEAGPVLAMCLAFAKEPFDIKPGACGTVVRNAEMKIVDPETGASLRRNQPGEICIR 392
(3)    333:GYGMTEAGPVLAMCLAFAKEPYEIKSGACGTVVRNAEMKIVDPETNASLPRNQRGEICIR 392
(4)    335:GYGMTEAGPVLAMCLAFAKEPFDIKSGACGTVVRNAEMKIVDPDTGCSLPRNQPGEICIR 394
(5)    333:GYGMTEAGPVLTMSLAFAKEPFEVKPGGCGTVVRNAELKIVDPETGASLPRNHPGEICIR 392
(6)    335:GYGMTEAGTVLTMCLAFAKEPFDIKSGACGTVVRNAEMKIVDPDTGCSLPRNQPGEICIR 394
(7)    332:GYGMTEAGPVLAMCLAFAKEPFEIKSGACGTVVRNAEMKIVDPETGNSLPRNQSGEICIR 391
(8)    352:GYGMTEAGPVLSMCLAFAKEPFKVKSGACGTVVRNAELKIIDPDTGKSLGRNLRGEICIR 411
(9)    350:GYGMTEAGPVLSMCLGFAKQPFQTKSGSCGTVVRNAELKVVDPETGRSLGYNQPGEICIR 409
```

FIG. 12-3

```
(10)  353:GYGMTEAGPVLAMSLGFAKEPFPVKSGACGTVVRNAEMKIVDPDTGDSLSRNQPGEICIR 412
(11)  331:GYGMTEAGPVLAMNLAFAKNPFPVKSGSCGTVVRNAQIKILDTETGESLPHNQAGEICIR 390
(12)  332:GYGMTEAGPVLAMNLAFAKNPFPVKSGSCGTVVRNAQIKILDTETGESLPHNQAGEICIR 391
(13)  213:GYGMTEAGPVL------------------------------------------------ 223
(14)  221:GYGMTEAGPV-------------------------------------------------  230
(15)  289:GYGMTEAGPVLAMNLAFAKEPFPVKSGSC------------------------------- 317
(16)  291:GYGMTEAGPVLAMNLAFAKEPFPVKSGS-------------------------------- 318
          ******** *

(1)   388:GDQIMKGYLNDPEATSRTIDKEGWLHTGDIGYIDDDDELFIVDRLKELIKYKGFQVAPTE 447
(2)   393:GDQIMKGYLNDPEATSRTIDKEGWLHTGDIGYIDDDDELFIVDRLKELIKYKGFQVAPAE 452
(3)   393:GDQIMKGYLNDPESTRTTIDEEGWLHTGDIGFIDDDDELFIVDRLKEIIKYKGFQVAPAE 452
(4)   395:GDQIMKGYLNDPEATARTIEKEGWLHTGDIGFIDDDDELFIVDRLKELIKYKGFQVAPAE 454
(5)   393:GHQIMKGYLNDPEATRTTIDKQGWLHTGDIGFIDDEELFIVDRLKELIKYKGFQVAPAE 452
(6)   395:GDQIMKGYLNDPEATARTIEEEGWLHTGDIGFIDDDDELFIVDRLKELIKYKGFQVAPAE 454
(7)   392:GDQIMKGYLNDPEATARTIDKEGWLYTGDIGYIDDDDELFIVDRLKELIKYKGFQVAPAE 451
(8)   412:GQQIMKGYLNNPEATKNTIDAEGWLHTGDIGYVDDDDEIFIVDRLKEIIKYRGFQVAPAE 471
(9)   410:GQQIMKGYLNDEAATASTIDSEGWLHTGDVGYVDDDDEIFIVDRVKELIKYKGFQVPPAE 469
(10)  413:GHQIMKGYLNNPAATAETIDKDGWLHTGDIGLIDDDDELFIVDRLKELIKYKGFQVAPAE 472
(11)  391:GPEIMKGYINDPESTAATIDEEGWLHTGDVEYIDDDEEIFIVDRVKEIIKYKGFQVAPAE 450
(12)  392:GPEIMKGYINDPESTAATIDEEGWLHTGDVGYIDDDEEIFIVDRVKEIIKYKGFQVAPAE 451
(13)  224:------------------------------------------------------------
(14)  231:------------------------------------------------------------
(15)  318:------------------------------------------------------------
(16)  319:------------------------------------------------------------

(1)   448:LEALLIAHPEISDAAVVGLKDEDAGEVPVAFVVKSEKSQATEDEIKQYISKQVIFYKRIK 507
(2)   453:LEALLLAHPQISDAAVVGMKDEDAGEVPVAFVVKSEKSQATEDEIKQYISKQVIFYKRIK 512
(3)   453:LEALLLTHPTISDAAVVPMIDEKAGEVPVAFVVRTNGFTTTEEEIKQFVSKQVVFYKRIF 512
(4)   455:LEALLINHPDISDAAVVPMIDEQAGEVPVAFVVRSNGSTITEDEVKDFISKQVIFYKRIK 514
(5)   453:LEALLVTHPNISDAAVVPMKDDAAGEVPVAFVVSPKGSQITEDEIKQFISKQVVFYKRIK 512
(6)   455:LEALLINHPDISDAAVVPMIDEQAGEVPVAFVVRSNGSTITEDEVKDFISKQVIFYKRIK 514
(7)   452:LEALLLNHPTFSDAAVVPMKDEQAEEVPVAFVVRSSGSTITEDEVKDFISKQVIFYKRIK 511
(8)   472:LEALLNTHPSIADAAVVGLK---FGEIPVAFVAKTEGSELSEDDVKQFVAKEVIYYKKIR 528
(9)   470:LEGLLVSHPSIADAAVVPQKDVAAGEVPVAFVVRSNGFDLTEEAVKEFIAKQVVFYKRLH 529
(10)  473:LEALLIGHPDITDVAVVAMKEEAAGEVPVAFVVKSKDSELSEDDVKQFVSKQVVFYKRIN 532
(11)  451:LEALLVAHPSIADAAVVPQKHEEAGEVPVAFVVKS-S-EISEQEIKEFVAKQVIFYKKIH 508
(12)  452:LEALLVAHPSIADAAVVPQKHEEAGEVPVAFVVKS-S-EISEQEIKEFVAKQVIFYKKIH 509
(13)  224:------------------------------------------------------------
(14)  231:------------------------------------------------------------
(15)  318:------------------------------------------------------------
(16)  319:------------------------------------------------------------

(1)   508:RVFFIEAIPKAPSGKILRKNLKEKL-PGI------                    535
(2)   513:RVFFIEAIPKAPSGKILRKNLRETL-PGI------                    540
(3)   513:RVFFVDAIPKSPSGKILRKDLRARIASGDLPK---                    544
(4)   515:RVFFVETVPKSPSGKILRKDLRARLAAGISN----                    545
(5)   513:RVFFIEAIPKSPSGKILRKELRAKLAAGFAN----                    543
(6)   515:RVFFVETVPKSPSGKILRKDLRARLAAGISN----                    545
(7)   512:RVFFVDAVPKSPSGKILRKDLRAKLAAGLPN----                    542
(8)   529:EVFFVDKIPKAPSGKILRKELRKQLQHLQQEALTN                    563
(9)   530:KVYFVHAIPKSPSGKILRKDLRAKLETAATQTP--                    562
(10)  533:KVFFTESIPKAPSGKILRKDLRAKLANGL------                    561
(11)  509:RVYFVDAIPKSPSGKILRKDLRSRLAAK-------                    536
(12)  510:RVYFVDAIPKSPSGKILRKDLRSRLAAK-------                    537
```

1: aspen AF041049 (SEQ ID NO: 10)
2: Hybrid populus AF283552 (SEQ ID NO: 43)
3: Parsley X13324 (SEQ ID NO: 44)
4: potato M62755 (SEQ ID NO: 45)
5: Rubus idaeus AF239687 (SEQ ID NO: 46)
6: solanum AF150686 (SEQ ID NO: 47)
7: Tobacco D43773 (SEQ ID NO: 48)
8: rice x52623 (SEQ ID NO: 49)
9: soybean x69955 (SEQ ID NO: 50)
10: Arabidopsis AF106084 (SEQ ID NO: 51)
11: PinusteadaU12012 (SEQ ID NO: 52)
12: Pinus teada U12013 (SEQ ID NO: 53)
13: Larix AF144513 (SEQ ID NO: 54)
14: PseudolarixAF144528 (SEQ ID NO: 55)
15: Pseudotsuga AF144511 (SEQ ID NO: 56)
16: Tsuga AF144526 (SEQ ID NO: 57)

METHODS FOR SIMULTANEOUS CONTROL OF LIGNIN CONTENT AND COMPOSITION, AND CELLULOSE CONTENT IN PLANTS

CROSS-REFERENCE TO RELATED APPLICATIONS

This application is a continuation of U.S. patent application Ser. No. 09/947,027, filed Sep. 5, 2001 now U.S. Pat. No. 6,855,864, and claims the benefit of U.S. Provisional Application No. 60/230,086 filed Sep. 5, 2000, which applications are incorporated by reference herein in their entireties.

BACKGROUND OF THE INVENTION

The invention provides a method of introducing two or more genes, involved in lignin biosynthesis, into plant cells. The method of the invention employs either an *Agrobacterium*-mediated or other appropriate plant gene delivery system by which multiple genes together with a single selectable marker gene are simultaneously transferred and inserted into the genome of plants with high frequencies.

The ability to introduce foreign genes into plants is a prerequisite for engineering agronomic traits in plants. Many systems have been developed for introducing a foreign gene into plant cells, which involve mainly either *Agrobacterium*- or microprojectile bombardment-mediated transformation (Christou, 1996). The principle of all these systems involves the insertion of a target gene into the host plant genome together with a selectable marker gene encoding either antibiotic or herbicide resistance to aid in the selection of transgenic cells from non-transgenic cells. These systems generally are only effective for introducing a single target gene into the host plant.

To alter agronomic traits, which generally are polygenic in nature, multiple genes involved in complex biosynthetic pathways must be introduced and expressed in plant cells. In this context, the traditional single-gene transfer systems are essentially useless for the following two reasons: 1) it is impractical to introduce multiple genes by repetitive insertion of single genes into transgenic plants due to the time and effort required for recovery of the transgenic tissues; in particular, a repetitive single-gene approach is highly impractical for plant species such as trees which, depending upon the species, require two to three years for transgenic tissue selection and regeneration into a tree; and 2) the presence of a selectable marker gene in a transgenic line precludes the use of the same marker gene in subsequent transformations of plant material from that line. Moreover, the number of available marker genes is limited, and many plant species are recalcitrant to regeneration unless appropriate antibiotic or herbicide selection is used.

Chen et al. (1998) recently reported the genetic transformation of rice with multiple genes by cobombardment of several gene constructs into embryogenic suspension tissues. However, particle bombardment-mediated gene transfer into embryogenic tissues is highly species-dependent, and regeneration of whole plants from embryogenic cells cannot be achieved for a variety of plant species (Horsch et al., 1985).

In contrast, *Agrobacterium*-mediated gene transfer and whole plant regeneration through organogenesis is a simple process and a less species-dependent system than bombardment-mediated transformation and regeneration via embryogenesis. However, the introduction of more than one gene in a single plasmid vector via *Agrobacterium* may be technically troublesome and limited by the number or the size of the target genes (Chen et al., 1998). For example, Tricoli et al. (1995) reported the transfer of three target genes to squash via *Agrobacterium*-mediated gene transfer. A binary plasmid vector containing the three target genes was incorporated into an *Agrobacterium* strain, which was subsequently used to infect the leaf tissue of squash. As only one line was recovered from numerous infected squash tissues that contained all of the target genes, the use of a single binary vector with a number of genes appears to be a highly inefficient method to produce transgenic plants with multiple gene transfers. Therefore, it was commonly accepted that transfer of multiple genes via *Agrobacterium*-mediated transformation was impractical (Ebinuma et al., 1997), until success of multiple gene transfer via *Agrobacterium* was first reported in co-pending, commonly owned PCT application, PCT/US/ 0027704, filed Oct. 6, 2000, entitled "Method of Introducing a Plurality of Genes into Plants" by Chiang et al, incorporated herein by reference. However, homologous tissue-specific preparation of transgenic trees to specifically alter lignin content, increase S/G (syringyl:guaiacyl) lignin ratio and increase cellulose quantity, as compared to an untransformed plant was unsuccessful.

Yet, the altering of lignin content and composition in plants has been a goal of genetically engineered traits in plants. Lignin, a complex phenolic polymer, is a major part of the supportive structure of most woody plants including angiosperm and gymnosperm trees, which, in turn, are the principal sources of fiber for making paper and cellulosic products. Lignin generally constitutes about 25% of the dry weight of the wood, making it the second most abundant organic compound on earth after cellulose. Lignin provides rigidity to wood for which it is well suited due, in part, to its resistance to biochemical degradation.

Despite its importance to plant growth and structure, lignin is nonetheless problematic to post-harvest, cellulose-based wood/crop processing for fiber, chemical, and energy production because it must be removed or degraded from cellulose at great expense. Certain structural constituents of lignin, such as the guaiacyl (G) moiety, promote monomer cross-linkages that increase lignin resistance to degradation (Sarkanen, 1971; Chang and Sarkanen, 1973; Chiang and Funaoka, 1990). In angiosperms, lignin is composed of a mixture of guaiacyl (G) and syringyl (S) monolignols, and can be degraded at considerably less energy and chemical cost than gymnosperm lignin, which consists almost entirely of guaiacyl moieties (Freudenberg, 1965). It has been estimated that, if syringyl lignin could be genetically incorporated into gymnosperm guaiacyl lignin or into angiosperms to increase the syringyl lignin content, the annual saving in processing of such genetically engineered plants as opposed to their wild types would be in the range of $6 to $10 billion in the U.S. alone. Consequently, there has been long-standing incentive to understand the biosynthesis of syringyl monolignol to genetically engineer plants to contain more syringyl lignin, thus, facilitating wood/crop processing (Trotter, 1990; Bugos et al., 1991; Boudet et al., 1995; Hu et al., 1999).

Depending on the use for the plant, genetic engineering of certain traits has been attempted. For some plants, as indicated above, there has been a long-standing incentive to genetically modify lignin and cellulose to decrease lignin and increase cellulose contents. For example, it has been demonstrated that the digestibility of forage crops by ruminants is inversely proportional to lignin content in plants (Buxton and Roussel, 1988, Crop. Sci., 28, 553-558; Jung and Vogel, 1986, J. Anim., Sci., 62, 1703-1712). Therefore, decreased lignin and high cellulose plants are desirable in forage crops to increase their digestibility by ruminants, thereby providing the animal with more nutrients per unit of forage.

In other plants, genetically increasing the S/G ratio of the lignin has been sought. As noted above, lignin in angiosperms is composed of guaiacyl (G) and syringyl (S) monomeric units, whereas gymnosperm lignin consists entirely of G units. The structural characteristics of G units in gymnosperm lignin promote monomer cross-linkages that increase lignin resistance to chemical extraction during wood pulp production. However, the S units present in angiosperm lignin prevent such chemical resistant cross-links. Therefore, without exception, chemical extraction of G lignin in pulping of gymnosperms is more difficult and requires more chemicals, longer reaction times and higher energy levels than the extraction of G-S lignin during pulping of angiosperms (Sarkanen, K.V., 1971, in Lignins: Occurrence, Formation, Structure and Reaction, Sarkanen, K. V. & Ludwig, C. H., eds., Wiley-Interscience, New York; Chang, H. M. and Sarkanen, K. V., 1973, TAPPI, 56:132-136). As a rule, the reaction rate of extracting lignin during wood pulping is directly proportional to the quantity of the S unit in lignin (Chang, H. M. and Sarkanen, K. V., 1973, TAPPI, 56:132-136). Hence, altering lignin into more reactive G-S type in gymnosperms and into high S/G ratio in angiosperms would represent a pivotal opportunity to enhance current pulping and bleaching efficiency and to provide better, more economical, and more environmentally sound utilization of wood.

Recent results have indicated that high S/G ratio may also add further mechanical advantages to plants, balancing the likely loss of sturdiness of plants with severe lignin reduction (Li et al., 2001, Plant Cell, 13:1567-1585). Moreover, a high S/G lignin ratio would also improve the digestibility of forage crops by ruminants (Buxton and Roussel, 1988, Crop. Sci., 28, 553-558; Jung and Vogel, 1986, J. Anim., Sci., 62, 1703-1712).

In some applications, both a high lignin content and high S/G ratio have been sought (i.e., combining these two traits in plants). For example, it has been demonstrated that when lignin is extracted out from wood during chemical pulping, lignin in the pulping liquor is normally used as a fuel source to provide energy to the pulping and bleaching operations. This lignin-associated energy source, which is not necessary for pulp mills using purchased fuel for energy, is essential to some pulp mills which depend upon internal sources, such as extracted lignin, to be self-sufficient in energy. Therefore, for this purpose, it may be desirable to increase lignin content in pulpwood species, and at the same time to increase the S/G ratio in these species to facilitate the extraction of more lignin to be used as fuel.

Additionally, for grain production and other non-related purposes, increased lignin content and/or S/G lignin ratio are desirable to provide extra sturdiness in plants to prevent the loss of socially and economically important food crops due to dislodging and due to damage to the aerial parts of the plant.

The plant monolignol biosynthetic pathway is set forth in FIG. 1 and will be explained in more detail hereinbelow. The key lignin control sites in the monolignol biosynthetic pathway are mediated by genes encoding the enzymes 4-coumarate-CoA ligase (4CL) (Lee et al., 1997), coniferyl aldehyde 5-hydroxylase (CAld5H) (Osakabe et al., 1999) and S-adenosyl-L-methionine (SAM)-dependent 5-hydroxyconiferaldehyde O-methyltransferase (AldOMT) (Li et al., 2000), respectively, for the formation of sinapaldehyde (see, FIG. 1). Further, coniferyl alcohol dehydrogenase (CAD) (MacKay et al., 1997) catalyzes the reaction including the substrate coniferaldehyde to coniferyl alcohol. It has recently been discovered that sinapyl alcohol dehydrogenase (SAD) enzymatically converts sinapaldehyde into sinapyl alcohol, the syringyl monolignol, for the biosynthesis of syringyl lignin in plants (see, FIG. 1). See, concurrently filed, commonly owned U.S. non-provisional application entitled "Genetic Engineering of Syringyl-Enriched Lignin in Plants," incorporated herein by reference. It should be noted that the gene encoding the enzyme sinapyl alcohol dehydrogenase (SAD) represents the last gene that is indispensable for genetic engineering of syringyl lignin in plants.

A summary of the conserved regions contained within the coding sequence of each of the above listed proteins is described below. Because SAD is a recently discovered enzyme in Aspen, sequence alignments with other representative species were unable to be performed.

The protein sequence alignments of plant AldOMTs are shown in FIG. 9. All AldOMTs have three conserved sequence motifs (I, II, and III) which are the binding sites of S-adenosyl-L-methionine (SAM), the co-substrate or methyl donor for the OMT reaction (Ibrahim, 1997, Trends Plant Sci., 2:249-250; Li et al., 1997, Proc. Natl. Acad. Sci. USA, 94:5461-5466; Joshi and Chiang, 1998, Plant Mol. Biol., 37:663-674). These signature sequence motifs and the high sequence homology of these proteins to PtAldOMT attest to their function as an AldOMT specific for converting 5-hydroxyconiferaldehyde into sinapaldehyde (Li et al., 2000, J. Biol. Chem., 275:6537-6545). This AldOMT, like CAld5H, also operates at the aldehyde level of the plant monolignol biosynthetic pathway.

The protein sequence alignments of plant CADs are shown in FIG. 10. It was recently proven that CADs are actually guaiacyl monolignol pathway specific (Li et al., 2001, Plant Cell, 13:1567-1585). Based on high sequence homology, the alignment program picked up CADs from angiosperms as well as gymnosperms (radiata pine, loblolly pine and spruce) which have only G-lignin. All CADs have the Zn1 binding motif and structural Zn2 consensus region, as well as a NADP binding site (Jornvall et al., 1987, Eur. J. Biochem., 167:195-201; MacKay et al., 1995, Mol. Gen. Genet., 247:537-545). All these sequence characteristics and high sequence homology to PtCAD attest to these CAD function as a G-monolignol specific CAD (Li et al., 2001, Plant Cell, 13:1567-1585).

The protein sequence alignments of plant Cald5Hs are shown in FIG. 11. Although, there are different types of 5-hydroxylases, i.e., F5H, CAld5H is the sole enzyme catalyzing specifically the conversion of coniferaldehyde into 5-hydroxyconiferaldehyde. All full-length CAld5Hs have the proline-rich region located from amino acid 40 to 45 which is believed to be involved in the process of correct folding of microsomal P450s and is also important in heme incorporation into P450s (Yamazaki et al. 1993, J. Biochem. 114:652-657). Also they all have the heme-binding domain (PF-GXGXXXCXG, SEQ ID NO: 58) that is conserved in all P450 proteins (Nelson et al. 1996, Pharmacogenetics, 6:1-41). These signature sequences and the high sequence homology of these proteins to PtCAld5H their function as a 5-hydroxylase that is specific for converting coniferaldehyde into 5-hydroxyconiferaldehyde (Osakabe et al., 1999, Proc. Natl. Acad. Sci. USA, 96:8955-8960).

The protein sequence alignment of plant 4CLs are shown in FIG. 12. In general, 4CL catalyzes the activation of the hydroxycinnamic acids to their corresponding hydroxycinnamoyl-CoA esters. 4CL has the highest activity with p-coumaric acid. 4CL cDNA sequences have been reported from a number of representative angiosperms and gymnosperms, revealing two highly conserved regions, a putative AMP-binding region (SSGTTGLPKGV, SEQ ID NO: 59), and a catalytic motif (GEICIRG, SEQ ID NO: 60). The amino acid sequences of 4CL from plants contain a total of five conserved Cys residues.

Despite recognition of these key enzymes in lignin biosynthesis, there continues to be a need to develop an improved method to simultaneously control the lignin quantity, lignin compositions, and cellulose contents in plants by introducing multiple genes into plant cells.

BRIEF SUMMARY OF THE INVENTION

The invention provides a method of introducing two or more genes involved in lignin biosynthesis present in one or more independent vectors into plant cells. The method of the invention suitably employs an *Agrobacterium*-mediated or another gene delivery system by which multiple genes together with a single selectable marker gene are simultaneously transferred and inserted into the genome of plants with high frequencies.

If an *Agrobacterium*-mediated gene delivery system is used, each gene of interest is present in a binary vector that has been introduced into *Agrobacterium* to yield an isolated *Agrobacterium* strain comprising the binary vector. Moreover, more than one gene of interest may be present in each binary vector. Plant materials comprising plant cells, e.g., plant seed, plant parts or plant tissue including explant materials such as leaf discs, from a target plant species are suitably inoculated with at least two, preferably at least three, and more preferably at least four or more, of the isolated *Agrobacterium* strains, each containing a different gene of interest. A mixture of the strains is suitably contacted with plant cells. At least one of the binary vectors in the isolated *Agrobacterium* strains contains a marker gene, and any marker gene encoding a trait for selecting transformed cells from non-transformed cells may be used. Transformed plant cells are regenerated to yield a transgenic plant, the genome of which is augmented with DNA from at least two, preferably at least three, and more preferably at least four, and even more preferably at least five of the binary vectors.

The method of the invention is thus applicable to all plant species that are susceptible to the transfer of genetic information by *Agrobacterium* or other gene delivery system. Suitable plant species useful in the method of the invention include agriculture and forage crops, as well as monocots. In particular, plant species useful in the method of the invention include trees, e.g., angiosperms and gymnosperms, and more suitably a forest tree, but are not limited to the tree.

The method of the invention is suitably employed to enhance a desired agronomic trait by altering the expression of two or more genes. Such traits include alterations in lignin biosynthesis (e.g., reduction, augmentation and/or structural changes), cellulose biosynthesis (e.g., augmentation, reduction, and/or quality including high degree of polymerization and crystallinity), growth, wood quality (e.g., high density, low juvenile wood, high mature wood, low reaction wood, desirable fiber angle), stress resistance (e.g., cold-, heat-, and salt-tolerance, pathogen-, insect- and other disease-resistance, herbicide-resistance), sterility, high grain yield (for forage and food crops), and increased nutrient level.

Thus, the present invention advantageously provides gymnosperm and angiosperm plants with decreased lignin content, increased syringyl/guaiacyl (S/G) lignin ratio and increased cellulose content in which a single trait or multiple traits are changed.

In another aspect, the invention provides gymnosperm plants with syringyl enriched lignin and/or increased lignin content and/or increased syringyl/guaiacyl (S/G) lignin ratio.

Similarly, the present invention also provides angiosperm plants with increased lignin content.

Other advantages and a fuller appreciation of specific attributes and variations of the invention will be gained upon an examination of the following detailed description of exemplary embodiments and the like in conjunction with the appended claims.

BRIEF DESCRIPTION OF THE DRAWING(S)

FIG. 2 is the SAD polynucleotide DNA sequence (SEQ ID NO: 1) and the SAD amino acid sequence (SEQ ID NO: 2) respectively FIGS. 2A and 2B;

FIG. 3 is the CAld5H polynucleotide DNA sequence (SEQ ID NO: 3) and the CAld5H amino acid sequence (SEQ ID NO: 4) respectively FIGS. 3A and 3B;

FIG. 4 is the AldOMT polynucleotide DNA sequence (SEQ ID NO: 5) and the AldOMT amino acid sequence (SEQ ID NO: 6) respectively FIGS. 4A and 4B;

FIG. 5 is the 4CL polynucleotide DNA sequence (SEQ ID NO: 7) and the 4CL amino acid sequence (SEQ ID NO: 10) respectively FIGS. 5A and 5B;

FIG. 6 is the CAD polynucleotide DNA sequence (SEQ ID NO: 8) and the CAD amino acid sequence (SEQ ID NO: 9) respectively FIGS. 6B and 6A;

FIG. 7 is a map of the DNA construct, pBKPpt$_{4CL}$ Pt4CL1-a, positioned in a plant transformation binary vector.

FIG. 8 is a map of the DNA construct, pBKPpt$_{4CL}$ PtCAld5H-s, positioned in a plant transformation binary vector.

FIG. 9 is the protein sequence alignment of AldOMTs for representative species of Plants, including Aspen X62096 (SEQ ID NO: 6).

FIG. 10 is the protein sequence alignment of CADs for representative species of plants, including Aspen AF217957 (SEQ ID NO: 9).

FIG. 11 is the protein sequence alignment of CAld5Hs for representative species of plants, including Aspen (SEQ ID NO: 4).

FIG. 12 is the protein sequence alignment of 4CLs for representative species of plants, including Aspen AF041049 (SEQ ID NO: 10).

Figure 1:
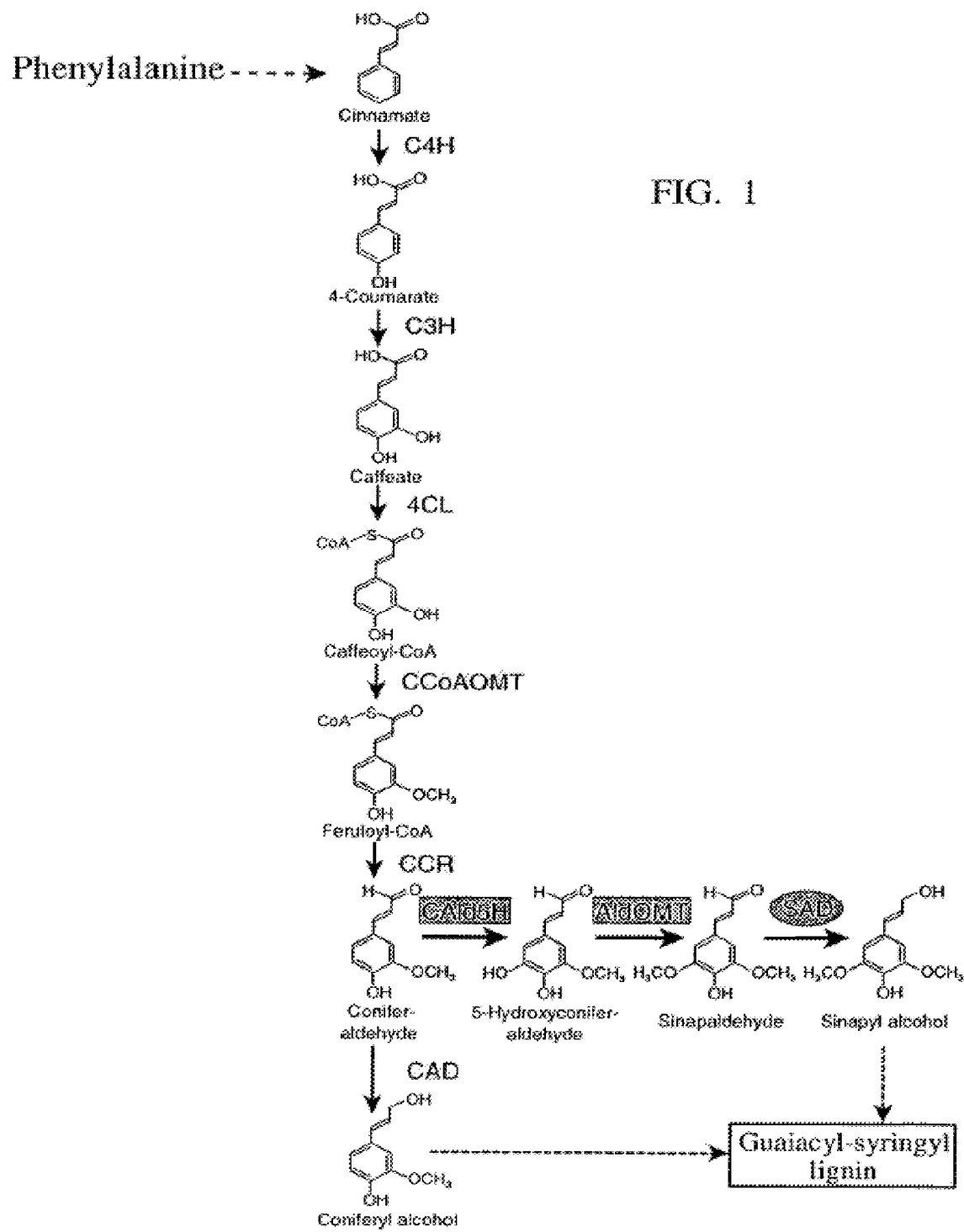
FIG. 1 is a schematic representation of plant monolignol pathways for production of coniferyl alcohol and sinapyl alcohol.

It is expressly understood that the figures of the drawing are for the purposes of illustration and description only and are not intended as a definition of the limits of the invention.

DETAILED DESCRIPTION OF THE INVENTION

The present invention provides a method and DNA constructs useful for the transformation of plant tissue for the alteration of lignin monomer composition, increased syringyl/guaiacyl (S/G) lignin ratio and increased cellulose content and transgenic plants resulting from such transformations. The present invention is of particular value to the paper and pulp industries because lignin containing higher syringyl monomer content is more susceptible to chemical delignification. Woody plants transformed with the DNA constructs provided herein offer a significant advantage in the delignification process over conventional paper feedstocks. Similarly, modification of the lignin composition in grasses by the insertion and expression of a heterologous SAD gene offers a unique method for increasing the digestibility of grasses and is of significant potential economic benefit to the farm and agricultural industries.

The terms used in this specification generally have their ordinary meanings in the art, within the context of the invention and in the specific context where each term is used.

Certain terms are discussed below, or elsewhere in the specification, to provide additional guidance to the person of skill in the art in describing the compositions and methods of the invention and how to make and use them. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to the preferred embodiments.

As used herein, "gene" refers to a nucleic acid fragment that expresses a specific protein including the regulatory sequences preceding (5' noncoding) and following (3' noncoding) the coding region or coding sequence (See, below). "Native" gene refers to the gene as found in nature with its own regulatory sequences.

"Endogenous gene" refers to the native gene normally found in its natural location in the genome.

"Transgene" refers to a gene that is introduced by gene transfer into the host organism.

"Coding sequence" or "Coding Region" refers to that portion of the gene that contains the information for encoding a polypeptide. The boundaries of the coding sequence are determined by a start codon at the 5' (amino) terminus and a translation stop codon at the 3' (carboxyl) terminus. A coding sequence can include, for example, prokaryotic sequences, cDNA from eukaryotic mRNA, genomic DNA, and even synthetic DNA sequences.

"Promoter" or "Promoter Sequence" refers to a DNA sequence, in a given gene, which sequence controls the expression of the coding sequence by providing the recognition site for RNA polymerase and other factors required for proper transcription. Most genes have regions of DNA sequence that are promoter sequences which regulate gene expression. Promoter regions are typically found in the 5' flanking DNA sequence upstream from the coding sequence in both prokaryotic and eukaryotic cells. A promoter sequence provides for regulation of transcription of the downstream gene sequence and typically includes from about 50 to about 2000 nucleotide base pairs. Promoter sequences also contain regulatory sequences such as enhancer sequences that can influence the level of gene expression. Some isolated promoter sequences can provide for gene expression of heterologous DNAs, that is DNA different from the natural homologous DNA. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. An isolated promoter sequence that is a strong promoter for heterologous DNAs is advantageous because it provides for a sufficient level of gene expression to allow for easy detection and selection of transformed cells, and provides for a high level of gene expression when desired. A promoter may also contain DNA sequences that are involved in the binding of protein factors which control the effectiveness of transcription initiation in response to physiological or developmental conditions.

"Regulatory sequence(s)" refers to nucleotide sequences located upstream (5'), within, and/or downstream (3') of a coding sequence, which control the transcription and/or expression of the coding sequences in conjunction with the protein biosynthetic apparatus of the cell. Regulatory sequences include promoters, translation leader sequences, transcription termination sequences and polyadenylation sequences.

"Encoding" and "coding" refer to the process by which a gene, through the mechanisms of transcription and translation, provides the information to a cell from which a series of amino acids can be assembled into a specific amino acid sequences to produce an active enzyme. It is understood that the process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequences, such as deletions, insertions or substitutions in the sequence which produce silent changes that do not substantially affect the functional properties of the resulting protein molecule are also contemplated. For example, alterations in the gene sequence which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence to study the effect of retention of biological activity of the protein. Each of these proposed modifications is well within the routine skill in the art, as is the determination of retention of biological activity in the encoded products. Moreover, the skilled artisan recognizes that sequences encompassed by this invention are also defined by their ability to hybridize, under stringent condition, with the sequences exemplified herein.

"Expression" is meant to refer to the production of a protein product encoded by a gene. "Overexpression" refers to the production of a gene product in transgenic organisms that exceed levels of production in normal or non-transformed organisms.

"Functional portion" or "functional fragment" or "functional equivalents" of an enzyme is that portion, fragment or equivalent section which contains the active site for binding one or more reactants or is capable of improving or regulating the rate of reaction. The active site may be made up of separate portions present on one or more polypeptide chains and will generally exhibit high substrate specificity.

"Enzyme encoded by a nucleotide sequence" includes enzymes encoded by a nucleotide sequence which includes partial isolated DNA sequences.

"Transformation" refers to the transfer of a foreign gene into the genome of a host organism and its genetically stable inheritance.

"% identity" refers to the percentage of the nucleotides/ amino acids of one polynucleotide/polypeptide that are identical to the nucleotides/amino acids of another sequence of polynucleotide/polypeptide as identified by a program such as GAP from Genetics Computer Group Wisconsin (GCG) package (version 9.0) (Madison, Wis.). GAP uses the algorithm of Needleman and Wunsch (J. Mol. Biol. 48: 443-453, 1970) to find the alignment of two complete sequences that maximizes the number of matches and minimizes the number of gaps. When parameters required to run the above algorithm are not specified, the default values offered by the program are contemplated.

"Substantial homology" or "substantial similarity" refers to a 70% or more similarity or 70% homology wherein "% similarity" or "% homology" between two polypeptide sequences is a function of the number of similar positions shared by two sequences on the basis of the scoring matrix used divided by the number of positions compared and then multiplied by 100. This comparison is made when two sequences are aligned (by introducing gaps if needed) to determine maximum homology. The PowerBlast program, implemented by the National Center for Biotechnology Information, can be used to compute optimal, gapped alignments. GAP program from Genetics Computer Group Wisconsin package (version 9.0) (Madison, Wis.) can also be used.

"Lignin monomer composition" refers to the relative ratios of guaiacyl monomer and syringyl monomer found in lignified plant tissue.

"Plant" includes whole plants and portions of plants, including plant organs (e.g., roots, stems, leaves, etc).

"Angiosperm" refers to plants that produce seeds encased in an ovary. A specific example of an angiosperm is *Liquidambar styraciflua* (L.) [sweetgum].

"Gymnosperm" refers to plants that produce naked seeds, i.e., seeds that are not encased in an ovary. A specific example of a gymnosperm is *Pinus taeda* (L.) [loblolly pine].

As used herein, the terms "isolated and/or purified" with reference to a nucleic acid molecule or polypeptide refer to in vitro isolation of a nucleic acid or polypeptide molecule from its natural cellular environment, and from association with other components of the cell, such as nucleic acid or polypeptide, so that it can be sequenced, replicated and/or expressed.

An "isolated" strain of *Agrobacterium* refers to cells derived from a clone of *Agrobacterium* that is transformed in vitro with an isolated binary vector.

A "vector" is a recombinant nucleic acid construct, such as plasmid, phage genome, virus genome, cosmid, or artificial chromosome to which a polynucleotide in accordance with the invention may be attached. In a specific embodiment, the vector may bring about the replication of the attached segment, e.g., in the case of a cloning vector.

"Sinapyl alcohol dehydrogenase" or "SAD", coniferyl alcohol dehydrogenase or "CAD", coniferaldeyde 5-hydroxylase or "CAld5H", 5-hydroxyconiferaldehyde O-methyltransferase or "AldOMT", and 4-coumarate-CoA ligase or "4CL" refer to enzymes in the plant phenylpropanoid biosynthetic pathway. In the illustrated embodiments of the present invention, the DNA sequences encoding these enzymes were identified from quaking aspen *Populus tremuloides*. It is understood that each sequence can be used as a probe to clone its equivalent from any plant species by techniques (EST, PCR, RT-PCR, antibodies, etc.) well known in the art.

The Phenyl Propanoid Biosynthetic Pathway

Reference is made to FIG. 1 which shows different steps in the biosynthetic pathways from 4-coumarate (1) to guaiacyl (coniferyl alcohol (6)) and syringyl (sinapyl alcohol (9)) monolignols for the formation of guaiacyl-syringyl lignin together with the enzymes responsible for catalyzing each step. The enzymes indicated for each of the reaction steps are: 4-coumaric acid 3-hydroxylase (C3H) which converts 4-coumarate (1) to caffeate (2); 4-coumarate-CoA ligase (4CL) converts caffeate (2) to caffeoyl CoA (3) which in turn is converted to feruloyl CoA (4) by caffeoyl-CoA O-methyltransferase (CCoAOMT); cinnamoyl-CoA reductase (CCR) converts feruloyl CoA (4) to coniferaldehyde (5); coniferyl alcohol dehydrogenase (CAD) converts coniferaldehyde (5) to the guaiacyl monolignol coniferyl alcohol (6); at coniferaldehyde (5), the pathway splits wherein coniferaldehyde (5) can also be converted to 5-hydroxyconiferaldehyde (7) by coniferaldeyde 5-hydroxylase (Cald5H); 5-hydroxyconiferaldehyde O-methyltransferase (AldOMT) converts 5-hydroxconiferaldehyde (7) to sinapaldehyde (8) which, in turn, is converted to the syringyl monolignol, sinapyl alcohol (9) by sinapyl alcohol dehydrogenase (SAD).

DNA Constructs

According to the present invention, a DNA construct is provided which is a plant DNA having a promoter sequence, a coding region and a terminator sequence. The coding region encodes a combination of enzymes essential to lignin biosynthesis, specifically, SAD, CAD, Cald5H, AldOMT, and 4CL protein sequences, substantially similar sequences, or functional fragments thereof. The coding region is suitably a minimum size of 50 bases. The gene promoter is positioned at the 5'-end of a transgene (e.g., 4CL alone or together with SAD, Cald5H, and AldOMT, and combinations thereof, or 4CL and CAD alone, or together with CAld5H, SAD, and AldOMT, and combinations thereof, as described hereinafter) for controlling the transgene expression, and a gene termination sequence that is located at the 3'-end of the transgene for signaling the end of the transcription of the transgene.

The DNA construct in accordance with the present invention can be incorporated into the genome of a plant by transformation to alter lignin biosynthesis, increase syringyl/guaiacyl (S/G) lignin ratio and increase cellulose content. The DNA construct may include clones of CAld5H, SAD, AldOMT, CAD, and 4CL, and variants thereof such as are permitted by the degeneracy of the genetic code and the functional equivalents thereof.

The DNA constructs of the present invention may be inserted into plants to regulate production the following enzymes: CAld5H, SAD, AldOMT, CAD, and 4CL. Depending on the nature of the construct, the production of the protein may be increased or decreased, either throughout or at particular stages in the life of the plant, relative to a similar control plant that does not incorporate the construct into its genome. For example, the orientation of the DNA coding sequence, promoter, and termination sequence can serve to either suppress lignin formation or amplify lignin formation. For the down-regulation of lignin synthesis, the DNA is in the antisense orientation. For the amplification of lignin biosynthesis, the DNA is in the sense orientation, thus to provide one or more additional copies of the DNA in the plant genome. In this case, the DNA is suitably a full-length cDNA copy. It is also possible to target expression of the gene to specific cell types of the plants, such as the epidermis, the xylem, the roots, etc. Constructs in accordance with the present invention may be used to transform cells of both monocotyledons and dicotyledons plants in various ways known in the art. In many cases, such plant cells may be cultured to regenerate whole plants which subsequently reproduce to give successive generations of genetically modified plants. Examples of plants that are suitably genetically modified in accordance with the present invention, include but are not limited to, trees such a aspen, poplar, pine and eucalyptus.

Promoters and Termination Sequences

Various gene promoter sequences are well known in the art and can be used in the DNA constructs of present invention. The promoter in the constructs in accordance with the present invention suitably provides for expression of the linked DNA segment. The promoter can also be inducible so that gene expression can be turned on or off by an exogenously added agent. It may also be preferable to combine the desired DNA segment with a promoter that provides tissue specific expression or developmentally regulated gene expression in plants.

The promoter may be selected from promoters known to operate in plants, e.g., CaMV35S, GPAL2, GPAL3 and endogenous plant promoter controlling expression of the enzyme of interest. Use of a constitutive promoter such as the CaMV35S promoter (Odell et al. 1985), or CaMV 19S (Lawton et al., 1987) can be used to drive the expression of the transgenes in all tissue types in a target plant. Other promoters are nos (Ebert et al. 1987), Adh (Walker et al., 1987), sucrose synthase (Yang et al., 1990), Δ-tubulin, ubiquitin, actin (Wang et al., 1992), cab (Sullivan et al., 1989), PEPCase (Hudspeth et al., 1989) or those associate with the R gene complex (Chandler et al., 1989). On the other hand, use of a tissue specific promoter permits functions to be controlled more selectively. The use of a tissue-specific promoter has the advantage that the desired protein is only produced in the tissue in which its action is required. Suitably, tissue-specific promoters, such as those would confine the expression of the transgenes in developing xylem where lignification occurs, may be used in the inventive DNA constructs.

A DNA segment can be combined with the promoter by standard methods as described in Sambrook et al., 2nd ed. (1982). Briefly, a plasmid containing a promoter such as the CaMV 35S promoter can be constructed as described in Jefferson (1987) or obtained from Clontech Lab, Palo Alto, Calif. (e.g., pBI121 or pBI221). Typically, these plasmids are constructed to provide for multiple cloning sites having specificity for different restriction enzymes downstream from the promoter. The DNA segment can be subcloned downstream from the promoter using restriction enzymes to ensure that the DNA is inserted in proper orientation with respect to the promoter so that the DNA can be expressed.

The gene termination sequence is located 3' to the DNA sequence to be transcribed. Various gene termination sequences known in the art may be used in the present inventive constructs. These include nopaline synthase (NOS) gene termination sequence (see, e.g., references cited in co-pending, commonly-owned PCT application, PCT/US/0027704, filed Oct. 6, 2000, entitled "Method of Introducing a Plurality of Genes into Plants," incorporated herein by reference.)

Marker Genes

A marker gene may also be incorporated into the inventive DNA constructs to aid the selection of plant tissues with positive integration of the transgene. "Marker genes" are genes that impart a distinct phenotype to cells expressing the marker gene, and thus, allow such transformed cells to be distinguished from cells that do not have the marker. Many examples of suitable marker genes are known to the art and can be employed in the practice of the invention, such as neomycin phosphotransferase II (NPT II) gene that confers resistance to kanamycin or hygromycin antibiotics which would kill the non-transformed plant tissues containing no NPT II gene (Bevan et al., 1983). Numerous other exemplary marker genes used in the method, in accordance with the present invention are listed in Table 1 of co-pending, commonly owned of PCT/US/0027704, filed Oct. 6, 2000, entitled "Method of Introducing a Plurality of Genes into Plants," incorporated herein by reference.

Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant.

Optional Sequences in the Expression Cassette

The expression cassette containing DNA sequences in accordance with the present invention can also optionally contain other DNA sequences. Transcription enhancers or duplications of enhancers can be used to increase expression from a particular promoter. One may wish to obtain novel tissue-specific promoter sequences for use in accordance with the present invention. To achieve this, one may first isolate cDNA clones from the tissue concerned and identify those clones which are expressed specifically in that tissue, for example, using Northern blotting. Ideally, one would like to identify a gene that is not present in a high copy number, but which gene product is relatively abundant in specific tissues. The promoter and control elements of corresponding genomic clones may then be localized using the techniques of molecular biology known to those of skill in the art.

Expression of some genes in transgenic plants will occur only under specified conditions. It is known that a large number of genes exist that respond to the environment. In some embodiments of the present invention expression of a DNA segment in a transgenic plant will occur only in a certain time period during the development of the plant. Developmental timing is frequently correlated with tissue specific gene expression.

As the DNA sequence inserted between the transcription initiation site and the start of the coding sequence, i.e., the untranslated leader sequence, can influence gene expression, one can also employ a particular leader sequence. Preferred leader sequence include those which comprise sequences selected to direct optimum expression of the attached gene, i.e., to include a preferred consensus leader sequence which can increase or maintain mRNA stability and prevent inappropriate initiation of translation (Joshi, 1987). Such sequences are known to those of skill in the art. Sequences that are derived from genes that are highly expressed in plants will be most preferred.

Additionally, expression cassettes can be constructed and employed to target the gene product of the DNA segment to an intracellular compartment within plant cells or to direct a protein to the extracellular environment. This can generally be achieved by joining a DNA sequence encoding a transit or signal peptide sequence to the coding sequence of the DNA segment. Also, the DNA segment can be directed to a particular organelle, such as the chloroplast rather than to the cytoplasm.

Alternatively, the DNA fragment coding for the transit peptide may be chemically synthesized either wholly or in part from the known sequences of transit peptides such as those listed above. The description of the optional sequences in the expression cassette, is commonly owned, co-pending PCT/US/0027704, filed Oct. 6, 2000, entitled "Method of Introducing a Plurality of Genes into Plants," incorporated herein by reference.

Transformation

Transformation of cells from plants, e.g., trees, and the subsequent production of transgenic plants using e.g., *Agro-* bacterium-mediated transformation procedures known in the art, and further described herein, is one example of a method for introducing a foreign gene into plants. Although, the method of the invention can be performed by other modes of transformation, Agrobacterium-mediated transformation procedures are cited as examples, herein. For example, transgenic plants may be produced by the following steps: (i) culturing Agrobacterium in low-pH induction medium at low temperature and preconditioning, i.e., coculturing bacteria with wounded tobacco leaf extract in order to induce a high level of expression of the Agrobacterium vir genes whose products are involved in the T-DNA transfer; (ii) coculturing desired plant tissue explants, including zygotic and/or somatic embryo tissues derived from cultured explants, with the incited Agrobacterium; (iii) selecting transformed callus tissue on a medium containing antibiotics; and (iv) converting the embryos into platelets.

Any non-tumorigenic A. tumefaciens strain harboring a disarmed Ti plasmid may be used in the method in accordance with the invention. Any Agrobacterium system may be used. For example, Ti plasmid/binary vector system or a cointegrative vector system with one Ti plasmid may be used. Also, any marker gene or polynucleotide conferring the ability to select transformed cells, callus, embryos or plants and any other gene, such as for example a gene conferring resistance to a disease, or one improving lignin content or structure or cellulose content, may also be used. A person of ordinary skill in the art can determine which markers and genes are used depending on particular needs.

To increase the infectivity of the bacteria, Agrobacterium is cultured in low-pH induction medium, i.e., any bacterium culture media with a pH value adjusted to from 4.5 to 6.0, most preferably about 5.2, and at low temperature such as for example about 19-30° C., preferably about 21-26° C. The conditions of low-pH and low temperature are among the well-defined critical factors for inducing virulence activity in Agrobacterium (e.g., Altmorbe et al., 1989; Fullner et al., 1996; Fullner and Nester, 1996).

The bacteria is preconditioned by coculturing with wounded tobacco leaf extract (prepared according to methods known generally in the art) to induce a high level of expression of the Agrobacterium vir genes. Prior to inoculation of plant somatic embryos, Agrobacterium cells can be treated with a tobacco extract prepared from wounded leaf tissues of tobacco plants grown in vitro. To achieve optimal stimulation of the expression of Agrobacterium vir genes by wound-induced metabolites and other cellular factors, tobacco leaves can be wounded and pre-cultured overnight. Culturing of bacteria in low pH medium and at low temperature can be used to further enhance the bacteria vir gene expression and infectivity. Preconditioning with tobacco extract and the vir genes involved in the T-DNA transfer process are generally known in the art.

Agrobacterium treated as described above is then cocultured with a plant tissue explant, such as for example, zygotic and/or somatic embryo tissue. Non-zygotic (i.e., somatic) or zygotic tissues can be used. Any plant tissue may be used as a source of explants. For example, cotyledons from seeds, young leaf tissue, root tissues, parts of stems including nodal explants, and tissues from primary somatic embryos such as the root axis may be used. Generally, young tissues are a preferred source of explants.

The above-described transformation and regeneration protocol is readily adaptable to other plant species. Other published transformation and regeneration protocols for plant species include Danekar et al., 1987; McGranahan et al., 1988; McGranahan et al., 1990; Chen, Ph.D. Thesis, 1991; Sullivan et al., 1993; Huang et al., 1991; Wilde et al., 1992; Minocha et al., 1986; Parsons et al., 1986; Fillatti et al., 1987; Pythoud et al., 1987; De Block, 1990; Brasileiro et al., 1991; Brasileiro et al., 1992; Howe et al., 1991; Klopfenstein et al., 1991; Leple et al., 1992; and Nilsson et al., 1992.

Characterization

To confirm the presence of the DNA segment(s) or "transgene(s)" in the regenerated plants, a variety of assays may be performed. Such assays include, for example, "molecular biological" assays well known to those of skill in the art, such as Southern and Northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

1. DNA Integration, RNA Expression and Inheritance

Genomic DNA may be isolated from callus cell lines or any plant parts to determine the presence of the DNA segment through the use of techniques well known to those skilled in the art. Note that intact sequences will not always be present, presumably due to rearrangement or deletion of sequences in the cell.

The presence of DNA elements introduced through the methods of this invention may be determined by polymerase chain reaction (PCR). Using this technique, discreet fragments of DNA are amplified and detected by gel electrophoresis. This type of analysis permits one to determine whether a DNA segment is present in a stable transformant, but does not prove integration of the introduced DNA segment into the host cell genome. In addition, it is not possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced DNA segment.

Positive proof of DNA integration into the host genome and the independent identities of transformants may be determined using the technique of Southern hybridization. Using this technique, specific DNA sequences that were introduced into the host genome and flanking host DNA sequences can be identified. Hence the Southern hybridization pattern of a given transformant serves as an identifying characteristic of that transformant. In addition, it is possible through Southern hybridization to demonstrate the presence of introduced DNA segments in high molecular weight DNA, i.e., confirm that the introduced DNA segment has been integrated into the host cell genome. The technique of Southern hybridization provides information that is obtained using PCR, e.g., the presence of a DNA segment, but also demonstrates integration into the genome and characterizes each individual transformant.

It is contemplated that by using the techniques of dot or slot blot hybridization which are modifications of Southern hybridization techniques, one could obtain the same information that is derived from PCR, e.g., the presence of a DNA segment.

Both PCR and Southern hybridization techniques can be used to demonstrate transmission of a DNA segment to progeny. In most instances the characteristic Southern hybridization pattern for a given transformant will segregate in progeny as one or more Mendelian genes (Spencer et al., 1992; Laursen et al., 1994) indicating stable inheritance of the gene.

Whereas DNA analysis techniques may be conducted using DNA isolated from any part of a plant, RNA may only be expressed in particular cells or tissue types, and hence, it will be necessary to prepare RNA for analysis from these tissues. PCR techniques may also be used for detection and quantitation of RNA produced from introduced DNA segments. In this application of PCR, it is first necessary to reverse transcribe RNA into DNA, using enzymes such as reverse transcriptase, and then through the use of conventional PCR techniques amplify the DNA. In most instances, PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and demonstrate only the presence or absence of an RNA species.

2. Gene Expression

While Southern blotting and PCR may be used to detect the DNA segment in question, they do not provide information as to whether the DNA segment is being expressed. Expression may be evaluated by specifically identifying the protein products of the introduced DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focussing, or by chromatographic techniques such as ion exchange or gel exclusion chromatography. The unique structures of individual proteins also offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabelled acetylated phosphinothricin from phosphinothricin.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of DNA segments encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

The invention will be further described by the following non-limiting examples.

EXAMPLE 1

Preparation of Transgenic Aspen

Construction of Binary Vectors pBKPpt.sub.4CL Pt4CL1-a: Aspen 4CL1 xylem specific promoter (Ppt$_{4CL}$, 1.1 kb, GenBank AF041051 was prepared and linked to aspen 4CL1 cDNA (Pt4CL1, GenBank AF041049, SEQ ID NO: 10) which was orientated in the antisense direction. Then the cassette containing aspen 4CL1 promoter and antisense aspen 4CL1 cDNA was positioned in a plant transformation binary vector, as shown in FIG. 1. (pBKPpt.sub.4CL Pt4CL1-a construct).

pBKPpt$_{4cl}$ PtCAld5H-s: From pBKPpt$_{4CL}$ Pt4CL-a construct, the antisense Pt4CL1 was replaced with PtCAld5H cDNA (SEQ ID NO: 3) in a sense orientation, yielding a pBKPpt$_{4CL}$ PtCAld5H-s transformation binary construct, as shown in FIG. 2.

Also, Example 1 of PCT application PCT/US/0027704, filed Oct. 6, 2000, entitled "Method of Introducing a Plurality of Genes into Plants," incorporated herein by reference, describes a number of other gene constructs for preparing transgenic plants. The plants are transformed with a genes from the phenylpropanoid pathway (i.e., 4CL, AEOMT, CoAOMT, and CAld5H) using an operably linked to either a homologous or a heterologous and either a constitutive or tissue-specific promoter Incorporation of Binary Vector into *Agrobacterium*

According to the protocol described in Tsai et al. (1994, Plant Cell Reports, 14:94-97) *Agrobacterium* C58/pMP90 strain was grown in LB with selection of gentamicin at 28° C. overnight. Cells were harvested by centrifugation at 10,000 rpm for 10 minutes at 4° C. The cell pellet was washed with 0.5 volume of ice-cold 20 mM $CaCl_2$, and centrifuged again. The cells were then resuspended in 0.1 volume of ice-cold 20 mM $CaCl_2$ in a sample tube. About 1 µg of binary vector DNA was added to 200 µL of the cell suspension and mixed by pipetting. The sample tube was chilled in liquid $N_2$ for 5 minutes and thawed at 37° C. in a water bath for 5 minutes. One mL of LB medium was added and the mixture was incubated at 28° C. for 3 hours with gentle shaking. Twenty µL of the cells were spread onto a LB plate containing 25 µg/mL gentamicin and 50 µg/mL kanamycin and incubated at 28° C. for 2 days. PCR (amplification conditions, cycling parameters and primers are described below) was used to verify the presence of DNA from the vector in the transformed colonies.

Simultaneous Transformation of Aspen with Multiple Genes Via Engineered *Agrobacterium* Strains For simultaneous transformation of multiple genes, pBKPpt$_{4cl}$ Pt4CL-a and pBKPpt$_{4cl}$ PtCal5H *Agrobacterium* clones were cultured in LB medium at 28° C. overnight separately. The *Agrobacterium* strains were subcultured individually by a 100-fold dilution into 50 mL of LB (pH 5.4) containing 50 µg/mL kanamycin, 25 µg/mL gentamycin and 20 µM acetosyringone (in DMSO), and grown overnight at 28° C. with shaking. An equal volume of the same density of individually cultured *Agrobacterium* strains was then mixed.

Leaves excised from sterile tobacco plants were cut into pieces with a size of about 5 mm² and the leaf discs were then immersed in the *Agrobacterium* mixture for 5 minutes.

After removing excess *Agrobacterium* cells, the treated leaf discs were placed on callus induction medium (WPM: Woody Plant Medium, BA: 6-benzyladenine+2,4-D: 2,4-dichlorophenoxyacetic acid; Tsai et al. 1994, Plant Cell Reports, 14:94-97) and cultured for 2 days. Then, the pre-cultured leaf discs were rinsed with sterile water several times to remove the *Agrobacterium* cells and washed in 1 mg/mL claforan and 1 mg/mL ticarcillin with shaking for 3 hours to kill *Agrobacterium*. After briefly blot-drying, the pre-cultured and washed leaf discs were cultured on callus induction medium containing 50 µg/mL kanamycin and 300 µg/mL claforan for selection of transformed cells. After 2 to 3 subcultures (10 days/subculture), the calli grown on the leaf discs were excised and transferred onto shoot induction medium (WPM+ TDZ: N-phenyl-N'-1,2,3-thiadiazol-5-yl-urea) containing 50 µg/ml kanamycin and 300 µg/ml claforan for regenerating shoots. After shoots were grown to about 0.5 cm high, they excised and planted to rooting media (WPM with kanamycin and claforan). Whole plants about 7 cm high were transplanted into soil and maintained in a greenhouse for subsequent molecular characterization.

Genomic DNA Isolation

Genomic DNA was isolated according to Hu et al. (1998). About 100 mg of young leaves were collected from each plant growing in the greenhouse and ground in liquid $N_2$ to fine powder for DNA isolation using QIAGEN plant DNA isolation kit (Valencia, Calif.). Specifically, the powdered tissue was added to extract buffer containing 2% hexadecyltrimethylammonium bromide (CTAB), 100 mM Tris-HCl, pH 8.0, 20 mM EDTA, 1.4 M NaCl and 30 mM β-mercaptoethanol at 5 mL/g tissue. The extraction mixture was incubated in a tube at 60° C. for 1 hour with occasional shaking. One volume of chloroform-isoamyl alcohol (24:1) was added and mixed gently. The two phases were separated by centrifugation at 10,000×g for 10 minutes. The aqueous phase was transferred to a new tube and extracted with chloroform in the presence of 1% CTAB and 0.7 M NaCl. The DNA was precipitated by addition of ⅔ volume of isopropanol (−20° C.) and kept at −20° C. for 20 minutes. Following the centrifugation at 10,000×g for 10 minutes, the pelleted DNA was washed with 70% ethanol-10 mM ammonia acetate. Then the pellet was dissolved in 2 mL TE buffer (10 mM Tris-HCl/0.1 mM EDTA, pH 8) and treated with 2 µg RNase A at 37° C. for 20 minutes. The DNA was precipitated by addition of 2 mL of 5 M ammonia acetate and 10 mL of 95% ethanol at −20° C. for 20 minutes. After centrifugation, the pellet was washed with 70% ethanol. After a brief drying, genomic DNA was dissolved in TE buffer.

PCR Verification of Foreign Gene Insertion in Host Plant Genome

PCR was used to verify the integration of the gene constructs in the genome of transgenic plants. Two specific primers were synthesized for each construct and used to PCR-amplify the corresponding construct in genome of transgenic Aspen. For the pBKPpt$_{4CL}$ Pt4CL1-a construct, two specific primers were synthesized that amplify a 4CL cDNA fragment. Pt4CL1 promoter sense primer (5'CAGGAATGCTCTGCACTCTG3') (SEQ ID NO:11) and Pt4CL1 sense primer (5'ATGAATCCACAAGAATTCAT3') (SEQ ID NO:12) at the translation start region. Primers for PCR verification of pBKPpt$_{4CL}$ PtCald5H-s construct are Pt4CL1 promoter sense primer (5'CAGGAATGCTCTGCACTCTG3') (SEQ ID NO:13) and PtCald5H antisense primer (5'TTAGAGAGGACAGAGCACACG3') (SEQ ID NO:14) at translation stop region.

The PCR reaction mixture contained 100 ng genomic DNA of transformed aspen, and 0.2 µM of each primer, 100 µM of each deoxyribonucleotide triphosphate, 1×PCR buffer and 2.5 Units of Taq DNA polymerase (Promega Madison, Wis.) in a total volume of 50 µL. The cycling parameters were as follows: 94° C. for 1 minute, 56° C. for 1 minute (for 4CL and CAld5H or can vary between cDNA templates used) according to different gene checked) and 72° C. for 2 minute, for 40 cycles, with 5 minutes at 72° C. extension. The PCR products were electrophoresized on a 1% agarose gel.

EXAMPLE 2

Preparation of Other Transgenic Plants

It is important to recognize that there is a substantial percentage of sequence homology among the plant genes involved in the lignin biosynthetic pathway, discussed herein. This substantial sequence homology allows the method in accordance with the invention disclosed herein to be applicable to all plants that possess the requisite genes involved in the lignin biosynthetic pathway. To demonstrate the substantial sequence homology among plant genes, the percentage sequence homology is set forth in tabular form, for example, CAld5H genes (Table 1), AldOMT genes (Table 2), CAD genes (Table 3), and 4CL genes (See FIG. 12). Therefore, it is possible to alter lignin monomer composition, increase S/G lignin ratio, and increase cellulose content in all plants by using the method in accordance with the invention, described herein.

TABLE 1

Protein sequence homology (%) of plant Coniferyl Aldehyde 5-hydroxylase (CAld5H) from 1) Aspen, SEQ ID NO: 4; 2) Poplar, AJ010324, SEQ ID NO: 40; 3) Sweetgum, AF139532, SEQ ID NO: 41; 4) Arabidopsis, U38416, SEQ ID NO: 42 (Ferulic Acid 5-hydroxylase, F5H).

|   | 1 | 2 | 3 | 4 |
|---|---|---|---|---|
| 1 |   |   |   |   |
| 2 | 99 |   |   |   |
| 3 | 84 | 84 |   |   |
| 4 | 81 | 83 | 83 |   |

TABLE 2

Protein sequence homology (%) of plant AldOMTs from 1) Aspen, X62096, SEQ ID NO: 6; 2) Poplar, M73431, SEQ ID NO: 15; 3) Almond, X83217, SEQ ID NO: 16; 4) Strawberry, AF220491, SEQ ID NO: 17; 5) Alfalfa, M63853, SEQ ID NO: 18; 6) Eucalyptus, X74814, SEQ ID NO: 19; 7) *Clarkia breweri*, AF006009, SEQ ID NO: 20 8) Sweetgum, AF139533, SEQ ID NO: 21; 9) Arabidopsis, U70424, SEQ ID NO: 22; 10) Tobacco, X74452, SEQ ID NO: 23; 11) *Vitis vinifera*, AF239740, SEQ ID NO: 24.

|   | 1 | 2 | 3 | 4 | 5 | 6 | 7 | 8 | 9 | 10 | 11 |
|---|---|---|---|---|---|---|---|---|---|----|----|
| 1 |   |   |   |   |   |   |   |   |   |    |    |
| 2 | 99 |   |   |   |   |   |   |   |   |    |    |
| 3 | 92 | 92 |   |   |   |   |   |   |   |    |    |
| 4 | 91 | 90 | 94 |   |   |   |   |   |   |    |    |
| 5 | 90 | 90 | 89 | 89 |   |   |   |   |   |    |    |
| 6 | 89 | 89 | 89 | 87 | 87 |   |   |   |   |    |    |
| 7 | 88 | 88 | 89 | 88 | 87 | 90 |   |   |   |    |    |
| 8 | 88 | 87 | 88 | 87 | 86 | 85 | 83 |   |   |    |    |
| 9 | 84 | 84 | 85 | 86 | 82 | 82 | 82 | 83 |   |    |    |

TABLE 2-continued

Protein sequence homology (%) of plant AldOMTs from 1) Aspen, X62096, SEQ ID NO: 6; 2) Poplar, M73431, SEQ ID NO: 15; 3) Almond, X83217, SEQ ID NO: 16; 4) Strawberry, AF220491, SEQ ID NO: 17; 5) Alfalfa, M63853, SEQ ID NO: 18; 6) Eucalyptus, X74814, SEQ ID NO: 19; 7) Clarkia breweri, AF006009, SEQ ID NO: 20 8) Sweetgum, AF139533, SEQ ID NO: 21; 9) Arabidopsis, U70424, SEQ ID NO: 22; 10) Tobacco, X74452, SEQ ID NO: 23; 11) Vitis vinifera, AF239740, SEQ ID NO: 24.

|    | 1  | 2  | 3  | 4  | 5  | 6  | 7  | 8  | 9  | 10 | 11 |
|----|----|----|----|----|----|----|----|----|----|----|----|
| 10 | 83 | 83 | 83 | 82 | 81 | 82 | 80 | 83 | 77 |    |    |
| 11 | 80 | 80 | 78 | 77 | 78 | 77 | 78 | 80 | 76 | 77 |    |

TABLE 3

Protein sequence homology (%) of plant CADs from 1) Aspen, AF217957, SEQ ID NO: 9; 2) Cottonwood, Z19568, SEQ ID NO: 38 and 3) Udo, D13991, SEQ ID NO: 39; 4) Tobacco, X62343, SEQ ID NO: 36; 5) Tobacco, X62344, SEQ ID NO: 37; 6) Eucalyptus, AF038561, SEQ ID NO: 34; 7) Eucalyptus, X65631, SEQ ID NO: 35; 8) Lucerne, AF083332, SEQ ID NO: 32; 9) Lucerne, Z19573, SEQ ID NO: 33 10) Maize, AJ005702, SEQ ID NO: 29; 11) Maize, Y13733, SEQ ID NO: 30; 12) Sugarcane, AJ231135, SEQ ID NO: 31; 13) Radiata pine, U62394, SEQ ID NO: 25; 14) Loblolly pine, Z37992, SEQ ID NO: 26; 15) Loblolly pine, Z37991, SEQ ID NO: 27; 16) Norway spruce, X72675. SEQ ID NO: 28.

|    | 1  | 2  | 3  | 4  | 5  | 6  | 7  | 8  | 9  | 10 | 11 | 12 | 13 | 14 | 15 | 16 |
|----|----|----|----|----|----|----|----|----|----|----|----|----|----|----|----|----|
| 1  |    |    |    |    |    |    |    |    |    |    |    |    |    |    |    |    |
| 2  | 97 |    |    |    |    |    |    |    |    |    |    |    |    |    |    |    |
| 3  | 85 | 84 |    |    |    |    |    |    |    |    |    |    |    |    |    |    |
| 4  | 82 | 82 | 84 |    |    |    |    |    |    |    |    |    |    |    |    |    |
| 5  | 80 | 80 | 81 | 94 |    |    |    |    |    |    |    |    |    |    |    |    |
| 6  | 81 | 81 | 82 | 80 | 78 |    |    |    |    |    |    |    |    |    |    |    |
| 7  | 81 | 80 | 81 | 80 | 78 | 80 |    |    |    |    |    |    |    |    |    |    |
| 8  | 79 | 79 | 80 | 80 | 79 | 79 | 79 |    |    |    |    |    |    |    |    |    |
| 9  | 79 | 80 | 80 | 79 | 78 | 78 | 79 | 99 |    |    |    |    |    |    |    |    |
| 10 | 78 | 77 | 79 | 76 | 74 | 76 | 77 | 73 | 73 |    |    |    |    |    |    |    |
| 11 | 78 | 78 | 79 | 77 | 74 | 76 | 76 | 73 | 72 | 99 |    |    |    |    |    |    |
| 12 | 77 | 76 | 78 | 74 | 73 | 75 | 74 | 73 | 73 | 95 | 96 |    |    |    |    |    |
| 13 | 70 | 71 | 69 | 70 | 70 | 69 | 68 | 67 | 68 | 67 | 68 | 68 |    |    |    |    |
| 14 | 69 | 70 | 69 | 69 | 69 | 69 | 68 | 68 | 68 | 67 | 67 | 67 | 99 |    |    |    |
| 15 | 69 | 70 | 68 | 69 | 69 | 68 | 68 | 67 | 67 | 67 | 67 | 67 | 99 | 95 |    |    |
| 16 | 69 | 69 | 70 | 70 | 69 | 68 | 68 | 68 | 67 | 69 | 69 | 67 | 95 | 95 | 94 |    |

To further demonstrate the versatility of this invention in transferring a variety of foreign genes and the applicability of this invention to plants other than the herbaceous species, different binary vectors were constructed and transferred into aspen (*Populus tremuloides*) tree. Two binary vectors, each containing a cDNA sequence and a neomycin phosphotransferase (NPT II) cDNA encoding kanamycin resistance, were constructed. Each vector was then individually mobilized into *Agrobacterium* strain C58 to create two isolated (engineered) *Agrobacterium* strains. It should be noted that about 50 transgenic tobacco plants were generated by the same technique harboring 4 different sets of foreign genes, as described in the PCT application PCTUS0027704 filed Oct. 6, 2000, entitled "Method of Introducing a Plurality of Genes into Plants," incorporated herein by reference.

Table 4 summarizes the numerical results from simultaneous manipulating xylem-specific expression of 4CL (SEQ ID NO: 10) and CAld5H (SEQ ID NO: 4) in transgenic aspen. After DNA constructs were incorporated into plant cells by *Agrobacterium* mediated transformation, as set forth by the method in accordance with the invention and after PCR confirmation of transgene integration, 14 positive transgenic trees were randomly selected, representing three different trangenic groups, i.e., Groups I, II and III. Group I (plant #21, 22, 23, 25, and 37) consists of those with the integration of only Pt4CL1 cDNA (SEQ ID NO: 7) in the antisense orientation (Table 4). Group II plants (#32, 84, 93, and 94) harbored only sense PtCAld5H cDNA (SEQ ID NO: 3), whereas Group III plants (#71, 72, 74, and 141) contained both antisense Pt4CL1 and sense PtCAld5H transgenes. These transgenic trees were then further analyzed for their lignin and cellulose contents and lignin S/G ratio (Table 4). It is clear that, when compared with the control, untransformed aspen, transgenic plants (#21, 22, 23, 25, and 37) engineered for the suppression of 4CL gene with antisense Pt4CL1 transgene had drastic reductions in their lignin content, with significant increases in their cellulose content. Transgenic plants (#32, 84, 93, 94, and 108) engineered for the overexpression of CAld5H with sense PtCAld5H transgene had pronounced increases in their S/G ratio, but their lignin and cellulose contents remained essentially unaffected. When engineered for the simultaneous suppression of 4CL gene and overexpression of CAld5H gene, transgenic plants (#71, 72, 74, and 141) all exhibited low lignin content, high S/G ratio and elevated cellulose quantity. In summary, these results show that multiple genes carried by individual *Agrobacterium* strains can be integrated simultaneously into the plant genome.

Moreover, it was demonstrated as shown herein below, that transgenic plants with a nearly 30% increase in cellulose content and over 50% lignin quantity reduction, accompanied with a significant augmentation of the S/G ratio, can be easily produced. It is conceivable that more genes can also be efficiently transferred at one time. Only one suitable marker gene is required for this system, although a number of marker genes can also be employed.

TABLE 4

Simultaneous manipulating xylem-specific expression of 4CL (SEQ ID NO: 10) and CAld5H (SEQ ID NO: 4) in transgenic aspen.

| Plant # | | Control | 21 | 22 | 23 | 25 | 37 | 32 | 84 | 93 | 94 | 108 | 71 | 72 | 74 | 141 |
|---|---|---|---|---|---|---|---|---|---|---|---|---|---|---|---|---|
| Gene integrated | 4CL-a | | Y | Y | Y | Y | Y | | | | | | Y | Y | Y | Y |
| | CAld5H-s | | | | | | | Y | Y | Y | Y | Y | Y | Y | Y | Y |
| Lignin content (%) | | 22.4 | 16.0 | 15.3 | 14.4 | 13.1 | 14.9 | 22.4 | 21.6 | 21.1 | 20.7 | 19.7 | 13.2 | 13.7 | 12.4 | 10.7 |
| Lignin S/G ratio | | 2.2 | 2.1 | 2.0 | 2.2 | 2.3 | 2.1 | 4.8 | 4.0 | 5.5 | 4.9 | 3.0 | 3.3 | 3.6 | 3.4 | 2.7 |
| Cellulose content (%) | | 41.4 | 43.1 | ND | ND | 47.3 | ND | 40.0 | ND | 44.7 | ND | ND | ND | 49.2 | ND | 53.3 |

ND: not determined

EXAMPLE 3

Production of Commercially Desirable Agronomic Traits in Transformed Plants

The following genetic transformations illustrate the production of commercially desirable agronomic traits in plants.

Gymnosperms

A. To produce syringyl-enriched lignin in gymnosperm plants, gymnosperm plants are genetically transformed with SAD, CAld5H, and AldOMT genes in the sense orientation driven by any appropriate promoter and via any appropriate genetic transformation system allows. These three genes can be transferred into the host plant either simultaneously (in one or individual constructs) or sequentially (in individual constructs) in any order.

B. To produce decreased lignin content, increased syringyl/guaiacyl (S/G) lignin ratio and increased cellulose quantity in gymnosperm plants, gymnosperm plants are genetically transformed with SAD, CAld5H and AldOMT genes in the sense orientation and 4CL gene in either sense or antisense orientation driven by any appropriate promoter and via any appropriate genetic transformation system. These four genes can be transferred into the host plant either simultaneously (in one or individual constructs) or sequentially (in individual constructs) in any order.

C. To produce decreased lignin content, increased syringyl/guaiacyl (S/G) lignin ratio and increased cellulose quantity in gymnosperm plants, gymnosperm plants are genetically transformed with SAD, CAld5H and AldOMT genes in the sense orientation and 4CL and CAD genes in either sense or antisense orientation driven by any appropriate promoter and via any appropriate genetic transformation system. These five genes can be transferred into the host plant either simultaneously (in one or individual constructs) or sequentially (in individual constructs) in any order.

D. To produce increased lignin content in gymnosperm plants, gymnosperm plants are genetically transformed with 4CL gene in the sense orientation driven by any appropriate promoter and via any appropriate genetic transformation system.

E. To produce increased lignin content and increased syringyl/guaiacyl (S/G) lignin ratio in gymnosperm plants, gymnosperm plants are genetically transformed with SAD, CAld5H, AldOMT, and 4CL genes in the sense orientation driven by any appropriate promoter and via any appropriate genetic transformation system. These four genes can be transferred into the host plant either simultaneously (in one or individual constructs) or sequentially (in individual constructs) in any order.

F. To produce increased lignin content, increased syringyl/guaiacyl (S/G) lignin ratio in gymnosperm plants, gymnosperm plants are genetically transformed with SAD, CAld5H, AldOMT, and 4CL genes in the sense orientation and CAD gene in the antisense orientation driven by any appropriate promoter and via any appropriate genetic transformation system. These four genes can be transferred into the host plant either simultaneously (in one or individual constructs) or sequentially (in individual constructs) in any order.

Angiosperms

A. To produce increased S/G lignin ratio in angiosperm plants, angiosperm plants are genetically transformed with either CAld5H, AldOMT, or SAD genes in sense orientation driven by any appropriate promoter and via any appropriate genetic transformation system. These three genes can be transferred into the host plant either simultaneously (in one or individual constructs) or sequentially (in individual constructs) in any order.

B. To produce decreased lignin content, increased S/G lignin ratio and increased cellulose quantity in angiosperm plants, angiosperm plants are genetically transformed with either SAD, CAld5H, or AldOMT genes in the sense orientation and 4CL gene in the sense or antisense orientation driven by any appropriate promoter and via any appropriate genetic transformation system. These four genes can be transferred into the host plant either simultaneously (in one or individual constructs) or sequentially (in individual constructs) in any order.

C. To produce decreased lignin content, increased S/G lignin ratio and increased cellulose quantity in angiosperm plants, angiosperm plants are genetically transformed with either SAD, CAld5H, or AldOMT genes in the sense orientation and 4CL and CAD genes in the sense or antisense orientation driven by any appropriate promoter and via any appropriate genetic transformation system. These five genes can be transferred into the host plant either simultaneously (in one or individual constructs) or sequentially (in individual constructs) in any order.

D. To produce increased lignin content in angiosperm plants, angiosperm plants are genetically transformed with 4CL gene in the sense orientation driven by any appropriate promoter and via any appropriate genetic transformation system.

E. To produce increased lignin content and increased S/G ratio in angiosperm plants, angiosperm plants are genetically transformed with 4CL in the sense orientation and either SAD, CAld5H, or AldOMT genes also in the sense orientation driven by any appropriate promoter and via any appropriate genetic transformation system. These four genes can be transferred into the host plant either simultaneously (in one or individual constructs) or sequentially (in individual constructs) in any order.

F. To produce increased lignin content and increased S/G ratio in angiosperm plants, angiosperm plants are genetically transformed with 4CL in the sense orientation and either SAD, CAld5H, or AldOMT genes also in the sense orientation and CAD in the antisense orientation driven by any appropriate promoter and via any appropriate genetic transformation system. These four genes can be transferred into the host plant either simultaneously (in one or individual constructs) or sequentially (in individual constructs) in any order.

All publications, patents and patent applications cited herein are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention. Accordingly, it is intended that the present invention be solely limited by the broadest interpretation that can be accorded the appended claims.

REFERENCES

Bugos et al., 1991, *Plant Mol. Biol.* 17:203.
Chang, H. M., and Sarkanen, K. V., 1973, *Tappi* 56:132.
Chiang, V. L., and Funaoka, M., 1990, *Holzforschung* 44:309.
Hu et al., 1999, *Nature Biotech.* 17:808.
Sarkanen, K. V., and Ludwig, C. H., eds (Wiley-Interscience, New York), 639.
Tsai et al., 1994, *Plant Cell Report* 14:94.
Boudet et al., 1995, *New Phytol.* 129:203.
Ibrahim, 1997, *Trends Plant Sci.* 2:249.
Li et al., 1997, *Proc. Natl. Acad. Sci. USA* 94:5461.
Joshi and Chiang, 1998, *Plant Mol. Biol.* 37:663.
Brasileiro et al., 1991, *Plant Mol. Bio.* 17:441.
Brasileiro et al., 1992, *Transgenic Res.* 1:133.
Chen et al., 1998, *Nature Biotechnology* 16, 11:1060.
Chen, Ph.D. Thesis, 1991, North Carolina State University, Raleigh, N.C.
Chen et al., 1999, *Planta* 207:597.
Christou, 1996, *Bio/Technology* 10:667.
Chandler et al., 1989.
Danekar et al., 1987, *Bio/Technology* 5:587.
De Block, 1990, *Plant Physiol.* 93:1110.
Ebinuma et al., 1997, *Proceedings of the National Academic of Sciences* 94:2117.
Ebert et al. 1987.
Fillatti et al., 1987, *Mol. Gen. Genet.* 206:192.
Freudenberg, 1965.
Horsch et al., 1985, *Science* 227:1229.
Howe et al., 1991, *Woody Plant Biotech*. Plenum Press, New York, 283.
Huang et al., 1991, *In Vitro Cell Dev. Bio.* 4:201.
Hudspeth et al., 1989, *Plant Mol. Biol.*, 12:579.
Hu et al., 1998, *Proc. Natl. Acad. Sci. USA* 95:5407.
Hu et al., 1999, *Nat. Biotechnol.* 17:808.
Humphreys et al., 1999, *Proc. Nat. Acad. Sci. USA* 96:10045.
Jornvall et al., 1987, *Eur. J. Biochem.* 167:195.
Jefferson et al., 1987.
Klopfenstein et al., 1991, *Can. J. For. Res.* 21:1321.
Lawton et al., 1987, *Plant Mol. Biol.* 9:31F.
Buxton and Roussel, 1988, *Crop. Sci.* 28:553.
Jung and Vogel, 1986, *J. Anim., Sci.* 62:1703.
Leple et al., 1992, *Plant Cell Reports* 11:137.
Li et al., 1997, *Proc. Natl. Acad. Sci. USA,* 94:5461.
Li et al., 2001, *Plant Cell,* 13:1567.
Li et al, 1997, *Proc. Natl. Acad. Sci. USA* 94:5431.
Li et al., 1999, *Plant Mol. Biol.* 40:555.
Li et al., 2000, *J. Biol. Chem.* 275:6537.
MacKay et al., 1995, *Mol. Gen. Genet.* 247:537.
MacKay et al., 1997.
McGranahan et al., 1988, *Bio/Technology* 6:800.
McGranahan et al., 1990, *Plant Cell Reports* 8:512.
Minocha et al., 1986, *Proc. TAPPI Research and Development Conference*, TAPPI Press, Atlanta, 89.
Nelson et al. 1996, *Pharmacogenetics* 6:1.
Odell et al., 1985, *Nature* 313:810.
Osakabe et al., 1999, *Proc. Nati. Acad. Sci. USA* 96:8955.
Parsons et al., 1986, *Bio/Technology* 4:533.
Pythoud et al., 1987, *Bio/Technology* 5:1323.
Sambrook et al., $2^{nd}$ ed. 1982.
Sullivan et al., 1993, *Plant Cell Reports* 12:303.
Sarkanen, K. V., and Hergert, H. L., 1971, *Lignins: Occurrence, Formation, Structure and Reaction*, K. V. Sarkanen and C. H. Ludwig, eds (New York: Wiley-Interscience), 43.
Trotter, P. C., 1990, *Tech. Assoc. Pulp Paper Ind. J.* 73:198.
Tsai et al., 1998, *Plant Physiol.* 117:101.
Tsai et al., *Plant Cell Reports* 14:94.
Tricoli et al., 1995.
Walker et al., 1987, *PNAS USA* 84:6624.
Wang et al., 1992, *Mol. Cell. Biol.* 12:3399.
Wu et al., 2000, *Plant J.* 22:495.
Yang et al., 1990, *PNAS USA* 87:4144.
Yamazaki et al., 1993, *J. Biochem.* 114:652.
Zhang, X. -H., and Chiang, V. L., 1997, *Plant Physiol.* 113:65.

What is claimed is:

1. A method of producing a transgenic plant, comprising:
   (a) introducing into a plant cell at least one polynucleotide sequence encoding at least two of 4CL, aspen CAld5H, aspen AldOMT, SEQ ID NO: 9, and SEQ ID NO: 2; and
   (b) regenerating the plant cell to produce a transgenic plant.

* * * * *

SEQUENCE LISTING

<160> NUMBER OF SEQ ID NOS: 14

<210> SEQ ID NO 1
<211> LENGTH: 1446
<212> TYPE: DNA
<213> ORGANISM: aspen populus tremuloides
<220> FEATURE:
<221> NAME/KEY: misc_feature
<223> OTHER INFORMATION: SAD

<400> SEQUENCE: 1
tttttttttt tttcctagcc ttccttctcg acgatatttc tctatctgaa gcaagcacca    60

-continued

| | |
|---|---|
| tgtccaagtc accagaagaa gaacaccctg tgaaggcctt cgggtgggct gctagggatc | 120 |
| aatctggtca tctttctccc ttcaacttct ccaggagggc aactggtgaa gaggatgtga | 180 |
| ggttcaaggt gctgtactgc gggatatgcc attctgacct tcacagtatc aagaatgact | 240 |
| ggggcttctc catgtaccct tggttcctg gcatgaaat tgtggggaa gtgacagaag | 300 |
| ttgggagcaa ggtgaaaaag gttaatgtgg gagacaaagt gggcgtggga tgcttggttg | 360 |
| gtgcatgtca ctcctgtgag agttgtgcca atgatcttga aaattactgt ccaaaaatga | 420 |
| tcctgacata cgcctccatc taccatgacg gaaccatcac ttacggtggc tactcagatc | 480 |
| acatggtcgc taacgaacgc tacatcattc gattccccga taacatgccg cttgacggtg | 540 |
| gcgctcctct cctttgtgcc gggattacag tgtatagtcc cttgaaatat tttggactag | 600 |
| atgaacccgg taagcatatc ggtatcgttg gcttaggtgg acttggtcac gtggctgtca | 660 |
| aatttgccaa ggcctttgga tctaaagtga cagtaattag tacctcccct tccaagaagg | 720 |
| aggaggcttt gaagaacttc ggtgcagact cattttttggt tagtcgtgac caagagcaaa | 780 |
| tgcaggctgc cgcaggaaca ttagatggca tcatcgatac agtttctgca gttcacccc | 840 |
| tttgccatt gtttggactg ttgaagtctc acgggaagct tatcttggtg ggtgcaccgg | 900 |
| aaaagcctct tgagctacct gccttttctt tgattgctgg aaggaagata gttgccggga | 960 |
| gtggtattgg aggcatgaag gagacacaag agatgattga ttttgcagca aaacacaaca | 1020 |
| tcacagcaga tatcgaagtt atttcaacgg actatcttaa tacggcgata gaacgtttgg | 1080 |
| ctaaaaacga tgtcagatac cgattcgtca ttgacgttgg caatactttg gcagctacga | 1140 |
| agccctaagg agaagatccc atgttctcga accctttata aaatctgata acatgtgttg | 1200 |
| atttcatgaa taaatagatt atctttggga tttttcttta ataaacgaag tgttctcgaa | 1260 |
| aacttaacat cggcaatacc ctggcagcta cgagaaacgc tttagaattg tttgtaagtt | 1320 |
| tgtttcatta gggtgatacc atgctctcga gtccttttgta agatccattt atagttgcgt | 1380 |
| gaatgctatg aacaaataat atgtttgcgg cttctcttca aaaaaaaaa aaaaaaaaa | 1440 |
| aaaaaa | 1446 |

<210> SEQ ID NO 2
<211> LENGTH: 362
<212> TYPE: PRT
<213> ORGANISM: aspen populus tremuloides

<400> SEQUENCE: 2

```
Met Ser Lys Ser Pro Glu Glu His Pro Val Lys Ala Phe Gly Trp
1               5                   10                  15

Ala Ala Arg Asp Gln Ser Gly His Leu Ser Pro Phe Asn Phe Ser Arg
            20                  25                  30

Arg Ala Thr Gly Glu Glu Asp Val Arg Phe Lys Val Leu Tyr Cys Gly
        35                  40                  45

Ile Cys His Ser Asp Leu His Ser Ile Lys Asn Asp Trp Gly Phe Ser
    50                  55                  60

Met Tyr Pro Leu Val Pro Gly His Glu Ile Val Gly Glu Val Thr Glu
65                  70                  75                  80

Val Gly Ser Lys Val Lys Lys Val Asn Val Gly Asp Lys Val Gly Val
                85                  90                  95

Gly Cys Leu Val Gly Ala Cys His Ser Cys Glu Ser Cys Ala Asn Asp
            100                 105                 110

Leu Glu Asn Tyr Cys Pro Lys Met Ile Leu Thr Tyr Ala Ser Ile Tyr
        115                 120                 125
```

```
His Asp Gly Thr Ile Thr Tyr Gly Gly Tyr Ser Asp His Met Val Ala
    130                 135                 140
Asn Glu Arg Tyr Ile Ile Arg Phe Pro Asp Asn Met Pro Leu Asp Gly
145                 150                 155                 160
Gly Ala Pro Leu Leu Cys Ala Gly Ile Thr Val Tyr Ser Pro Leu Lys
                165                 170                 175
Tyr Phe Gly Leu Asp Glu Pro Gly Lys His Ile Gly Ile Val Gly Leu
            180                 185                 190
Gly Gly Leu Gly His Val Ala Val Lys Phe Ala Lys Ala Phe Gly Ser
        195                 200                 205
Lys Val Thr Val Ile Ser Thr Ser Pro Ser Lys Lys Glu Glu Ala Leu
    210                 215                 220
Lys Asn Phe Gly Ala Asp Ser Phe Leu Val Ser Arg Asp Gln Glu Gln
225                 230                 235                 240
Met Gln Ala Ala Ala Gly Thr Leu Asp Gly Ile Ile Asp Thr Val Ser
                245                 250                 255
Ala Val His Pro Leu Leu Pro Leu Phe Gly Leu Leu Lys Ser His Gly
            260                 265                 270
Lys Leu Ile Leu Val Gly Ala Pro Glu Lys Pro Leu Glu Leu Pro Ala
        275                 280                 285
Phe Ser Leu Ile Ala Gly Arg Lys Ile Val Ala Gly Ser Gly Ile Gly
    290                 295                 300
Gly Met Lys Glu Thr Gln Glu Met Ile Asp Phe Ala Ala Lys His Asn
305                 310                 315                 320
Ile Thr Ala Asp Ile Glu Val Ile Ser Thr Asp Tyr Leu Asn Thr Ala
                325                 330                 335
Ile Glu Arg Leu Ala Lys Asn Asp Val Arg Tyr Arg Phe Val Ile Asp
            340                 345                 350
Val Gly Asn Thr Leu Ala Ala Thr Lys Pro
        355                 360

<210> SEQ ID NO 3
<211> LENGTH: 1764
<212> TYPE: DNA
<213> ORGANISM: aspen populus tremuloides
<220> FEATURE:
<221> NAME/KEY: misc_feature
<223> OTHER INFORMATION: CAld5H

<400> SEQUENCE: 3
taaagtcttg tggattacac aaaatacaga ctgaaaacat ccataggcac caacacataa      60
accatccatg gattctcttg tccaatcttt gcaagcttca cccatgtctc tcttcttgat    120
cgttatctct tcactcttct tcttcggtct cctctctcgc cttcgccgaa gattgccata    180
tccaccaggg cctaaagggt tgccacttgt aggtagcatg cacatgatgg accaaataac    240
tcaccgtggg ttagctaaac tagctaagca atatggtggg ctctttcata tgcgcatggg    300
gtacttgcat atggtcactg tttcatctcc tgaaatagct cgccaagttc tgcaggtcca    360
ggacaacatt ttctccaaca gaccagccaa catagccata agttacttaa cctatgatcg    420
tgcagatatg gcctttgccc actacggtcc tttctggcga cagatgcgta agctctgcgt    480
catgaagctt tttagccgga aagggctgaa atcatgggag tctgtgagag atgaggtgga    540
ctcaatgctt aagacagttg aagccaatat aggcaagcct gtgaatcttg gggaattgat    600
ttttacgttg accatgaaca tcacttacag agcagctttc ggggctaaaa atgaaggaca    660
```

-continued

```
ggatgagttc atcaagattt tgcaggagtt ctctaagctt tttggagcat tcaacatgtc    720
tgatttcatt ccctggctgg gctggattga cccccaaggg ctcagcgcta gacttgtcaa    780
ggctcgcaag gctcttgata gattcatcga ctctatcatc gatgatcata tccagaaaag    840
aaaacagaat aagttctctg aagatgctga aaccgatatg gtcgatgaca tgctagcctt    900
ttatggtgaa gaagcaagga agtagatga atcagatgat ttacaaaaag ccatcagcct    960
tactaaagac aacatcaaag ccataatcat ggatgtgatg tttggtggga cagagacggt   1020
ggcgtcggca atagagtggg tcatggcgga gctaatgaag agtccagagg atcaaaaaag   1080
agtccagcaa gagctcgcag aggtggtggg tttagagcgg cgcgtggagg aaagtgatat   1140
tgacaaactt acgttcttga aatgcgccct caaagaaacc ttaaggatgc acccaccaat   1200
cccacttctc ttacatgaaa cttctgagga tgctgaggtt gctggttatt tcattccaaa   1260
gcaaacaagg gtgatgatca atgcttatgc tattgggaga gacaagaatt catgggaaga   1320
tcctgatgct tttaagcctt caaggttttt gaaaccaggg gtgcctgatt ttaaagggaa   1380
tcactttgag tttattcctt cgggtctgg tcggaggtct tgccccggta tgcagcttgg   1440
gttatacaca cttgatttgg ctgttgctca cttgcttcat tgttttacat gggaattgcc   1500
tgatggcatg aaaccgagtg aacttgacat gactgatatg tttggactca ccgcgccaag   1560
agcaactcga ctcgttgccg ttccgagcaa gcgtgtgctc tgtcctctct aaggaaggga   1620
aaaaggtaag ggatggaaat gaatgggatt cccttctttc gtggattcta tacagaattg   1680
aggccatggt gacaaagggt caatttgcag gttttttttt ttatatatat atatatataa   1740
ttgggttaaa aaaaaaaaa aaaa                                           1764
```

```
<210> SEQ ID NO 4
<211> LENGTH: 514
<212> TYPE: PRT
<213> ORGANISM: aspen populus tremuloides

<400> SEQUENCE: 4

Met Asp Ser Leu Val Gln Ser Leu Gln Ala Ser Pro Met Ser Leu Phe
1               5                   10                  15

Leu Ile Val Ile Ser Ser Leu Phe Phe Gly Leu Leu Ser Arg Leu
            20                  25                  30

Arg Arg Arg Leu Pro Tyr Pro Pro Gly Pro Lys Gly Leu Pro Leu Val
        35                  40                  45

Gly Ser Met His Met Met Asp Gln Ile Thr His Arg Gly Leu Ala Lys
    50                  55                  60

Leu Ala Lys Gln Tyr Gly Gly Leu Phe His Met Arg Met Gly Tyr Leu
65                  70                  75                  80

His Met Val Thr Val Ser Ser Pro Glu Ile Ala Arg Gln Val Leu Gln
                85                  90                  95

Val Gln Asp Asn Ile Phe Ser Asn Arg Pro Ala Asn Ile Ala Ile Ser
            100                 105                 110

Tyr Leu Thr Tyr Asp Arg Ala Asp Met Ala Phe Ala His Tyr Gly Pro
        115                 120                 125

Phe Trp Arg Gln Met Arg Lys Leu Cys Val Met Lys Leu Phe Ser Arg
    130                 135                 140

Lys Arg Ala Glu Ser Trp Glu Ser Val Arg Asp Glu Val Asp Ser Met
145                 150                 155                 160

Leu Lys Thr Val Glu Ala Asn Ile Gly Lys Pro Val Asn Leu Gly Glu
                165                 170                 175
```

-continued

```
Leu Ile Phe Thr Leu Thr Met Asn Ile Thr Tyr Arg Ala Ala Phe Gly
            180                 185                 190

Ala Lys Asn Glu Gly Gln Asp Glu Phe Ile Lys Ile Leu Gln Glu Phe
        195                 200                 205

Ser Lys Leu Phe Gly Ala Phe Asn Met Ser Asp Phe Ile Pro Trp Leu
    210                 215                 220

Gly Trp Ile Asp Pro Gln Gly Leu Ser Ala Arg Leu Val Lys Ala Arg
225                 230                 235                 240

Lys Ala Leu Asp Arg Phe Ile Asp Ser Ile Ile Asp His Ile Gln
            245                 250                 255

Lys Arg Lys Gln Asn Lys Phe Ser Glu Asp Ala Glu Thr Asp Met Val
        260                 265                 270

Asp Asp Met Leu Ala Phe Tyr Gly Glu Glu Ala Arg Lys Val Asp Glu
    275                 280                 285

Ser Asp Asp Leu Gln Lys Ala Ile Ser Leu Thr Lys Asp Asn Ile Lys
    290                 295                 300

Ala Ile Ile Met Asp Val Met Phe Gly Gly Thr Glu Thr Val Ala Ser
305                 310                 315                 320

Ala Ile Glu Trp Val Met Ala Glu Leu Met Lys Ser Pro Glu Asp Gln
            325                 330                 335

Lys Arg Val Gln Gln Glu Leu Ala Glu Val Val Gly Leu Glu Arg Arg
        340                 345                 350

Val Glu Glu Ser Asp Ile Asp Lys Leu Thr Phe Leu Lys Cys Ala Leu
    355                 360                 365

Lys Glu Thr Leu Arg Met His Pro Pro Ile Pro Leu Leu His Glu
            370                 375                 380

Thr Ser Glu Asp Ala Glu Val Ala Gly Tyr Phe Ile Pro Lys Gln Thr
385                 390                 395                 400

Arg Val Met Ile Asn Ala Tyr Ala Ile Gly Arg Asp Lys Asn Ser Trp
            405                 410                 415

Glu Asp Pro Asp Ala Phe Lys Pro Ser Arg Phe Leu Lys Pro Gly Val
        420                 425                 430

Pro Asp Phe Lys Gly Asn His Phe Glu Phe Ile Pro Phe Gly Ser Gly
    435                 440                 445

Arg Arg Ser Cys Pro Gly Met Gln Leu Gly Leu Tyr Thr Leu Asp Leu
    450                 455                 460

Ala Val Ala His Leu Leu His Cys Phe Thr Trp Glu Leu Pro Asp Gly
465                 470                 475                 480

Met Lys Pro Ser Glu Leu Asp Met Thr Asp Met Phe Gly Leu Thr Ala
            485                 490                 495

Pro Arg Ala Thr Arg Leu Val Ala Val Pro Ser Lys Arg Val Leu Cys
        500                 505                 510

Pro Leu

<210> SEQ ID NO 5
<211> LENGTH: 1503
<212> TYPE: DNA
<213> ORGANISM: aspen populus tremuloides
<220> FEATURE:
<221> NAME/KEY: misc_feature
<223> OTHER INFORMATION: AldOMT; GenBank accession number: X62096

<400> SEQUENCE: 5
tcacttcctt tccttacacc ttcttcaacc ttttgtttcc ttgtagaatt caatctcgat      60
caagatgggt tcaacaggtg aaactcagat gactccaact caggtatcag atgaagaggc    120
```

```
acacctcttt gccatgcaac tagccagtgc ttcagttcta ccaatgatcc tcaaaacagc    180
cattgaactc gaccttcttg aaatcatggc taaagctggc cctggtgctt tcttgtccac    240
atctgagata gcttctcacc tcctaccaa aaaccctgat gcgcctgtca tgttagaccg     300
tatcctgcgc ctcctggcta gctactccat tcttacctgc tctctgaaag atcttcctga    360
tgggaaggtt gagagactgt atggcctcgc tcctgtttgt aaattcttga ccaagaacga    420
ggacggtgtc tctgtcagcc ctctctgtct catgaaccag gacaaggtcc tcatggaaag    480
ctggtattat ttgaaagatg caattcttga tggaggaatt ccatttaaca aggcctatgg    540
gatgactgca tttgaatatc atggcacgga tccaagattc aacaaggtct caacaagggg    600
aatgtctgac cactctacca ttaccatgaa gaagattctt gagacctaca aggctttga    660
aggcctcacg tccttggtgg atgttggtgg tgggactgga gccgtcgtta acaccatcgt    720
ctctaaatac ccttcaatca agggcattaa cttcgatctg ccccacgtca ttgaggatgc    780
cccatcttat cccggagtgg agcatgttgg tggcgacatg tttgttagtg tgcccaaagc    840
agatgccgtt ttcatgaagt ggatatgcca tgattggagc gacgcccact gcttaaaatt    900
cttgaagaat tgctatgacg cgttgccgga aaacggcaag gtgatacttg ttgagtgcat    960
tcttcccgtg gctcctgaca caagccttgc caccaaggga gtcgtgcacg ttgatgtcat   1020
catgctggcg cacaaccccg gtgggaaaga gaggaccgag aaggaatttg agggcttagc   1080
taagggagct ggcttccaag gttttgaagt aatgtgctgt gcattcaaca cacatgtcat   1140
tgaattccgc aagaaggcct aaggcccatg tccaagctcc aagttacttg gggttttgca   1200
gacaacgttg ctgctgtctc tgcgtttgat gtttctgatt gcttttttt atacgaggag    1260
tagctatctc ttatgaaaca tgtaaggata agattgcgtt ttgtatgcct gattttctca   1320
aataacttca ctgcctccct caaaattctt aatacatgtg aaaagatttc ctattggcct   1380
tctgcttcaa acagtaaaga cttctgtaac ggaaaagaaa gcaattcatg atgtatgtat   1440
cttgcaagat tatgagtatt gttctaagca ttaagtgatt gttcaaaaaa aaaaaaaaa    1500
aaa                                                                 1503
```

<210> SEQ ID NO 6
<211> LENGTH: 365
<212> TYPE: PRT
<213> ORGANISM: aspen populus tremuloides

<400> SEQUENCE: 6

```
Met Gly Ser Thr Gly Glu Thr Gln Met Thr Pro Thr Gln Val Ser Asp
1               5                   10                  15

Glu Glu Ala His Leu Phe Ala Met Gln Leu Ala Ser Ala Ser Val Leu
            20                  25                  30

Pro Met Ile Leu Lys Thr Ala Ile Glu Leu Asp Leu Leu Glu Ile Met
        35                  40                  45

Ala Lys Ala Gly Pro Gly Ala Phe Leu Ser Thr Ser Glu Ile Ala Ser
    50                  55                  60

His Leu Pro Thr Lys Asn Pro Asp Ala Pro Val Met Leu Asp Arg Ile
65                  70                  75                  80

Leu Arg Leu Leu Ala Ser Tyr Ser Ile Leu Thr Cys Ser Leu Lys Asp
                85                  90                  95

Leu Pro Asp Gly Lys Val Glu Arg Leu Tyr Gly Leu Ala Pro Val Cys
            100                 105                 110

Lys Phe Leu Thr Lys Asn Glu Asp Gly Val Ser Val Ser Pro Leu Cys
```

```
                      115                 120                 125
Leu Met Asn Gln Asp Lys Val Leu Met Glu Ser Trp Tyr Tyr Leu Lys
    130                 135                 140

Asp Ala Ile Leu Asp Gly Gly Ile Pro Phe Asn Lys Ala Tyr Gly Met
145                 150                 155                 160

Thr Ala Phe Glu Tyr His Gly Thr Asp Pro Arg Phe Asn Lys Val Phe
                165                 170                 175

Asn Lys Gly Met Ser Asp His Ser Thr Ile Thr Met Lys Lys Ile Leu
            180                 185                 190

Glu Thr Tyr Lys Gly Phe Glu Gly Leu Thr Ser Leu Val Asp Val Gly
        195                 200                 205

Gly Gly Thr Gly Ala Val Val Asn Thr Ile Val Ser Lys Tyr Pro Ser
    210                 215                 220

Ile Lys Gly Ile Asn Phe Asp Leu Pro His Val Ile Glu Asp Ala Pro
225                 230                 235                 240

Ser Tyr Pro Gly Val Glu His Val Gly Gly Asp Met Phe Val Ser Val
                245                 250                 255

Pro Lys Ala Asp Ala Val Phe Met Lys Trp Ile Cys His Asp Trp Ser
            260                 265                 270

Asp Ala His Cys Leu Lys Phe Leu Lys Asn Cys Tyr Asp Ala Leu Pro
        275                 280                 285

Glu Asn Gly Lys Val Ile Leu Val Glu Cys Ile Leu Pro Val Ala Pro
    290                 295                 300

Asp Thr Ser Leu Ala Thr Lys Gly Val Val His Val Asp Val Ile Met
305                 310                 315                 320

Leu Ala His Asn Pro Gly Gly Lys Glu Arg Thr Glu Lys Glu Phe Glu
                325                 330                 335

Gly Leu Ala Lys Gly Ala Gly Phe Gln Gly Phe Glu Val Met Cys Cys
            340                 345                 350

Ala Phe Asn Thr His Val Ile Glu Phe Arg Lys Lys Ala
        355                 360                 365

<210> SEQ ID NO 7
<211> LENGTH: 1915
<212> TYPE: DNA
<213> ORGANISM: aspen populus tremuloides
<220> FEATURE:
<221> NAME/KEY: misc_feature
<223> OTHER INFORMATION: 4CL

<400> SEQUENCE: 7
ccctcgcgaa actccgaaaa cagagagcac ctaaaactca ccatctctcc ctctgcatct    60
ttagcccgca atggacgcca caatgaatcc acaagaattc atctttcgct caaaattacc   120
agacatctac atcccgaaaa accttcccct gcattcatac gttcttgaga acttgtctaa   180
acattcatca aaaccttgcc tgataaatgg cgcgaatgga gatgtctaca cctatgctga   240
tgttgagctc acagcaagaa gagttgcttc tggtctgaac aagattggta ttcaacaagg   300
tgacgtgatc atgctcttcc taccaagttc acctgaattc gtgcttgctt cctaggcgc    360
tcacacaga ggtgccatga tcactgctgc caatcctttc tccaccctg cagagctagc     420
aaaacatgcc aaggcctcga gagcaaagct tctgataaca caggcttgtt actacgagaa   480
ggttaaagat tttgcccgag aaagtgatgt taaggtcatg tgcgtggact ctgccccgga   540
cggtgcttca cttttcagag ctcacacaca ggcagacgaa aatgaagtgc tcaggtcga    600
cattagtcct gatgatgtcg tagcattgcc ttattcatca gggactacag ggttgccaaa   660
```

-continued

```
aggggtcatg ttaacgcaca aagggctaat aaccagtgtg gctcaacagg tagatggaga      720
caatcctaac ctgtattttc acagtgaaga tgtgattctg tgtgtgcttc ctatgttcca      780
tatctatgct ctgaattcaa tgatgctctg tggtctgaga gttggtgcct cgattttgat      840
aatgccaaag tttgagattg gttctttgct gggattgatt gagaagtaca aggtatctat      900
agcaccagtt gttccacctg tgatgatggc aattgctaag tcacctgatc ttgacaagca      960
tgacctgtct tctttgagga tgataaaatc tggaggggct ccattgggca aggaacttga     1020
agatactgtc agagctaagt ttcctcaggc tagacttggt cagggatatg aatgaccga      1080 ggcaggacct gttctagcaa tgtgcttggc atttgccaag gaaccattcg acataaaacc     1140
aggtgcatgt ggaactgtag tcaggaatgc agagatgaag attgttgacc cagaaacagg     1200
ggtctctcta ccgaggaacc agcctggtga gatctgcatc cggggtgatc agatcatgaa     1260
aggatatctt aatgaccccg aggcaacctc aagaacaata gacaaagaag gatggctgca     1320
cacaggcgat atcggctaca ttgatgatga tgatgagctt ttcatcgttg acagattgaa     1380
ggaattgatc aagtataaag ggtttcaggt tgctcctact gaactcgaag ctttgttaat     1440
agcccatcca gagatatccg atgctgctgt agtaggattg aaagatgagg atgcgggaga     1500
agttcctgtt gcatttgtag tgaaatcaga aaagtctcag gccaccgaag atgaaattaa     1560
gcagtatatt tcaaaacagg tgatcttcta caagagaata aaacgagttt tcttcattga     1620
agcaattccc aaggcaccat caggcaagat cctgaggaag aatctgaaag agaagttgcc     1680
aggcatataa ctgaagatgt tactgaacat ttaaccctct gtcttatttc tttaatactt     1740
gcgaatcatt gtagtgttga accaagcatg cttggaaaag acacgtaccc aacgtaagac     1800
agttactgtt cctagtatac aagctcttta atgttcgttt tgaacttggg aaaacataag     1860
ttctcctgtc gccatatgga gtaattcaat tgaatatttt ggtttcttta atgat          1915
```

<210> SEQ ID NO 8
<211> LENGTH: 1395
<212> TYPE: DNA
<213> ORGANISM: aspen populus tremuloides
<220> FEATURE:
<221> NAME/KEY: misc_feature
<223> OTHER INFORMATION: CAD; GenBank accession number: AF217957

<400> SEQUENCE: 8

```
aaactccatc cctctctctt agcctcgttg tttcaagaaa atgggtagcc ttgaaacaga       60
gagaaaaatt gtaggatggg cagcaacaga ctcaactggg catctcgctc cttacaccta      120
tagtctcaga gatacggggc cagaagatgt tcttatcaag gttatcagct gtggaatttg      180
ccataccgat atccaccaaa tcaaaaatga tcttggcatg tcacactatc ctatggtccc      240
tggccatgaa gtggttggtg aggttgttga ggtgggatca gatgtgacaa agttcaaagc      300
tggagatgtt gttggtgttg gagtcatcgt tggaagctgc aagaattgtc atccatgcaa      360
atcagagctt gagcaatact gcaacaagaa aatctggtct tacaatgatg tctacactga      420
tggcaaaccc acccaaggag gctttgctga atccatggtt gtcgatcaaa agtttgtggt      480
gagaattcct gatgggatgt caccagaaca agcagcgccg ctgttgtgcg ctggattgac      540
agtttacagc ccactcaaac actttggact gaaacagagt gggctaagag gagggatttt      600
aggacttgga ggagtagggc acatgggggt gaagatagca aaggcaatgg acaccatgt      660 aactgtgatt agttccttctg acaagaagcg ggaggaggct atggaacatc ttggtgctga      720 tgaataccctg gtcagctcgg atgtggaaag catgcaaaaa gctgctgatc aacttgacta      780
```

```
tatcatcgat actgtgcctg tggttcaccc tctcgagcct taccttctc tattgaaact    840 tgatggcaag ctgatcttga tgggtgttat taatacccca ttgcagtttg tttcgccaat    900
ggttatgctt gggagaaagt cgatcaccgg gagcttcata gggagcatga aggagacaga    960
ggagatgctt gagttctgca aggaaaaggg attggcctcc atgattgaag tgatcaaaat   1020
ggattatatc aacacagcat tcgagaggct tgagaaaaat gatgtgagat atagattcgt   1080
tgtcgatgtt gctggtagca agcttattcc ctgaacgaca ataccattca tattcgaaaa   1140
aacgcgatat acattgatac ctgtttcaga cttgacttta ttttcgagtg atgtgttttg   1200
tggttcaaat gtgacagttt gtctttgctt ttaaaataaa gaaaagttg agttgttttt    1260 ttatttcat taatgggcat gcgttacctt gtaattgaat gcgctgcatc tggtgatctg   1320
tcccataaac taatctcttg tggcaatgaa agatgacgaa ctttctgaaa aaaaaaaaa    1380 aaaaaaaaaa aaaaa                                                    1395
```

<210> SEQ ID NO 9
<211> LENGTH: 357
<212> TYPE: PRT
<213> ORGANISM: aspen populus tremuloides

<400> SEQUENCE: 9

```
Met Gly Ser Leu Glu Thr Glu Arg Lys Ile Val Gly Trp Ala Ala Thr
1               5                   10                  15

Asp Ser Thr Gly His Leu Ala Pro Tyr Thr Tyr Ser Leu Arg Asp Thr
            20                  25                  30

Gly Pro Glu Asp Val Leu Ile Lys Val Ile Ser Cys Gly Ile Cys His
        35                  40                  45

Thr Asp Ile His Gln Ile Lys Asn Asp Leu Gly Met Ser His Tyr Pro
    50                  55                  60

Met Val Pro Gly His Glu Val Val Gly Glu Val Val Glu Val Gly Ser
65                  70                  75                  80

Asp Val Thr Lys Phe Lys Ala Gly Asp Val Val Gly Val Gly Val Ile
                85                  90                  95

Val Gly Ser Cys Lys Asn Cys His Pro Cys Lys Ser Glu Leu Glu Gln
            100                 105                 110

Tyr Cys Asn Lys Lys Ile Trp Ser Tyr Asn Asp Val Tyr Thr Asp Gly
        115                 120                 125

Lys Pro Thr Gln Gly Gly Phe Ala Glu Ser Met Val Val Asp Gln Lys
    130                 135                 140

Phe Val Val Arg Ile Pro Asp Gly Met Ser Pro Glu Gln Ala Ala Pro
145                 150                 155                 160

Leu Leu Cys Ala Gly Leu Thr Val Tyr Ser Pro Leu Lys His Phe Gly
                165                 170                 175

Leu Lys Gln Ser Gly Leu Arg Gly Gly Ile Leu Gly Leu Gly Gly Val
            180                 185                 190

Gly His Met Gly Val Lys Ile Ala Lys Ala Met Gly His His Val Thr
        195                 200                 205

Val Ile Ser Ser Ser Asp Lys Lys Arg Glu Glu Ala Met Glu His Leu
    210                 215                 220

Gly Ala Asp Glu Tyr Leu Val Ser Ser Asp Val Glu Ser Met Gln Lys
225                 230                 235                 240

Ala Ala Asp Gln Leu Asp Tyr Ile Ile Asp Thr Val Pro Val Val His
                245                 250                 255
```

```
Pro Leu Glu Pro Tyr Leu Ser Leu Leu Lys Leu Asp Gly Lys Leu Ile
            260                 265                 270

Leu Met Gly Val Ile Asn Thr Pro Leu Gln Phe Val Ser Pro Met Val
        275                 280                 285

Met Leu Gly Arg Lys Ser Ile Thr Gly Ser Phe Ile Gly Ser Met Lys
        290                 295                 300

Glu Thr Glu Glu Met Leu Glu Phe Cys Lys Glu Lys Gly Leu Ala Ser
305                 310                 315                 320

Met Ile Glu Val Ile Lys Met Asp Tyr Ile Asn Thr Ala Phe Glu Arg
                325                 330                 335

Leu Glu Lys Asn Asp Val Arg Tyr Arg Phe Val Val Asp Val Ala Gly
                340                 345                 350

Ser Lys Leu Ile Pro
            355

<210> SEQ ID NO 10
<211> LENGTH: 535
<212> TYPE: PRT
<213> ORGANISM: aspen populus tremuloides

<400> SEQUENCE: 10

Met Asn Pro Gln Glu Phe Ile Phe Arg Ser Lys Leu Pro Asp Ile Tyr
1               5                   10                  15

Ile Pro Lys Asn Leu Pro Leu His Ser Tyr Val Leu Glu Asn Leu Ser
                20                  25                  30

Lys His Ser Ser Lys Pro Cys Leu Ile Asn Gly Ala Asn Gly Asp Val
            35                  40                  45

Tyr Thr Tyr Ala Asp Val Glu Leu Thr Ala Arg Arg Val Ala Ser Gly
        50                  55                  60

Leu Asn Lys Ile Gly Ile Gln Gln Gly Asp Val Ile Met Leu Phe Leu
65                  70                  75                  80

Pro Ser Ser Pro Glu Phe Val Leu Ala Phe Leu Gly Ala Ser His Arg
                85                  90                  95

Gly Ala Met Ile Thr Ala Ala Asn Pro Phe Ser Thr Pro Ala Glu Leu
            100                 105                 110

Ala Lys His Ala Lys Ala Ser Arg Ala Lys Leu Leu Ile Thr Gln Ala
        115                 120                 125

Cys Tyr Tyr Glu Lys Val Lys Asp Phe Ala Arg Glu Ser Asp Val Lys
130                 135                 140

Val Met Cys Val Asp Ser Ala Pro Asp Gly Ala Ser Leu Phe Arg Ala
145                 150                 155                 160

His Thr Gln Ala Asp Glu Asn Glu Val Pro Gln Val Asp Ile Ser Pro
                165                 170                 175

Asp Asp Val Val Ala Leu Pro Tyr Ser Ser Gly Thr Thr Gly Leu Pro
            180                 185                 190

Lys Gly Val Met Leu Thr His Lys Gly Leu Ile Thr Ser Val Ala Gln
        195                 200                 205

Gln Val Asp Gly Asp Asn Pro Asn Leu Tyr Phe His Ser Glu Asp Val
    210                 215                 220

Ile Leu Cys Val Leu Pro Met Phe His Ile Tyr Ala Leu Asn Ser Met
225                 230                 235                 240

Met Leu Cys Gly Leu Arg Val Gly Ala Ser Ile Leu Ile Met Pro Lys
                245                 250                 255

Phe Glu Ile Gly Ser Leu Leu Gly Leu Ile Glu Lys Tyr Lys Val Ser
            260                 265                 270
```

```
Ile Ala Pro Val Val Pro Val Met Met Ala Ile Ala Lys Ser Pro
        275                 280                 285

Asp Leu Asp Lys His Asp Leu Ser Ser Leu Arg Met Ile Lys Ser Gly
        290                 295                 300

Gly Ala Pro Leu Gly Lys Glu Leu Glu Asp Thr Val Arg Ala Lys Phe
305                 310                 315                 320

Pro Gln Ala Arg Leu Gly Gln Gly Tyr Gly Met Thr Glu Ala Gly Pro
                325                 330                 335

Val Leu Ala Met Cys Leu Ala Phe Ala Lys Glu Pro Phe Asp Ile Lys
        340                 345                 350

Pro Gly Ala Cys Gly Thr Val Val Arg Asn Ala Glu Met Lys Ile Val
        355                 360                 365

Asp Pro Glu Thr Gly Val Ser Leu Pro Arg Asn Gln Pro Gly Glu Ile
        370                 375                 380

Cys Ile Arg Gly Asp Gln Ile Met Lys Gly Tyr Leu Asn Asp Pro Glu
385                 390                 395                 400

Ala Thr Ser Arg Thr Ile Asp Lys Glu Gly Trp Leu His Thr Gly Asp
                405                 410                 415

Ile Gly Tyr Ile Asp Asp Asp Glu Leu Phe Ile Val Asp Arg Leu
        420                 425                 430

Lys Glu Leu Ile Lys Tyr Lys Gly Phe Gln Val Ala Pro Thr Glu Leu
                435                 440                 445

Glu Ala Leu Leu Ile Ala His Pro Glu Ile Ser Asp Ala Ala Val Val
        450                 455                 460

Gly Leu Lys Asp Glu Asp Ala Gly Glu Val Pro Val Ala Phe Val Val
465                 470                 475                 480

Lys Ser Glu Lys Ser Gln Ala Thr Glu Asp Glu Ile Lys Gln Tyr Ile
                485                 490                 495

Ser Lys Gln Val Ile Phe Tyr Lys Arg Ile Lys Arg Val Phe Phe Ile
                500                 505                 510

Glu Ala Ile Pro Lys Ala Pro Ser Gly Lys Ile Leu Arg Lys Asn Leu
        515                 520                 525

Lys Glu Lys Leu Pro Gly Ile
        530                 535

<210> SEQ ID NO 11
<211> LENGTH: 20
<212> TYPE: DNA
<213> ORGANISM: aspen populus tremuloides
<220> FEATURE:
<221> NAME/KEY: misc_feature
<223> OTHER INFORMATION: Pt4CL1 promoter sense primer

<400> SEQUENCE: 11
caggaatgct ctgcactctg                                             20

<210> SEQ ID NO 12
<211> LENGTH: 20
<212> TYPE: DNA
<213> ORGANISM: aspen populus tremuloides
<220> FEATURE:
<221> NAME/KEY: misc_feature
<223> OTHER INFORMATION: Pt4CL1 sense primer

<400> SEQUENCE: 12
atgaatccac aagaattcat                                             20
```

```
<210> SEQ ID NO 13
<211> LENGTH: 20
<212> TYPE: DNA
<213> ORGANISM: aspen populus tremuloides
<220> FEATURE:
<221> NAME/KEY: misc_feature
<223> OTHER INFORMATION: Pt4CL1 promoter sense primer

<400> SEQUENCE: 13
caggaatgct ctgcactctg                                            20

<210> SEQ ID NO 14
<211> LENGTH: 21
<212> TYPE: DNA
<213> ORGANISM: aspen populus tremuloides
<220> FEATURE:
<221> NAME/KEY: misc_feature
<223> OTHER INFORMATION: PtCal5H antisense primer

<400> SEQUENCE: 14
ttagagagga cagagcacac g                                          21
```